(12) United States Patent
Hochhauser et al.

(10) Patent No.: US 11,925,643 B2
(45) Date of Patent: Mar. 12, 2024

(54) TOLL-LIKE RECEPTOR 4 (TLR4) INHIBITORS AND USE THEREOF

(71) Applicants: MOR RESEARCH APPLICATIONS LTD., Tel Aviv (IL); BAR ILAN UNIVERSITY, Ramat Gan (IL)

(72) Inventors: Edith Hochhauser, Ramat Gan (IL); Arie-Lev Gruzman, Tzur Hadassah (IL); Elena Trifonov, Petah-Tiqwa (IL)

(73) Assignees: MOR RESEARCH APPLICATIONS LTD., Ramat Gan (IL); BAR-ILAN UNIVERSITY, Ramat Gan (IL)

( * ) Notice: Subject to any disclaimer, the term of this patent is extended or adjusted under 35 U.S.C. 154(b) by 86 days.

(21) Appl. No.: 17/057,845

(22) PCT Filed: May 23, 2019

(86) PCT No.: PCT/IB2019/054258
§ 371 (c)(1),
(2) Date: Nov. 23, 2020

(87) PCT Pub. No.: WO2019/224754
PCT Pub. Date: Nov. 28, 2019

(65) Prior Publication Data
US 2021/0196717 A1 Jul. 1, 2021

Related U.S. Application Data

(60) Provisional application No. 62/675,293, filed on May 23, 2018.

(51) Int. Cl.
*A61K 31/513* (2006.01)
*A61K 38/06* (2006.01)
*A61K 38/07* (2006.01)
*A61P 9/10* (2006.01)
*C07D 239/47* (2006.01)
*C07K 5/083* (2006.01)
*C07K 5/087* (2006.01)
*C07K 5/103* (2006.01)
*C07K 5/107* (2006.01)
*C07K 5/113* (2006.01)

(52) U.S. Cl.
CPC ............ *A61K 31/513* (2013.01); *A61K 38/06* (2013.01); *A61K 38/07* (2013.01); *A61P 9/10* (2018.01); *C07D 239/47* (2013.01); *C07K 5/0808* (2013.01); *C07K 5/0812* (2013.01); *C07K 5/1008* (2013.01); *C07K 5/101* (2013.01); *C07K 5/1016* (2013.01); *C07K 5/1021* (2013.01)

(58) Field of Classification Search
None
See application file for complete search history.

(56) References Cited

U.S. PATENT DOCUMENTS

2013/0203649 A1  8/2013  Toshchakov

FOREIGN PATENT DOCUMENTS

| CN | 106883217 A | 6/2017 |
|---|---|---|
| EP | 3305767 B1 | 9/2020 |
| WO | 00/61551 A2 | 10/2000 |
| WO | 2008/145562 A2 | 12/2008 |
| WO | 2012/040719 A2 | 3/2012 |
| WO | 2013/167743 A1 | 11/2013 |

OTHER PUBLICATIONS

Database Registry Chemical Abstracts Service, Columbus, Ohio, Accession No. RN 117973-22-5, Entered STN: Dec. 16, 1988.*
Database Registry Chemical Abstracts Service, Columbus, Ohio, Accession No. RN 2304883-28-9, Entered STN: Apr. 18, 2019.*
Database Registry Chemical Abstracts Service, Columbus, Ohio, Accession No. RN 19036-53-4, Entered STN: Nov. 16, 1984.*
Thierry Roger et al., "Protection from lethal Gram-negative bacterial sepsisby targeting Toll-like receptor 4", PNAS, vol. 106, No. 7, pp. 2348-2352, Feb. 17, 2009.
Daniel Fisher et al., "Determination of 5Methylcytosine in DNA by Gas Chromatography-Electron-Capture Detection", Journal of Chromatography, 452, pp. 51-60 (1988).
Adam S. Ptaziak et al., "Mass Spectrometry of Pyrimidine Derivatives: Electron Impact-induced Decomposition of Molecular Ions of 4-Amino-substituted and 4-Amino-disubstituted 1,2-Dihydro-I-methylpyrimidin-2-ones", Organic Mass Spectrometry, vol. 26, pp. 849-854 (1991).
"4-Amino-1-benzyl-5-methylpyrimidin-2-one, C12H13N3O", https://pubchem.ncbi.nlm.nih.gov/compound/129957084, PubChem, Jan. 18, 2020.
Peter Buchwald et al., "Octanol-Water Partition of Nonzwitterionic Peptides: Predictive Power of a Molecular Size-Based Model", Proteins: Structure, Function, and Genetics 30:86-99 (1998).
I. B. Golovanov et al., "Quantitative Structure-Activity Relationship: IX. Estimation of log P for Some Peptides", Russian Journal of General Chemistry, Jan. 2002, vol. 72, Issue 1, pp. 137-143.
Wenji Piao et al., "Inhibition of TLR4 Signaling by TRAM-Derived Decoy Peptides In Vitro and In Vivo", JThe Journal of Immunology (2013) 190: 2263-2272.
Y. Yang et al., "The emerging role of Toll-like receptor 4 in myocardial inflammation", Cell Death and Disease (2016).
International Search Report and Written Opinion of Application No. PCT/IB2019/054258 dated Sep. 19, 2019, 20 Pages.

(Continued)

*Primary Examiner* — Samantha L Shterengarts
(74) *Attorney, Agent, or Firm* — BROWDY AND NEIMARK, PLLC

(57) ABSTRACT

Peptides, peptidomimetics and small molecules, collectively referred to as "decoy peptides", are provided, which interfere with binding to a TIR domain of a toll-like receptor 4 (TLR4), and inhibit a TLR4-induced signaling pathway. These decoy peptides may be useful for treating diseases associated with induction of TLR4 signaling pathway such as a disease or disorder secondary to a cardiovascular disease, sepsis or an inflammatory disease.

16 Claims, 21 Drawing Sheets

Specification includes a Sequence Listing.

(56) References Cited

OTHER PUBLICATIONS

Extended European Search Report for Application No. EP19807806.5, dated May 12, 2022, 11 pages.
International Preliminary Report on Patentability of Application No. PCT/IB2019/054258 dated Dec. 3, 2020, 11 Pages.
Trifonov L., et al., "Structurally Simple, Readily Available Peptidomimetic 1-Benzyl-5-methyl-4-(n-octylamino)pyrimidin-2(1H)-one Exhibited Efficient Cardioprotection in a Myocardial Ischemia (MI) Mouse Model," Journal of Medicinal Chemistry, Dec. 2018, vol. 61(24), pp. 11309-11326. https://doi.org/10.1021/acs.jmedchem.8b01471.

* cited by examiner

Fig. 4A
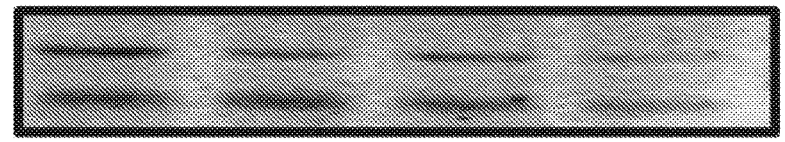
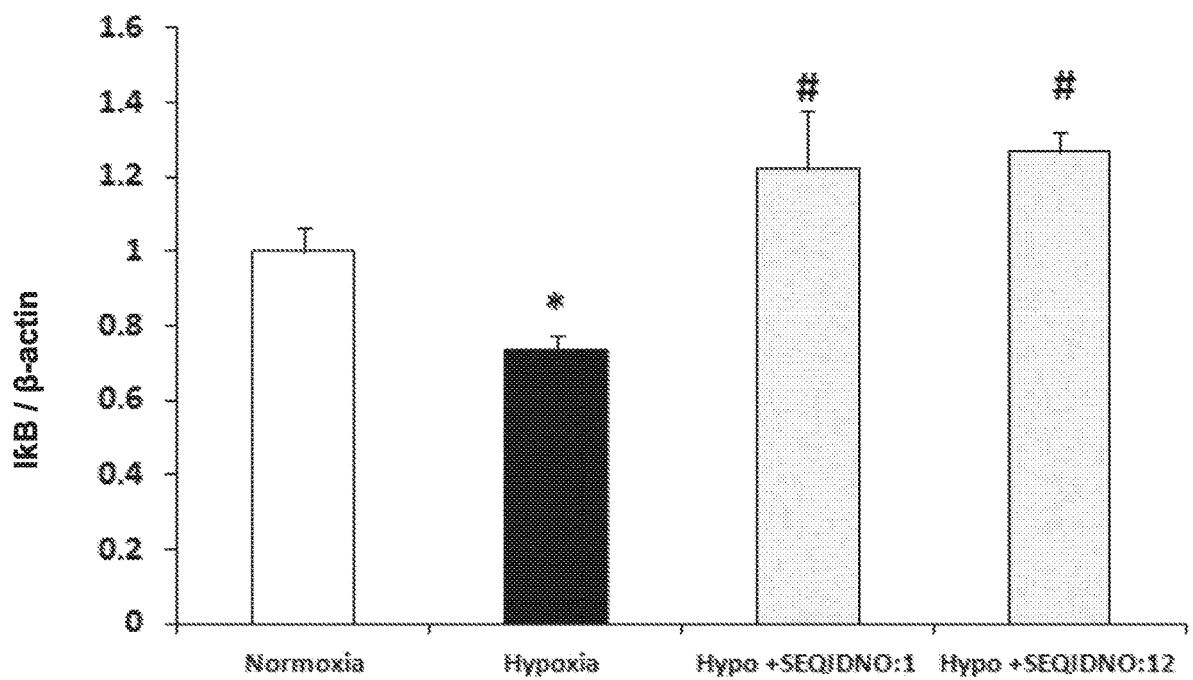
Fig. 4B

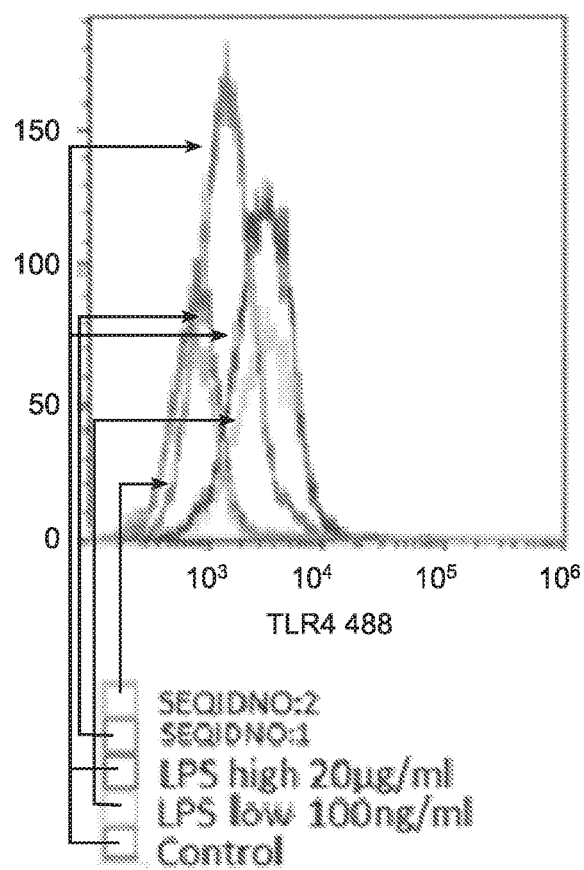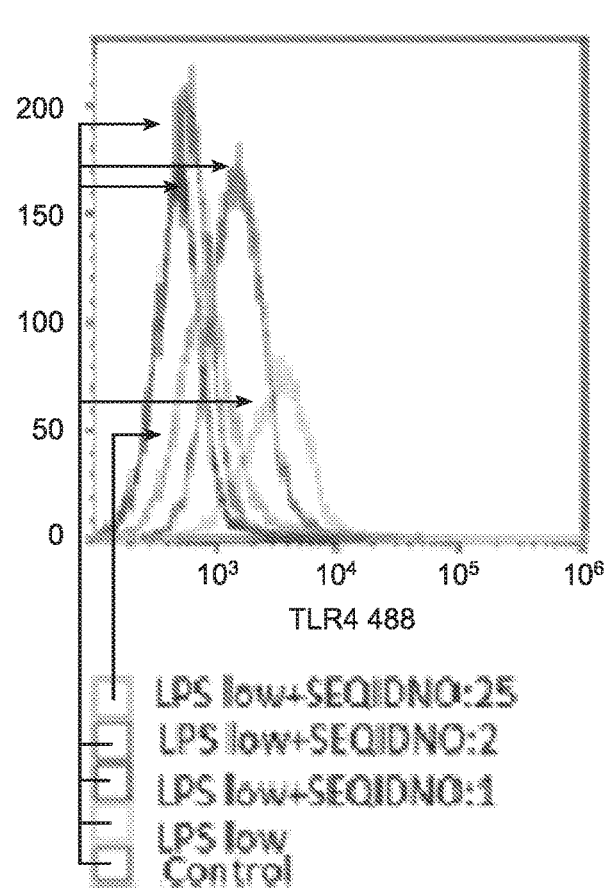

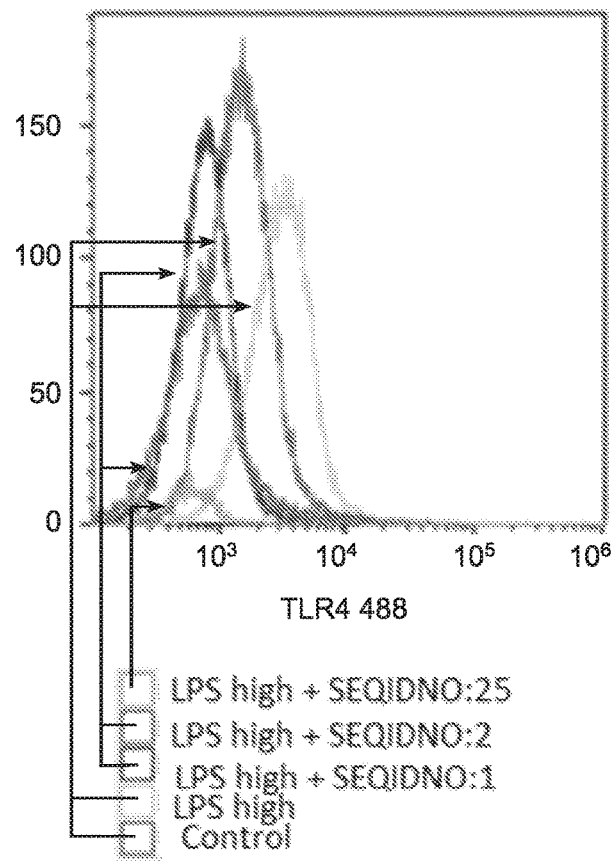
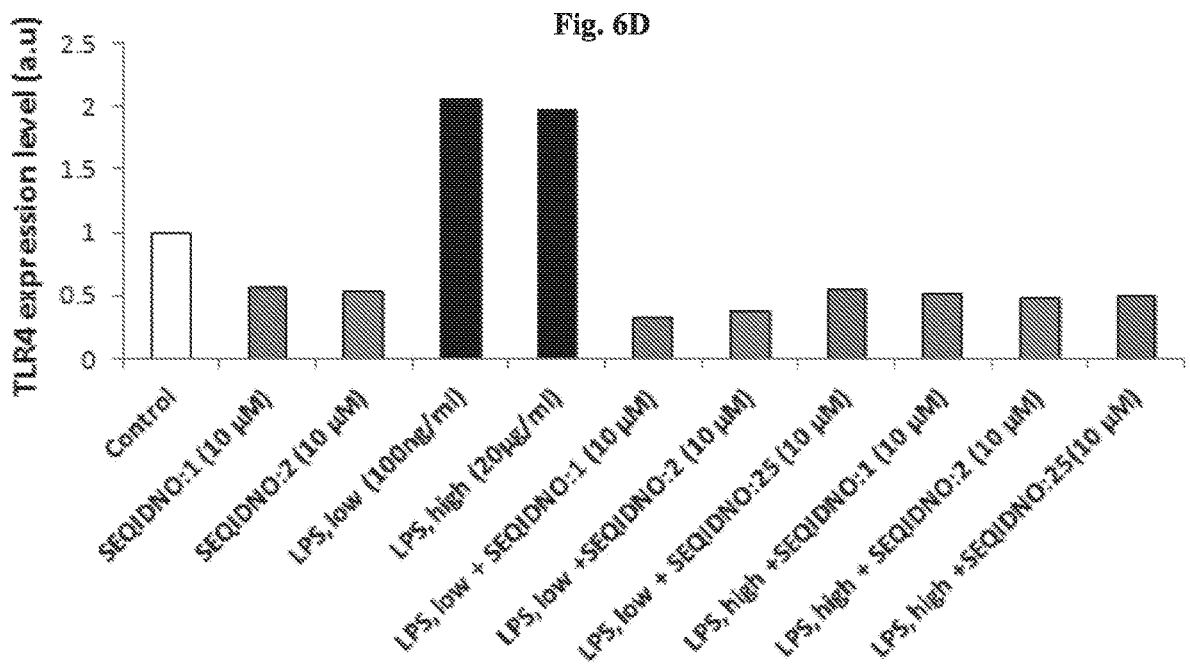

Fig. 17A
Control (7d)
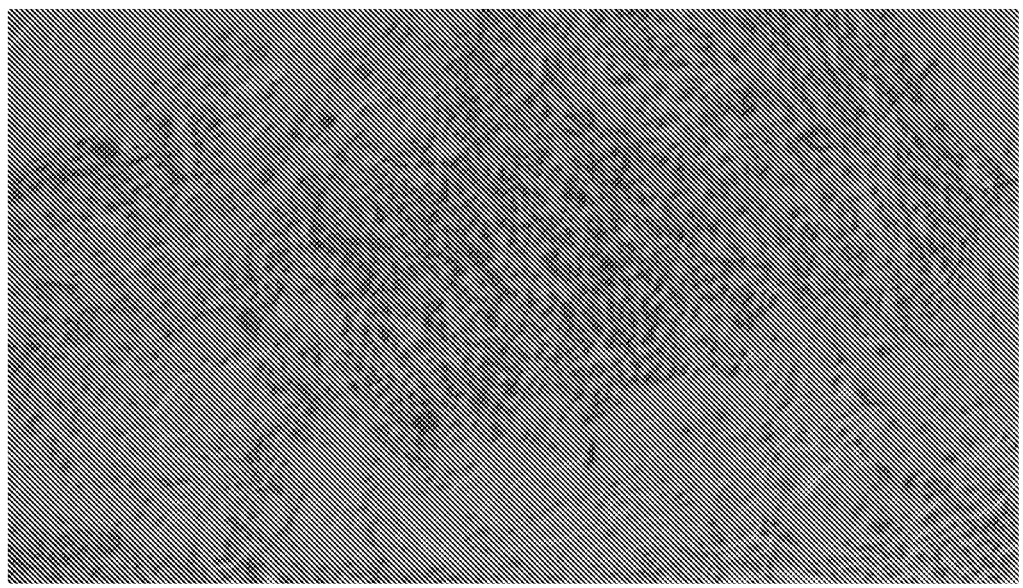
H&E
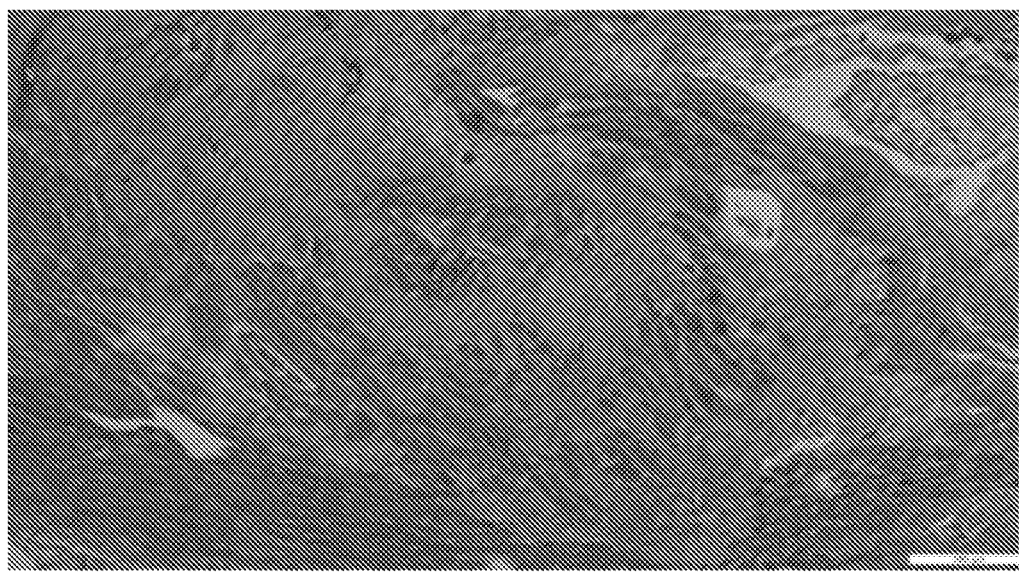
MT

Fig. 17B
0.3 mg/kg PM6 (7d)
H&E
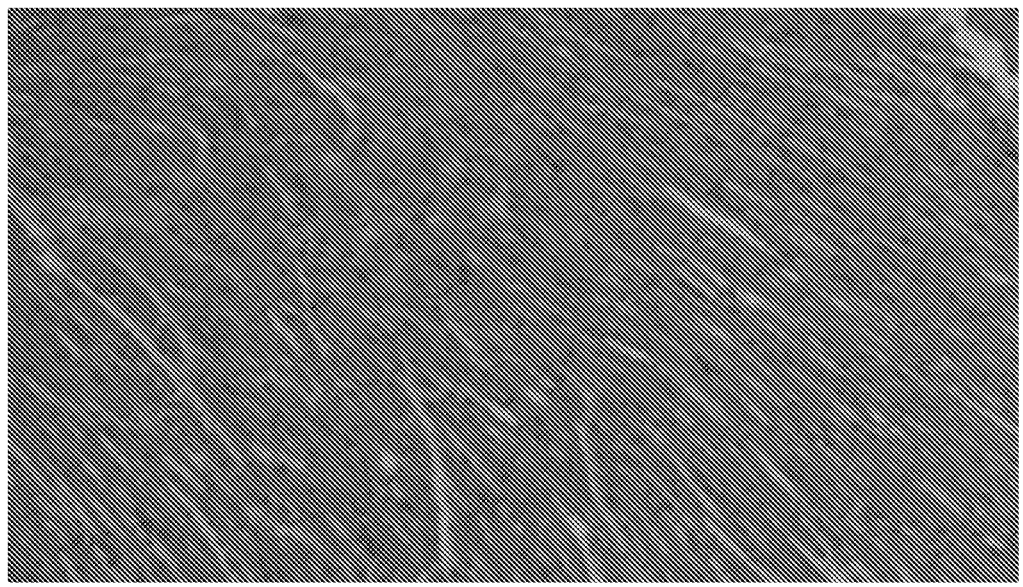
MT
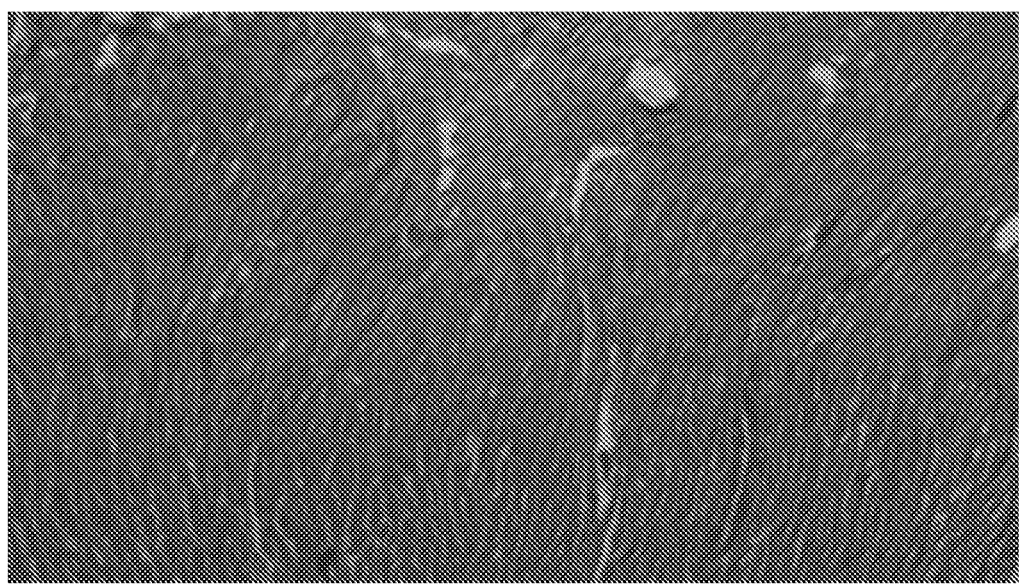

SEQUENCE LISTING

```
<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Ile)
<220> FEATURE:
<221> NAME/KEY: AMIDATION
<222> LOCATION: (4)..(4)
<223> OTHER INFORMATION: NH2 group linked to C-terminal (Ala-NH2)

<400> SEQUENCE: 1

Ile Val Phe Ala
1

<210> SEQ ID NO 2
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Val)
<220> FEATURE:
<221> NAME/KEY: AMIDATION
<222> LOCATION: (4)..(4)
<223> OTHER INFORMATION: NH2 group linked to C-terminal (Glu-NH2)
```

```
<400> SEQUENCE: 2

Val Phe Ala Glu
1

<210> SEQ ID NO 3
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 T

```
<220> FEATURE:
<221> NAME/KEY: ACETYLATION
<222> LOCATION: (1)..(1)
<223> OTHER INFORMATION: N-terminal acetylation (Ac-Met)
<220> FEATURE:
<221> NAME/KEY: AMIDATION
<222> LOCATION: (4)..(4)
<223> OTHER INFORMATION: NH2 group linked to C-terminal (Gly-NH2)

<400> SEQUENCE: 6

Met Pro Cys Gly
1

<210> SEQ ID NO 7
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Glu)
<220> FEATURE:
<221> NAME/KEY: Modified Amino Acid (OtBu-Glu)
<222> LOCATION: (1)..(1)
<223> OTHER INFORMATION: Derivative of Glutamic acid: OtBu protecting
      group (OtBu-Glu)
<220> FEATURE:
<221> NAME/KEY: AMIDATION
<222> LOCATION: (4)..(4)
<223> OTHER INFORMATION: NH2 group linked to C-terminal (Cys-NH2)

<400> SEQUENCE: 7

Glu Met Pro Cys
1

<210> SEQ ID NO 8
<211> LENGTH: 3
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Phe)
<220> FEATURE:
<221> NAME/KEY: AMIDATION
<222> LOCATION: (3)..(3)
<223> OTHER INFORMATION: NH2 group linked to C-terminal (Glu-NH2)

<400> SEQUENCE: 8

Phe Ala Glu
1

<210> SEQ ID NO 9
<211> LENGTH: 3
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Phe)
<220> FEATURE:
<221> NAME/KEY: Modified Amino Acid (bAla)
<222> LOCATION: (2)..(2)
<223> OTHER INFORMATION: beta-Alanine (bAla)
```

```
<220> FEATURE:
<221> NAME/KEY: AMIDATION
<222> LOCATION: (3)..(3)
<223> OTHER INFORMATION: NH2 group linked to C-terminal (Glu-NH2)

<400> SEQUENCE: 9

Phe Ala Glu
1

<210> SEQ ID NO 10
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Ile)
<220> FEATURE:
<221> NAME/KEY: Modified Amino Acid( bAla)
<222> LOCATION: (4)..(4)
<223> OTHER INFORMATION: beta-Alanine (bAla)
<220> FEATURE:
<221> NAME/KEY: AMIDATION
<222> LOCATION: (4)..(4)
<223> OTHER INFORMATION: NH2 group linked to C-terminal (bAla-NH2)

<400> SEQUENCE: 10

Ile Val Phe Ala
1

<210> SEQ ID NO 11
<211> LENGTH: 3
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Xaa)
<220> FEATURE:
<221> NAME/KEY: Unusual Amino Acid (NaphGly)
<222> LOCATION: (1)..(1)
<223> OTHER INFORMATION: Modified amino acid: naphthalene derivative of
      Glycine (naphthalen-1-ylmethyl-L-Gly)
<220> FEATURE:
<221> NAME/KEY: AMIDATION
<222> LOCATION: (3)..(3)
<223> OTHER INFORMATION: NH2 group linked to C-terminal (Glu-NH2)

<400> SEQUENCE: 11

Xaa Ala Glu
1

<210> SEQ ID NO 12
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Ile)
<220> FEATURE:
<221> NAME/KEY: Unusual Amino Acid (NaphGly)
<222> LOCATION: (3)..(3)
<223> OTHER INFORMATION: Modified amino acid: naphthalene derivative of
```

```
        Glycine (naphthalen-1-ylmethyl-L-Gly)
<220> FEATURE:
<221> NAME/KEY: AMIDATION
<222> LOCATION: (4)..(4)
<223> OTHER INFORMATION: NH2 group linked to C-terminal (Ala-NH2)

<400> SEQUENCE: 12

Ile Val Xaa Ala
1

<210> SEQ ID NO 13
<211> LENGTH: 3
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Val)
<220> FEATURE:
<221> NAME/KEY: AMIDATION
<222> LOCATION: (3)..(3)
<223> OTHER INFORMATION: NH2 group linked to C-terminal (Ala-NH2)

<400> SEQUENCE: 13

Val Phe Ala
1

<210> SEQ ID NO 14
<211> LENGTH: 3
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Ile)
<220> FEATURE:
<221> NAME/KEY: AMIDATION
<222> LOCATION: (3)..(3)
<223> OTHER INFORMATION: NH2 group linked to C-terminal (Ala-NH2)

<400> SEQUENCE: 14

Ile Phe Ala
1

<210> SEQ ID NO 15
<211> LENGTH: 3
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: Unusual Amino Acid (tBuGly)
<222> LOCATION: (1)..(1)
<223> OTHER INFORMATION: Derivative of Glycine: tert-butylamine (tBuGly)
<220> FEATURE:
<221> NAME/KEY: AMIDATION
<222> LOCATION: (3)..(3)
<223> OTHER INFORMATION: NH2 group linked to C-terminal (Ala-NH2)

<400> SEQUENCE: 15

Xaa Phe Ala
1

<210> SEQ ID NO 16
```

<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: Unusual Amino Acid (ProGly)
<222> LOCATION: (1)..(1)
<223> OTHER INFORMATION: Derivative of Glycine: propylamine (ProGly)
<220> FEATURE:
<221> NAME/KEY: AMIDATION
<222> LOCATION: (4)..(4)
<223> OTHER INFORMATION: NH2 group linked to C-terminal (Ala-NH2)

<400> SEQUENCE: 16

Xaa Val Phe Ala
1

<210> SEQ ID NO 17
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: Unusual Amino Acid (diMetButGly)
<222> LOCATION: (1)..(1)
<223> OTHER INFORMATION: Derivative of Glycine: (S)-(+)-3,3-dimethyl-2-
      butylamine (diMetButGly)
<220> FEATURE:
<221> NAME/KEY: AMIDATION
<222> LOCATION: (4)..(4)
<223> OTHER INFORMATION: NH2 group linked to C-terminal (Ala-NH2)

<400> SEQUENCE: 17

Xaa Val Phe Ala
1

<210> SEQ ID NO 18
<211> LENGTH: 3
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Phe)
<220> FEATURE:
<221> NAME/KEY: Modified Amino Acid (bAla)
<222> LOCATION: (2)..(2)
<223> OTHER INFORMATION: Modified amino acid: beta Alanine  (bAla)
<220> FEATURE:
<221> NAME/KEY: Modified Amino Acid (OtBuGlu)
<222> LOCATION: (3)..(3)
<223> OTHER INFORMATION: Glutamic acid protected with t-butylester
      (OtBu)Glu)
<220> FEATURE:
<221> NAME/KEY: AMIDATION
<222> LOCATION: (3)..(3)
<223> OTHER INFORMATION: NH2 group linked to C-terminal (Glu-NH2)

<400> SEQUENCE: 18

Phe Ala Glu
1

<210> SEQ ID NO 19
<211> LENGTH: 4
<212> TYPE: PRT
<213> ORGANISM: Artificial Sequence

```
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Val)
<220> FEATURE:
<221> NAME/KEY: Unnatural Amino Acid (NaphGly)
<222> LOCATION: (2)..(2)
<223> OTHER INFORMATION: Modified amino acid: naphthalene derivative of
      Glycine (naphthalen-1-ylmethyl-L-Gly)
<220> FEATURE:
<221> NAME/KEY: AMIDATION
<222> LOCATION: (4)..(4)
<223> OTHER INFORMATION: NH2 group linked to C-terminal (Glu-NH2)

<400> SEQUENCE: 19

Val Xaa Ala Glu
1

<210> SEQ ID NO 20
<211> LENGTH: 3
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Phe)
<220> FEATURE:
<221> NAME/KEY: Modified Amino Acid (OtBuGlu)
<222> LOCATION: (3)..(3)
<223> OTHER INFORMATION: Glutamic acid protected with t-butylester
      (OtBu)Glu)
<220> FEATURE:
<221> NAME/KEY: AMIDATION
<222> LOCATION: (3)..(3)
<223> OTHER INFORMATION: NH2 group linked to C-terminal (Glu-NH2)

<400> SEQUENCE: 20

Phe Ala Glu
1

<210> SEQ ID NO 21
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Ile)
<220> FEATURE:
<221> NAME/KEY: D-Amino Acid (D-Ala)
<222> LOCATION: (4)..(4)
<220> FEATURE:
<221> NAME/KEY: AMIDATION
<222> LOCATION: (4)..(4)
<223> OTHER INFORMATION: NH2 group linked to C-terminal (D-Ala-NH2)

<400> SEQUENCE: 21

Ile Val Phe Ala
1

<210> SEQ ID NO 22
<211> LENGTH: 4
<212> TYPE: PRT
<213> ORGANISM: Artificial Sequence
```

```
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Ile)
<220> FEATURE:
<221> NAME/KEY: D-Amino Acid (D-Phe)
<222> LOCATION: (3)..(3)
<220> FEATURE:
<221> NAME/KEY: AMIDATION
<222> LOCATION: (4)..(4)
<223> OTHER INFORMATION: NH2 group linked to C-terminal (Ala-NH2)

<400> SEQUENCE: 22

Ile Val Phe Ala
1

<210> SEQ ID NO 23
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: ACETYLATION
<222> LOCATION: (1)..(1)
<223> OTHER INFORMATION: N-terminal acetylation (Ac-Ile)
<220> FEATURE:
<221> NAME/KEY: D-Amino Acid (D-Val)
<222> LOCATION: (2)..(2)
<220> FEATURE:
<221> NAME/KEY: AMIDATION
<222> LOCATION: (4)..(4)
<223> OTHER INFORMATION: NH2 group linked to C-terminal (Ala-NH2)

<400> SEQUENCE: 23

Ile Val Phe Ala
1

<210> SEQ ID NO 24
<211> LENGTH: 4
<212> TYPE: PRT
<213> ORGANISM: Artificial Sequence
<220> FEATURE:
<223> OTHER INFORMATION: Decoy peptide designed to mimic the TIR domain
      of TRAM and interfere with TRAM binding to TLR4 TIR domain
<220> FEATURE:
<221> NAME/KEY: Unusual Amino Acid (tPenGly)
<222> LOCATION: (1)..(1)
<223> OTHER INFORMATION: Derivative of Glycine: tert-pentylamine
      (tPenGly)
<220> FEATURE:
<221> NAME/KEY: AMIDATION
<222> LOCATION: (4)..(4)
<223> OTHER INFORMATION: NH2 group linked to C-terminal (Ala-NH2)

<400> SEQUENCE: 24

Xaa Val Phe Ala
1

<210> SEQ ID NO 25
<211> LENGTH: 9
<212> TYPE: PRT
<213> ORGANISM: Artificial Sequence
<220> FEATURE:
<223> OTHER INFORMATION: Prior art peptide TM4- deltaC derived from the
      TRAM TIR domain (Piao et al. J Immunol. 190:2263-2272, 2013)
<220> FEATURE:
<221> NAME/KEY: ACETYLATION
<222> LOCATION: (1)..(1)
```

```
<223> OTHER INFORMATION: N-terminal acetylation (Ac-Ile)

<400> SEQUENCE: 25

Ile Val Phe Ala Glu Met Pro Cys Gly
1               5
```

TOLL-LIKE RECEPTOR 4 (TLR4) INHIBITORS AND USE THEREOF

FIELD AND BACKGROUND

The present disclosure is related, at least in part, to toll-like receptor 4 (TLR4) inhibitors and use thereof, particularly, but not exclusively, in treatment of diseases and disorders associated with activation of TLR4 signaling.

Myocardial infarction (MI) is an ischemic event accompanied by a widespread inflammatory response, central to the pathology of this disease. This inflammatory response promotes cardiomyocyte activation and significant infiltration of cytokine producing leukocytes. Tumor necrosis factor-α (TNF-α), Interleukin (IL)-1β, and IL-6 are among the cytokines secreted immediately after cardiac ischemic injury. These cytokines regulate local inflammatory response and thus play an important role in the apoptosis of cardiomyocytes.

Severe heart damage, resulting in a high level of mortality may also results from sepsis, sometimes even when a patient receives the appropriate therapy. Sepsis is a whole-body inflammatory response to an infection and is one of the most frequent complications of infection. Common signs and symptoms include fever, increased heart rate, increased breathing rate, and confusion. In surgical and intensive care patients, sepsis is the leading cause of mortality. Sepsis can be caused by any kind of bacterial, viral and fungi infection. Sepsis may also occur in the absence of a detectable bacterial invasion, and in these cases microbial toxins, particularly Gram-negative bacterial endotoxin (Lipopolysaccharide-LPS), and endogenous cytokines production have been implicated as initiators and mediators.

Toll-like receptors (TLRs), evolutionarily conserved homologues of the *Drosophila* Toll protein, are type I transmembrane proteins characterized by an extracellular domain containing leucine-rich repeats (LRRs) and a cytoplasmic tail that contains a conserved region called the Toll/interleukin 1 (IL-1) receptor (TIR) domain. These receptors play a critical role in the early innate immune response to invading pathogens. TLRs recognize highly conserved structural motifs known as pathogen-associated molecular patterns (PAMPs), which are exclusively expressed by microbial pathogens and include various bacterial cell wall components such as lipopolysaccharides (LPSs), peptidoglycans (PGNs) and lipopeptides, as well as flagellin, bacterial DNA and viral double-stranded RNA. TLRs also recognize endogenous, danger-associated molecular patterns (DAMPs) that are released from necrotic or dying cells. Ten human and twelve murine TLRs have been characterized, TLR1 to TLR10 in humans, and TLR1 to TLR9, TLR11, TLR12 and TLR13 in mice.

Toll-like receptor 4 (TLR4) is expressed by both immune cells and non-immune cells such as heart myocytes. TLR4 specifically mediates cellular responses generated after binding to the receptor of bacterial LPS, and further responds to endogenous factors produced during different stress stimuli or cell damage i.e., DAMPs such as fibronectin, hyaluronan, high mobility group box 1 protein (HMGB1), and heat shock protein 60. Toll-like receptor 4 signal transduction is mediated by four adaptor proteins, (i) myeloid differentiation primary response 88 (MyD88); (ii) TIR domain-containing adapter protein (TIRAP), also known as MyD88-adapter-like; (iii) TIR domain-containing adapter inducing interferon-β (TRIF); and (iv) TRIF-related adapter molecule (TRAM). Signal transduction by TLR4 culminates in nuclear factor κB (NF-κB) translocation to the nucleus.

Decoy peptides may inhibit cellular signaling pathways presumably by blocking the docking site of their prototype proteins and preventing functional protein-protein interactions. Piao et al. (*J. Immunol.*, 190:2263-2272, 2013) showed that a decoy peptide, IVFAEMPCG, which was derived from the full-length TRAM TIR domain inhibited TLR4 signaling in primary murine macrophages. The same peptide inhibited LPS-induced activation of MyD88-dependent and TRIF-dependent cytokines, as well as mitogen-activated protein kinases (MAPKs) activation in mice.

A continuous need for means for mediating and controlling TLR4-induced signaling pathways, particularly when TLR4 activation is secondary to cardiovascular diseases and might worsen the outcome of these diseases, is yet to be met.

SUMMARY

Activation of toll-like receptor 4 (TLR4) by external stimuli and/or by internal stimuli may result in various pathological situations related to activation of the immune system. Means for mediating and controlling TLR4-induced signaling pathways, particularly in situation when TLR4 activation is highly undesired, are described herein.

In an aspect of the disclosure, a decoy peptide is provided, which is capable of to interfere with binding to a TIR domain of TLR4 and inhibit a TLR4-induced signaling pathway.

In some embodiments, a disclosed decoy peptide is a peptide or peptidomimetic derived from TRAM TIR domain, for example, any of the peptides and peptidomimetics herein designated by SEQ ID NOs:1-24.

In some embodiments, a disclosed decoy peptide is a compound represented by the formula (I):

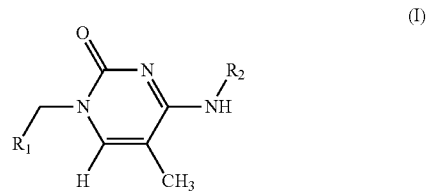

(I)

a stereoisomer, enantiomer or pharmaceutical acceptable salt thereof, wherein $R_1$ and $R_2$, each independently, is H, alkyl, alkenyl, alkynyl, cycloalkyl, heteroalicyclyl, aryl, heteroaryl, haloalkyl, nitro and/or amino group, wherein the alkyl, alkenyl, alkynyl, cycloalkyl, heteroalicyclyl, aryl, heteroaryl, and haloalkyl are as defined herein. For example, $R_1$ may be phenyl or naphthyl, optionally substituted by a haloalkyl group or a nitro group, and/or $R_2$ may be selected from a linear or branched alkyl, optionally substituted with one or more phenyl, amino group, an optionally substituted cycloalkyl, an optionally substituted heteroalicyclic group, an optionally substituted aryl, or an optionally substituted heteroaryl.

In some embodiments, compounds of formula (I) provided herein are compounds designated herein PM1-PM10.

In an aspect of the disclosure, a pharmaceutical composition is provided, comprising a pharmaceutically acceptable carrier and one or more decoy peptides selected from, for example, a peptide or peptidomimetic designated by SEQ ID NOs:1-24; and/or one or more compounds of formula (I) as defined herein, for example, compounds PM1-PM10.

For example, a contemplated pharmaceutical composition may comprise a peptide or peptidomimetic designated by SEQ ID NOs:1, 2, 8, 9, 11, 12, 13, 14 or 16 and/or the compound PM2 or PM6.

In a further aspect of the disclosure, there is provided a method for treatment of a disease or disorder associated with induction of TLR4 signaling pathway in a subject, the method comprising administering to the subject a therapeutically effective amount of a decoy peptide as described herein, or a pharmaceutical composition comprising same, thereby treating the subject. The disease or disorder associated with induction of TLR4 signaling pathway may be, for example, a disease or disorder secondary to a cardiovascular disease or disorder, sepsis, an inflammatory disease, a neurodegenerative disorder, a liver disease, an atherosclerotic disease and a disease or disorder secondary to atherosclerotic disease.

Further provided herein are methods of treating sepsis and a disease or disorder secondary to a cardiovascular disease or disorder in a subject. The secondary disease or disorder associated with a cardiovascular disease or disorder is a disease or disorder that follows or results from a cardiovascular disease or disorder, for example, sepsis, inflammation, infection, an atherosclerotic disease, kidney failure, leg's edema or lung's edema. A contemplated method comprises administering to the subject a therapeutically effective amount of a TLR4 inhibitor, or a formulation comprising same, wherein the TLR4 inhibitor may be, for example, a decoy peptide as defined herein.

The cardiovascular disease or disorder may be, for example, myocardial infarction or angina.

In an aspect of the disclosure, there is provided a kit comprising: (a) a decoy peptide as defined herein; and (b) reagent, means and instructions for applying the kit to a person in need thereof.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present disclosure are herein described, by way of example only, with reference to the accompanying drawings. It is stressed that the particulars shown in the drawings are by way of example and for purposes of illustrative discussion of embodiments of the disclosure. In this regard, the description taken with the drawings makes apparent to those skilled in the art how embodiments of the disclosure may be practiced.

In the drawings:

FIGS. 4A-4B are Western blot presentation (FIG. 4A) and bar graph (FIG. 4B) showing the effect of exemplary peptidomimetics of SEQ ID NOs: 1 and 12 on IκB level in cardiomyocytes under hypoxic versus normal conditions. β-actin level was used as internal control;

FIGS. 6A-6D show the effect of peptidomimetics of SEQ ID NOs:1 and 2 on the level of TLR4 expressed by human macrophages exposed to LPS. FIGS. 6A-6C are flow cytometry histograms showing the fluorescence intensity of Fluor® 488 conjugated to anti-TLR4 antibody (TLR-488; x-axis) versus the number of cells exhibiting a given fluorescence intensity (Count; y-axis). FIG. 6A: control (untreated macrophages; red line); macrophages treated with SEQ ID NOD but not exposed to LPS (purple line); macrophages treated with SEQ ID NO:2 but not exposed to LPS (orange line); macrophages exposed to low concentration of LPS without pre-treatment with a decoy peptide (green line); and macrophages exposed to high concentration of LPS without pre-treatment with a decoy peptide (blue line). FIG. 6B: control (red line); macrophages treated with SEQ ID NOD+low concentration of LPS (blue line); macrophages treated with SEQ ID NO:2+low concentration of LPS (purple line); macrophages treated with SEQ ID NO:25+low concentration of LPS (orange line); and macrophages exposed to low concentration of LPS without pre-treatment with a decoy peptide (green line). FIG. 6C: control (red line); macrophages treated with SEQ ID NOD+high concentration of LPS (blue line); macrophages treated with SEQ ID NO:2+high concentration of LPS (purple line); macrophages treated with SEQ ID NO:25+high concentration of LPS (orange line); and macrophages exposed to high concentration of LPS without pre-treatment with a decoy peptide (green line). FIG. 6D is a bar graph summarizing the flow cytometry data presented in FIGS. 6A-6C;

FIGS. 17A-17B are photographs of histological staining of myocardial tissue (left ventricle) of mice, showing the effect of an exemplary decoy peptide PM6 (0.3 mg/kg) administered 1 hour after ischemia induction, as viewed 7 days after the ischemic event. FIG. 17A: H&E staining and Masson trichrome (MT) staining, respectively, in control mice (ischemic mice not treated with PM6). FIG. 17B: H&E staining and Masson trichrome staining, respectively, in mice treated with PM6.

DETAILED DESCRIPTION

Figure 1A:
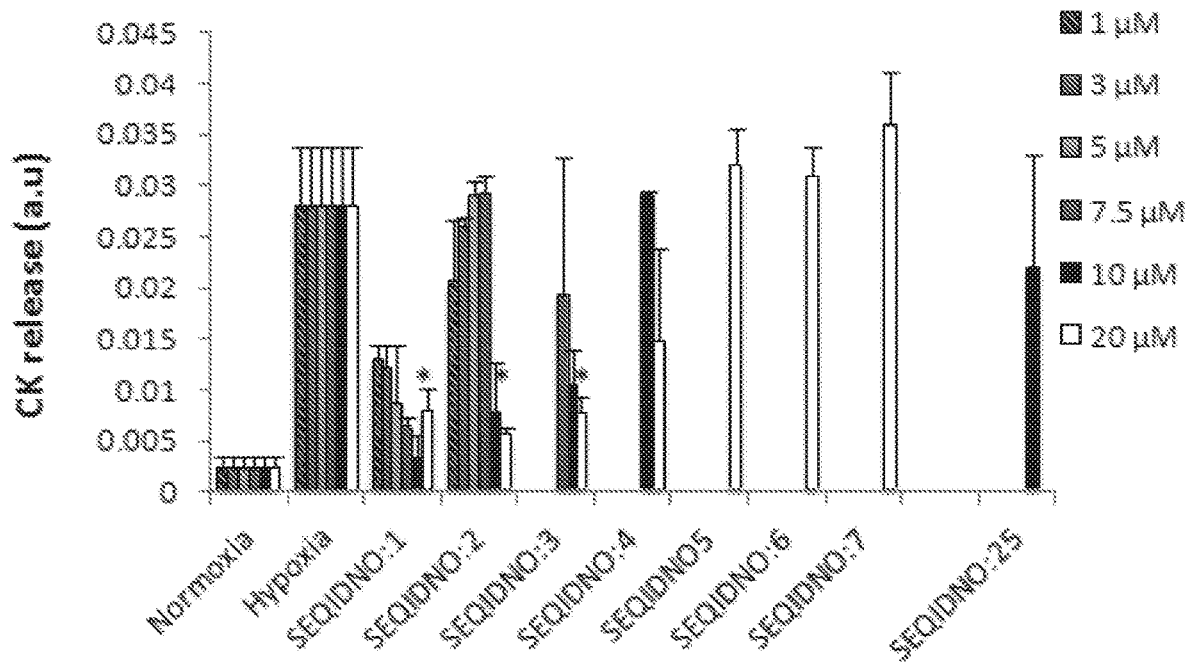
FIGS. 1A-1D are bar graphs showing the in vitro effect of peptidomimetics of SEQ ID NOs:1-7 on release of the enzymes creatine kinase (CK) and lactate dehydrogenase (LDH) by primary cardiomyocytes undergoing hypoxia (FIGS. 1A, 1B) or exposure to LPS (sepsis) (FIGS. 1C, 1D). Primary cardiomyocytes treated with EPS were pretreated with 20 µM of each of peptidomimetics of SEQ ID NOs:1-7. Prior art peptide of SEQ ID NO:25 served as positive control. Release of CK and LDH is expressed in arbitrary units (a.u.)

The present disclosure, in some embodiments thereof, relates to decoy peptides which bind to a TIR domain of TLR4, and use thereof particularly, but not exclusively, in treatment of diseases and disorder associated with activation of a TLR4 signaling pathway.

A link between cardiovascular diseases such as myocardial infarction (MI) and activation of the immune system, based on activation of TLR4 by endogenous ligand secreted following hypoxia, has been previously shown (see, for example, Avlas et al., *PlosOne*, 10(6):e0120175, 2015; Fallach et al., *J Mol Cellular Cardiology*, 48:1236-1244, 2010). The present inventors have previously established, in TLR4 knockout (KO) mice, resistance to the influence of a bacterial lipopolysaccharide (LPS) and hypoxia, and exhibition of a weaker inflammatory response during ischemia as compared to wild-type (WT) mice (see, for example, Avlas et al., *Exp Cell Res*, 348(2):115-122, 2016). It has been further previously established that TLR4 is activated in peripheral monocytes and heart tissue obtained from patients with ischemic heart disease and reduced left ventricular function and, moreover, that coronary revascularization decreases TLR4 expression.

It has been envisaged by the present inventors that inhibition of a TLR4-mediated immune response may be a therapeutic approach useful for reducing the inflammatory cascade in the heart, potentially leading to an improved prognosis following MI- or sepsis-induced cardio damage.

Toll-like receptors (TLRs) serve as pattern recognition receptors in the innate immune response to microbial pathogens and play an important role in identifying microbial associated molecular patterns and in promoting an appropriate immune response. TLRs are also implicated in a number of inflammatory and immune disorders and play a role in cancer. Many single nucleotide polymorphisms have been identified in various TLR genes and are associated with particular diseases.

Stimulation of TLRs e.g., by pathogen-associated microbial patterns (PAMPs) or danger-associated molecular patterns (DAMPs) initiates signaling cascades leading to the activation of transcription factors, such as AP-1 and necrosis factor (NF)-κB, and results in a variety of cellular responses including the production of interferon regulatory factors (IRFs) which activate interferons (IFNs), as well as production and/or secretion of pro-inflammatory cytokines and effector cytokines that direct the adaptive immune response. The cytoplasmic tail of the transmembrane TLRs contains a conserved region called the Toll/interleukin 1 (IL-1) receptor (TIR) domain. Activation of most TLRs is mediated via their TIR domain, whereby a TLR agonist induces recruitment of TIR domain-containing adapter proteins. TLR-mediated signaling is paramount in eradicating microbial infections and promoting tissue repair, thus, its regulation is tight.

"Toll-like receptor 4" or "TLR4", as referred to herein, is a TLR also known as the "LPS receptor", which is activated by bacterial LPS and expressed in leukocytes and cardiac myocytes. Bacterial lipopolysaccharides lower the contractile function of the heart, therefore, TLR4 plays a role in heart function at least for being the only LPS receptor. TLR4 is also activated by several endogenous ligands associated with tissue injury in response to MI. Known DAMPs that are relevant to the heart and wider cardiovascular system include intracellular molecules that are not normally accessible to the immune system, e.g., heat shock proteins (HSPs), high mobility group box 1 protein (HMGB1), histones, S100 proteins, RNA, mitochondrial DNA, cytokines released actively or passively from injured cells (e.g. IL-1α), extracellular matrix (ECM) degradation products, e.g. hyaluronate fragments), specific ECM molecules that are upregulated in response to tissue injury (e.g. Extra Domain A (EDA) splice variant of fibronectin (EDA-FN)), tenascin-C (TN-C) or molecules modified by a pathological environment (e.g. advanced glycation end product (AGE)-modified proteins observed with diabetes).

At least 4 adapter proteins participate in TLR4 signaling: (i) MyD88; (ii) TIR domain-containing adapter protein, also known as MyD88-adapter-like (TIRAP); (iii) TIR domain-containing adapter inducing interferon (IFN)-β (TRIF); and (iv) TRIF-related adapter molecule (TRAM). TIRAP and MyD88, and TRAM and TRIF form two pairs of adapter proteins.

Activated TLR4 dimerizes TIR domains of two receptor molecules and recruits one or two of these distinct pairs of adapter proteins, namely, either TIRAP and MyD88, or TRAM and TRIF. TIRAP and TRAM have been referred to as sorting or bridging adapters, as these adapters are directly engaged by the receptor. Recruitment of a bridging adapter stabilizes the receptor dimer and allows for recruitment of a signaling adapter, MyD88 or TRIF. MyD88 and TIRAP mediate rapid activation of NF-κB and MAPKs and induce MyD88-dependent cytokines, such as TNF-α and IL-1β. TRIF and TRAM activate a different signaling pathway that leads to activation of IFN regulatory factor 3 and IFN regulatory factor 3-dependent genes, such as IFN-β or RANTES.

The term "TIR domain" as used herein, refers to the structural feature Toll/IL-1R domain which is common to TFRs and TFR adapters. A typical TIR domain consists of central five-stranded parallel β-sheet (designated as βA-βE) surrounded by five α-helices (αA-αE). Available crystallographic and functional data suggest that TIR domains interact through topologically diverse structural regions.

The TIR domain is an interaction domain that mediates transient homotypic or heterotypic interactions of signaling proteins that contain TIR domains, thus enabling the formation of signaling complexes. Multiple interactions of TIR domains of TFRs and their adapters are pivotal in the early stages of TFR signaling as these interactions mediate adapter recruitment and thereby stabilize the receptor dimer.

The complexity in mediating TFRs signaling lies in that TFRs such as TFR4 act as double-edged swords, either promoting or inhibiting disease progression. Although activation of the immune system by TFRs, e.g., during microbial invasion, is protective, in some cases it may lead to a dysregulated immune response which causes damage to the organism. Dysregulated immune response may include increased expression of cytokines (TNF-α, IL-1β, IL-6) and overactivation of neutrophils, monocytes and micro vascular endothelial cells. In addition, the neuroendocrine system and plasma coagulating protein cascade can be activated. This activation may induce abnormal coagulation and affect the fibrinolytic system. All these factors lead to severe heart damage. Thus, therapeutic agents targeting TLR4 must be able to antagonize the harmful effects without affecting host defense functions. The present inventors have addressed this duality in TLR4 function by the provision of new decoy peptides that inhibit TLR4-mediated inflammatory response related to, or associated with, cardiovascular diseases and disorders such as MI, while avoiding dysregulated immune response.

The mechanism by which a decoy peptide inhibits signaling is presumed to be blockage of the docking site of the decoy peptide's prototype protein, thereby preventing a functional protein-protein interaction. Therefore, inhibition of a signaling pathway by a decoy peptide often indicates that the inhibitory peptide represents a functional protein interface. Piao et al. (*J Immunol.* 190:2263-2272, 2013) disclose a library of cell-permeable decoy peptides derived from the TRAM TIR domain having the ability to inhibit TLR4 signaling in vitro. One of these peptides: IVFAE-MPCG (designated TM4-ΔC; herein designated by SEQ ID NO:25), has been shown to inhibit TLR4-driven inflammatory response in mice, thereby significantly diminishing circulating cytokine levels induced by a sublethal dose of LPS, and dramatically improving survival of mice challenged with a lethal LPS dose.

The present inventors have designed and successfully obtained peptidomimetics and small peptides based on peptide TM4-AC of Piao et al., which are shorter than the peptides of Piao et al. The present inventors have further designed and successfully obtained unique non-peptidic compounds which bind to TLR4 TIR domain and affect TLR4 activity. While the peptides of Piao et al. were tested only in murine macrophages, the presently described peptides, peptidomimetic and non-peptidic compounds, collectively termed herein "decoy peptides", were tested in human macrophages and, particularly, in cardiomyocytes against both hypoxic- and LPS-induced injury in vitro and in vivo. These decoy peptides inhibited TLR4 signaling in vitro in cardiomyocytes and were active as cardioprotective agents under ischemic conditions in vivo. It has been thus established by the present inventors that the disclosed decoy peptides were able to reduce both hypoxic and septic-like cardiac damage in vivo. As shown in the Examples herein, in two cardiac damage models, the described decoy peptides showed promising biological results in limiting or inhibiting TLR4-induced signaling pathways. For example, Example 7 herein discloses that the decoy peptide designated "PM6" showed 100% rate of survival in myocardial infarction (MI) mice model.

Decoy Peptides

In an aspect of the present disclosure, provided are peptides and peptidomimetics which bind to a TIR domain of TLR4 and inhibit a TLR4-induced signaling pathway of the immune response associated with, for example, sepsis and/or a cardiovascular disease or disorder.

The term "peptide", as used herein, is a is a molecule consisting of two or more amino acids linked together by peptide bonds. The general structure of an amino acid is: R—CH(NH2)COOH, wherein R is H or a chemical group, and each amino acid is a monomer that forms a peptide polymer chain with other amino acids when the carboxyl group (—COOH) of one amino acid reacts with the amino group (—NH2) of another amino acid, forming a covalent bond, termed "peptide bond" or "amide bond", between the amino acid residues and releasing a molecule of water. A peptide molecule may be biologically active on its own or it may act as a subunit for a larger molecule. Proteins are essentially very large peptides, often consisting of multiple peptide subunits. By convention, molecules small enough to be synthesized from the constituent amino acids are called peptides rather than proteins. The dividing line is at about 50 amino acids.

The term "peptidomimetic", as used herein, refers to a small peptide-like chain designed to mimic a peptide. Namely, a peptidomimetic may mimic the biological activity of a peptide, yet it is no longer a peptide in its chemical nature. Peptidomimetics typically arise either from one or more modifications of an existing peptide, or by designing similar systems that mimic peptides. These modifications involve changes to the peptide that will not occur naturally, such as, but not limited to, altered backbones and the incorporation of non-natural amino acids. Irrespective of the structure modification approach, the altered chemical structure is designed to advantageously adjust molecular properties such as stability and/or biological activity.

By a strict definition, a peptidomimetic is a molecule that no longer contains peptide bonds, i.e., amide bonds, between amino acids; however, in the context of embodiments described herein, the term peptidomimetic embraces, besides molecules not containing even a single peptide bond, peptide-like molecules, also termed herein "pseudo-peptides" and "semi-peptides", that contain at least one peptide bond. Non-limiting examples of such peptide-like molecules include β-peptides, which comprise β amino acids having their amino group bonded to the β carbon rather than the α carbon, and peptoids whose side chains are connected to the nitrogen atom of the peptide backbone rather than to the α-carbons. Whether completely or partially non-peptidic, peptidomimetics disclosed herein provide a spatial arrangement of reactive chemical moieties that closely resembles the three-dimensional arrangement of active groups in the precursor peptides from which the peptidomimetics are derived. Thus, non-peptide bonds that enable the arrangement of a peptidomimetic in a similar three-dimensional structure as that of the original peptide can replace peptide bonds. The technique for developing peptidomimetics are conventional and well known in the art.

The term "decoy peptide", as used herein, refers to a peptide, a peptidomimetic and a non-peptidic compound (i.e., not a peptide or peptidomimetic as defined herein) that has a structure resembling or analogous to the structure of a peptide that normally acts as the natural substrate or natural ligand that binds to a certain binding site, e.g., an active site of a receptor or an enzyme. As a result of this structure similarity, a decoy peptide, by acting as "decoy" for the natural substrate's binding site, can interfere with, or disrupt the regular interaction between the natural ligand peptide and its binding site. Serving as distraction at a binding site, decoy peptides can compete with the natural peptides on binding to that target. Decoy peptides may thus temporarily or permanently block a target site, e.g., of an enzyme or a receptor and act as inhibitors or blockers of e.g., an enzyme and/or a receptor.

In the context of embodiments described herein, decoy peptides are designed to mimic the TIR domain of TRAM and thus interfere or compete with wild-type (WT) TRAM on binding to TLR4 TIR domain. Binding of decoy peptides provided herein may, for example, block the TIR receptor site, thereby inhibit or even completely prevent the TLR4 activity.

Exemplary decoy peptides provided herein comprise peptides and peptidomimetic designated by SEQ ID Nos: 1-24, as presented in Table 1:

| SEQ ID | Chemical Name | Peptide sequence | Structural formula |
|---|---|---|---|
| SEQ ID NO: 1 | (2S,3S)-2-acetamido-N-((S)-1-(((S)-1-(((S)-1-amino-1-oxopropan-2-yl)amino)-1-oxo-3-phenylpropan-2-yl)amino)-3-methyl-1-oxobutan-2-yl)-3-methylpentanamide | Ac-Ile-Val-Phe-Ala-NH₂ | 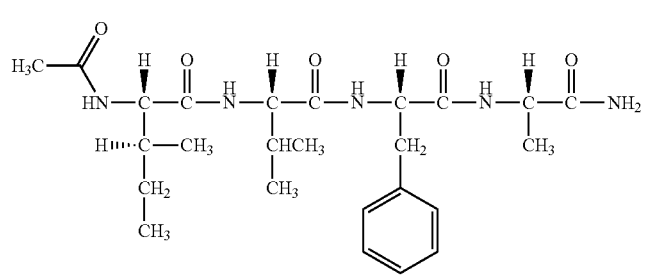 |
| SEQ ID NO: 2 | (4S,7S,10S,13S)-7-benzyl-13-carbamoyl-4-isopropyl-10-methyl-2,5,8,11-tetraoxo-3,6,9,12-tetraazahexadecan-16-oic acid | Ac-Val-Phe-Ala-Glu-NH₂ | 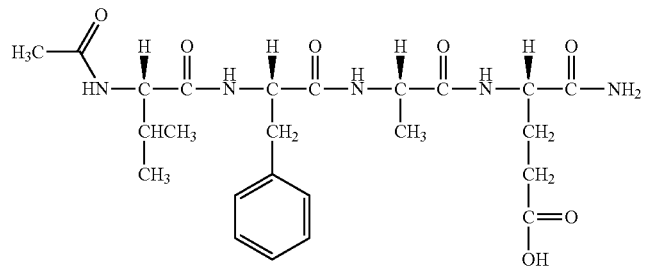 |
| SEQ ID NO: 3 | (S)-4-((S)-2-((S)-2-acetamido-3-phenylpropanamido)propanamido)-5-(((S)-1-amino-4-(methylthio)-1-oxobutan-2-yl)amino)-5-oxopentanoic acid | Ac-Phe-Ala-Glu-Met-NH₂ | 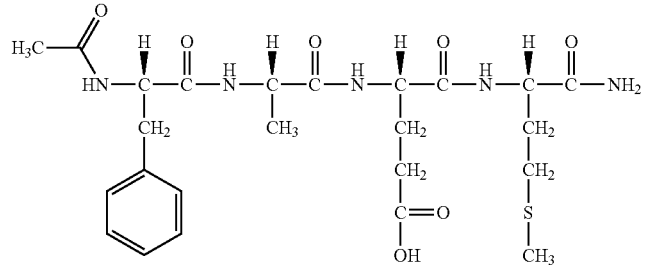 [SMILES: CSCC[C@H](NC(=O)[C@H](CCC(=O)O)NC(=O)[C@H](C)NC(=O)[C@H](Cc1ccccc1)NC(C)=O)C(N)=O] |

-continued

| SEQ ID | Chemical Name | Peptide sequence | Structural formula |
|---|---|---|---|
| SEQ ID NO: 4 | (4S)-4-((S)-2-acetamidopropanamido)-5-(((2S)-1-(2-carbamoylpyrrolidin-1-yl)-4-(methylthio)-1-oxobutan-2-yl)amino)-5-oxopentanoic acid | Ac-Ala-Glu-Met-Pro-NH$_2$ | |
| SEQ ID NO: 5 | (4S)-4-acetamido-5-(((2S)-1-(2-(((S)-1-amino-3-mercapto-1-oxopropan-2-yl)carbamoyl)pyrrolidin-1-yl)-4-(methylthio)-1-oxobutan-2-yl)amino)-5-oxopentanoic acid | Ac-Glu-Met-Pro-Cys-NH$_2$ | |
| SEQ ID NO: 6 | 1-(acetyl-L-methionyl)-N-((S)-1-((2-amino-2-oxoethyl)amino)-3-mercapto-1-oxopropan-2-yl)pyrrolidine-2-carboxamide | Ac-Met-Pro-Cys-Gly-NH$_2$ | |
| SEQ ID NO: 7 | tert-butyl (4S)-4-acetamido-5-(((2S)-1-(2-(((S)-1-amino-3-mercapto-1-oxopropan-2-yl)carbamoyl)pyrrolidin-1-yl)-4-(methylthio)-1-oxobutan-2-yl)amino)-5-oxopentanoate | Ac-Glu(OtBu)-Met-Pro-Cys-NH$_2$ | |
| SEQ ID NO: 8 | (S)-4-((S)-2-((S)-2-acetamido-3-phenylpropanamido)propanamido)-5-amino-5-oxopentanoic acid | Ac-Phe-Ala-Glu-NH$_2$ | |

-continued

| SEQ ID | Chemical Name | Peptide sequence | Structural formula |
|---|---|---|---|
| SEQ ID NO: 9 | (S)-4-(3-((S)-2-acetamido-3-phenylpropanamido) propanamido)-5-amino-5-oxopentanoic acid | Ac-Phe-βAla-Glu-NH₂ | |
| SEQ ID NO: 10 | (2S,3S)-2-acetamido-N-((S)-1-(((S)-1-((3-amino-3-oxopropyl)amino)-1-oxo-3-phenylpropan-2-yl)amino)-3-methyl-1-oxobutan-2-yl)-3-methylpentanamide | Ac-Ile-Val-Phe-βAla-NH₂ | |
| SEQ ID NO: 11 | (4S)-4-((2S)-2-(2-acetamido-2-(naphthalen-1-yl)acetamido) propanamido)-5-amino-5-oxopentanoic acid | Ac-Xaa-Ala-Glu-NH₂ (Xaa = naphthalen-1-ylmethyl-L-Gly) | |
| SEQ ID NO: 12 | (2S,3S)-2-acetamido-N-((2S)-1-((2-(((S)-1-amino-1-oxopropan-2-yl)amino)-1-(naphthalen-1-yl)-2-oxoethyl)amino)-3-methyl-1-oxobutan-2-yl)-3-methylpentanamide | Ac-Ile-Val-Xaa-Ala-NH₂ (Xaa = naphthalen-1-ylmethyl-L-Gly) | |
| SEQ ID NO: 13 | (S)-2-acetamido-N-((S)-1-(((S)-1-amino-1-oxopropan-2-yl)amino)-1-oxo-3-phenylpropan-2-yl)-3-methylbutanamide | Ac-Val-Phe-Ala-NH₂ | |

-continued

| SEQ ID | Chemical Name | Peptide sequence | Structural formula |
|---|---|---|---|
| SEQ ID NO: 14 | (2S,3S)-2-acetamido-N-((S)-1-(((S)-1-amino-1-oxopropan-2-yl)amino)-1-oxo-3-phenylpropan-2-yl)-3-methylpentanamide | Ac-Ile-Phe-Ala-NH₂ | |
| SEQ ID NO: 15 | (S)-N-((S)-1-amino-1-oxopropan-2-yl)-2-(2-(tert-butylamino)acetamido)-3-phenylpropanamide | Xaa-Phe-Ala-NH₂ (Xaa = tBuGly) | |
| SEQ ID NO: 16 | (S)-N-((S)-1-(((S)-1-amino-1-oxopropan-2-yl)amino)-1-oxo-3-phenylpropan-2-yl)-3-methyl-2-(2-(propylamino)acetamido)butanamide | Xaa-Val-Phe-Ala-NH₂ (Xaa = ProGly) | |
| SEQ ID NO: 17 | (S)-N-((S)-1-(((S)-1-amino-1-oxopropan-2-yl)amino)-1-oxo-3-phenylpropan-2-yl)-2-(2-(((S)-3,3-dimethylbutan-2-yl)amino)acetamido)-3-methylbutanamide | Xaa-Val-Phe-Ala-NH₂ (Xaa = diMetButGly) | |
| SEQ ID NO: 18 | tert-butyl (S)-4-(3-((S)-2-acetamido-3-phenylpropanamido)propanamido)-5-amino-5-oxopentanoate | Ac-Phe-βAla-Glu(OtBu)-NH₂ | |
| SEQ ID NO: 19 | (4S,7S,10S,13S)-13-carbamoyl-4-isopropyl-10-methyl-7-(naphthalen-1-ylmethyl)-2,5,8,11-tetraoxo-3,6,9,12-tetraazahexadecan-16-oic acid | Ac-Val-Xaa-Ala-Glu-NH₂ (Xaa = naphthalen-1-ylmethyl-L-Gly) | |

| SEQ ID | Chemical Name | Peptide sequence | Structural formula |
|---|---|---|---|
| SEQ ID NO: 20 | tert-butyl (S)-4-((S)-2-((S)-2-acetamido-3-phenylpropanamido)propanamido)-5-amino-5-oxopentanoate | Ac-Phe-Ala-Glu(OtBu)-NH₂ | |
| SEQ ID NO: 21 | (2S,3S)-2-acetamido-N-((S)-1-(((S)-1-(((R)-1-amino-1-oxopropan-2-yl)amino)-1-oxo-3-phenylpropan-2-yl)amino)-3-methyl-1-oxobutan-2-yl)-3-methylpentanamide | Ac-Ile-Val-Phe-D-Ala-NH₂ | |
| SEQ ID NO: 22 | (2S,3S)-2-acetamido-N-((S)-1-(((R)-1-(((S)-1-amino-1-oxopropan-2-yl)amino)-1-oxo-3-phenylpropan-2-yl)amino)-3-methyl-1-oxobutan-2-yl)-3-methylpentanamide | Ac-Ile-Val-D-Phe-Ala-NH₂ | |
| SEQ ID NO: 23 | (2S,3S)-2-acetamido-N-((R)-1-(((S)-1-(((S)-1-amino-1-oxopropan-2-yl)amino)-1-oxo-3-phenylpropan-2-yl)amino)-3-methyl-1-oxobutan-2-yl)-3-methylpentanamide | Ac-Ile-D-Val-Phe-Ala-NH₂ | |
| SEQ ID NO: 24 | (S)-N-((S)-1-(((S)-1-amino-1-oxopropan-2-yl)amino)-1-oxo-3-phenylpropan-2-yl)-3-methyl-2-(2-(tert-pentylamino)acetamido)butanamide | Xaa-Val-Phe-Ala-NH₂ (Xaa = tPenGly) | |

In some embodiments, the decoy peptide provided by the present disclosure is a compound represented by the general formula (I):

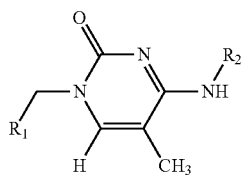

(I)

a stereoisomer, enantiomer or pharmaceutically acceptable salt thereof, wherein $R_1$ and $R_2$ each independently is H, alkyl, alkenyl, alkynyl, cycloalkyl, heteroalicyclyl, aryl, heteroaryl, haloalkyl, nitro and/or amino group.

As used herein, the term "alkyl" refers to a saturated hydrocarbon group comprising straight chain and branched chain hydrocarbons. For example, the alkyl group may have 1 to 20 carbon atoms (herein designated "$(C_1-C_{20})$alkyl"), for example, 1 carbon atom, 2 carbon atoms, 3 carbon atoms, etc., up to and including 20 carbon atoms. Exemplary alkyl groups include, but are not limited to, methyl, ethyl, propyl, isopropyl, butyl, isobutyl, sec-butyl, tert-butyl, pentyl, hexyl, and decanyl. In some embodiments, the alkyl is a medium size alkyl having 1 to 10 or 1 to 8 carbon atoms. In exemplary embodiments, the alkyl is a lower alkyl having 1 to 6 or 1 to 4 carbon atoms.

An "alkenyl" group refers to a partially unsaturated hydrocarbon group comprising straight chain and branched chain partially unsaturated hydrocarbons, which consists of at least two carbon atoms and at least one carbon-carbon double bond. For example, the alkenyl may be a medium size alkenyl having 2 to 10 or 2 to 8 carbon atoms. In exemplary embodiments, the alkenyl is a lower alkenyl having 2 to 4 carbon atoms ($(C_2-C_4)$alkenyl). Non-limiting examples of alkenyl groups include ethenyl (vinyl), propenyl, butenyl, pentenyl and hexenyl.

An "alkynyl" group refers to a partially unsaturated hydrocarbon group comprising straight chain and branched chain partially unsaturated hydrocarbons, which consists of at least two carbon atoms and at least one carbon-carbon triple bond. For example, the alkynyl may be a medium size alkynyl having 2 to 10 or 2 to 8 carbon atoms. In exemplary embodiments, the alkynyl is a lower alkynyl having 2 to 4 carbon atoms ($(C_2-C_4)$alkynyl). Non-limiting examples of alkynyl groups include ethynyl, propynyl, butynyl, pentynyl and hexynyl.

A "cycloalkyl" group refers to a saturated, all-carbon monocyclic or polycyclic (fused ring, i.e., rings which share an adjacent pair of carbon atoms) group, having 3 to 20, for example, 3 to 8 carbon atoms ($(C_3-C_8)$cycloalkyl). Non-limiting examples of cycloalkyl groups include cyclopropanyl, cyclobutanyl, cyclopentanyl, cyclohexanyl and cycloheptanyl.

An "aryl" group refers to an all-carbon monocyclic or polycyclic (fused-ring) group having 6 to 18, for example, 6 to 14 or 6 to 10, carbon atoms forming a completely conjugated pi-electron system (i.e., the aryl is a non-saturated group). Examples, without limitation, of aryl groups include phenyl, naphthyl and anthracenyl.

A "heteroaryl" group, as used herein, refers to a monocyclic or polycyclic (fused ring) group having in the ring(s) one or more heteroatoms such as nitrogen, oxygen and/or sulfur and, in addition, having a completely conjugated pi-electron system (i.e. the heteroaryl is a non-saturated group). Examples, without limitation, of heteroaryl groups include pyrrolyl, furanyl, thiophenyl, imidazolyl, oxazolyl, thiazolyl, pyrazolyl, pyridinyl, pyrimidinyl, quinolinyl, isoquinolinyl, phthalimidyl, and purinyl.

A "heteroalicyclic" group, as used herein, refers to a monocyclic or polycyclic (e.g., a fused ring group as defined herein) having in the ring(s) one or more heteroatoms such as nitrogen, oxygen and/or sulfur. The rings may also have one or more double bonds. However, the rings do not have a completely conjugated pi-electron system (i.e., the heteroalicyclyl may be partially saturated). Representative examples are piperidinyl, piperazinyl, tetrahydrofuranyl, tetrahydropyranyl, morpholinyl, pyrrolinyl and the like.

As used herein, the terms "halogen" and "halo" are interchangeable and include chloro (Cl), bromo (Br), iodo (I) and fluoro (F).

Any of the alkyl, alkenyl, alkynyl, cycloalkyl, aryl, heteroaryl and/or heteroalicyclyl groups as defined herein may be substituted or unsubstituted. When substituted, the substituent group can be, for example, S, N, alkyl, mono-, di- or tri-haloalkyl such as fluoroalkyl, —O—$(C_1-C_8)$alkyl, —O—$(C_3-C_8)$cycloalkyl, hydroxyalkyl, —$(C_3-C_8)$cycloalkyl, alkenyl, alkynyl, aryl, heteroaryl, heteroalicyclyl, halo, OH, —O-aryl, —SH, —S—$(C_1-C_8)$alkyl, —S—$(C_3-C_8)$cycloalkyl, —S-aryl, —O—S═O, —S(═O)$_2$—R', —CN, —NO$_2$, ═O, aralkoxyl, alkylcarbamido, arylcarbamido, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, alkylsulfonylamido, alkylsulfinyl, arylsulfinyl, sulfonylamides, sulfones, P(═O) (OR')(OR"), —PR'R", —C(═O)—R', —C(═S)—R', —C(═O)—O—R', —C(═S)—O—R', —OC(═O)—NR'R", —OC(═S)—NR'R", —S(═O)$_2$—NR'R", and —NR'R", where R' and R", each independently, is hydrogen, alkyl, alkenyl, cycloalkyl, aryl, heteroaryl (bonded through a ring carbon) or heteroalicyclyl (bonded through a ring carbon), as these terms are defined herein.

In some embodiments, $R_1$ is aryl such as phenyl or naphthyl, optionally substituted, for example by haloalkyl group, e.g., —CF$_3$ or a nitro group (—NO$_2$)

In some embodiments, $R_2$ is a linear or branched ($C_1-C_{10}$) alkyl, for example, methyl, propyl, butyl, sec-butyl, pentyl or decanyl, optionally substituted with one or more of any of the substituents defined herein, for example an aryl such as phenyl, or an amino group.

In some embodiments, $R_2$ is a cycloalkyl, for example, cyclopentyl or cyclohexyl, optionally substituted with any of the substituents defined herein.

In some embodiments, $R_2$ is an optionally substituted aryl, heteroaryl or heteroalicyclic group, for example, phenyl, naphthyl, antracyl, phenanthrenyl, tetracenyl, chrysenyl, triphenylenyl, pyrenyl, tetrahydrofuryl, furanyl, thiophenyl, pyrrolyl, 2H-pyrolyl, 2,5-dihydro-1H-pyrrolyl, pyrrolidinyl, oxazolyl, thiazolyl, imidazolyl, 4,5-dihydro-1H-imidazolyl, imidozolinyl, pyrazolyl, 4,5-dihydro-1H-pyrazolyl, pyrazolinyl, isoxazolyl, isothiazolyl, 1,2,3-oxadiazolyl, 1,3,4-oxadiazolyl, 1.2.4-oxadiazolyl, 1,2,3-thiadiazolyl, 1,2,3-triazolyl, 1,2,4-triazolyl, tetrazolyl, 1,2,3,4-oxatriazolyl, 2H-pyranyl, 3,4-dihydro-2H-pyranyl, 1,4-dioxanyl, morpholinyl, piperidinyl, piperazinyl, pyridinyl, pyrazinyl, pyrimidinyl, pyridazinyl, benzofuryl, benzothiophenyl, benzoxazolyl, benzothiazolyl, indolyl, indolinyl, benzoimidazolyl indazolyl, benzotriazolyl, 1H-pyrrolo-[3,2-b]pyrazinyl, 1H-pyrrolo-[3,2-c]pyridinyl, 1.3.5-triazinyl, pyrrolo-[2, 3-c]pyridinyl, pyrrolo-[2,3-b]pyridinyl, 7H-pyrrolo-[2,3-d] pyrimidinyl, 5H-pyrrolo-[3,2-d]pyrimidinyl, 7H-purinyl, indolizinyl, pyrrolo-[1,2-a]pyrimidinyl, pyrrolo-[1,2-a] pyrazinyl, pyrrolo-[1,2-c]pyrimidinyl, pyrrolo-[1,2-b] pyridazinyl, imidazol[4,5-b]pyridinyl, pyrazolo[1,5-a] pyridinyl, imidazo[1,5-a]pyridinyl, imidazo[1,5-b] pyridazinyl, imidazo[1,2-a]pyridinyl, imidazo[1,2-b] pyridazinyl, imidazo[1,2-c]pyrimidinyl, imidazo[1,2-a] pyrazinyl, imidazo[1,2-a]pyrimidinyl, [1,2,3]triazolo[4,3-a] pyridinyl, [1,2,3]triazolo[1,5-a]pyridinyl, quinolinyl, isoquinolinyl, cinnolinyl, quinazolinyl, quinoxalinyl, phthalazinyl, pyrido[2,3-b]pyrazinyl, pteridinyl, pyrido[3,4-d] pyridazinyl, 1,6-naphthyridinyl, 1,8-naphthyridinyl, 9H-carbazolyl, dibenzofuranyl and dibenzothiophenyl.

Each of the aryl, heteroaryl or heteroalicyclic group may be unsubstituted or substituted with one or more substituents as defined herein. For example, $R^2$ may be phenyl substituted with a carboxylic acid group, such as a carboxylic acid and a carboxylic acid ester, at the para, orto or at the meta position; or $R^2$ may be benzyl ester group or benzoic acid group.

Exemplary peptidomimetics encompassed by general formula (I) provided herein are compound PM1-PM10:

1-benzyl-4-(sec-butylamino)-5-methylpyrimidin-2(1H)-one (PM1);

1-benzyl-4-(isopentylamino)-5-methylpyrimidin-2(1H)-one (PM2);

1-benzyl-4-(cyclopentylamino)-5-methylpyrimidin-2(1H)-one (PM3);

1-benzyl-4-((3-(dimethylammo)propyl)amino)-5-methylpyrimidin-2(1H)-one (PM4);

1-benzyl-4-(benzylamino)-5-methylpyrimidin-2(1H)-one (PM5);

1-benzyl-5-methyl-4-(octylamino)pyrimidin-2(1H)-one (PM6);

5-methyl-1-(4-nitrobenzyl)-4-(octylamino)pyrimidin-2(1H)-one (PM7);

5-methyl-1-(naphthalen-2-ylmethyl)-4-(octylamino)pyrimidin-2(1H)-one (PM8);

5-methyl-4-(octylamino)-1-(4-(trifluoromethyl)benzyl)pyrimidin-2(1H)-one (PM9); and 1-benzyl-4-(decylamino)-5-methylpyrimidin-2(1H)-one (PM10).

These exemplary decoy peptides are presented in Table 2:

| Compound No. | Chemical name | Chemical structure |
| --- | --- | --- |
| PM1 | 1-benzyl-4-(sec-butylamino)-5-methylpyrimidin-2(1H)-one | 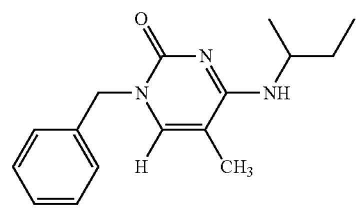 [SMILES: CCC(C)Nc1nc(=O)n(Cc2ccccc2)cc1C] |
| PM2 | 1-benzyl-4-(isopentylamino)-5-methylpyrimidin-2(1H)-one | 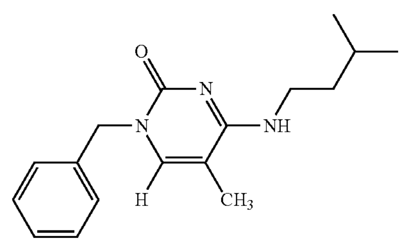 [SMILES: Cc1cn(Cc2ccccc2)c(=O)nc1NCCC(C)C] |
| PM3 | 1-benzyl-4-(cyclopentylamino)-5-methylpyrimidin-2(1H)-one | 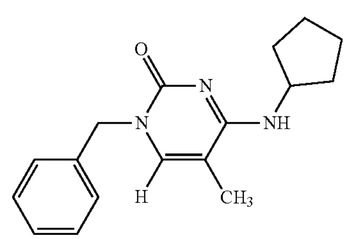 [SMILES: Cc1cn(Cc2ccccc2)c(=O)nc1NC1CCCC1] |
| PM4 | 1-benzyl-4-((3-(dimethylamino)propyl)amino)-5-methylpyrimidin-2(1H)-one | 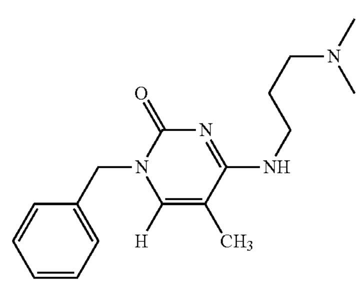 [SMILES: Cc1cn(Cc2ccccc2)c(=O)nc1NCCCN(C)C] |

-continued

| Compound No. | Chemical name | Chemical structure |
| --- | --- | --- |
| PM5 | 1-benzyl-4-(benzylamino)-5-methylpyrimidin-2(1H)-one | 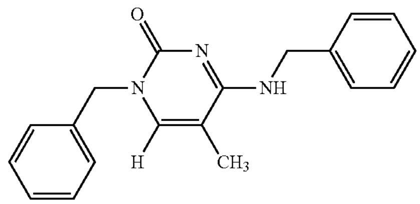 [SMILES: Cc1cn(Cc2ccccc2)c(=O)nc1NCc1ccccc1] |
| PM6 | 1-benzyl-5-methyl-4-(octylamino)pyrimidin-2(1H)-one | 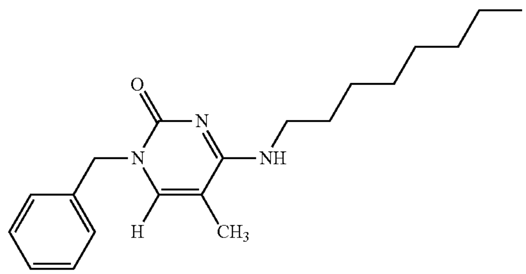 [SMILES: CCCCCCCCNc1nc(=O)n(Cc2ccccc2)cc1C] |
| PM7 | 5-methyl-1-(4-nitrobenzyl)-4-(octylamino)pyrimidin-2(1H)-one | 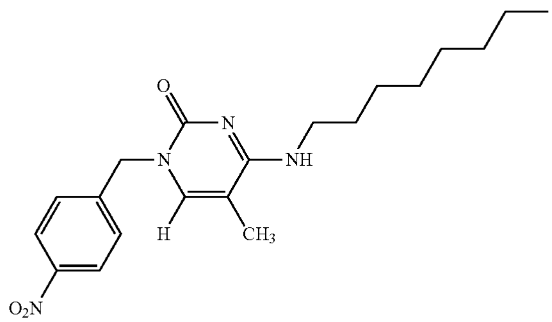 [SMILES: CCCCCCCCNc1nc(=O)n(Cc2ccc([N+](=O)[O-])cc2)cc1C] |
| PM8 | 5-methyl-1-(naphthalen-2-ylmethyl)-4-(octylamino)pyrimidin-2(1H)-one | 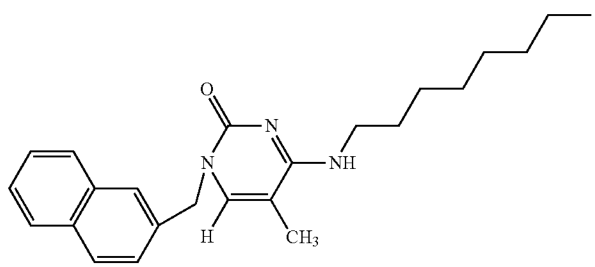 [SMILES: CCCCCCCCNc1nc(=O)n(Cc2ccc3ccccc3c2)cc1C] |
| PM9 | 5-methyl-4-(octylamino)-1-(4-(trifluoromethyl)benzyl)pyrimidin-2(1H)-one | 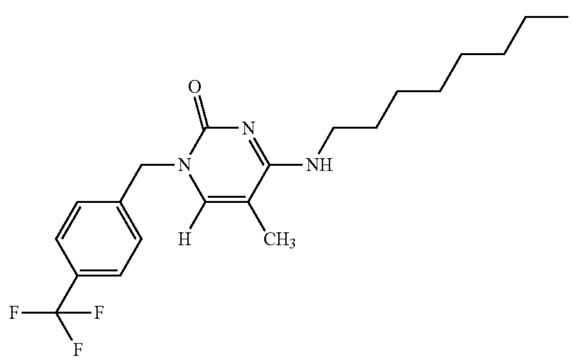 [SMILES: CCCCCCCCNc1nc(=O)n(Cc2ccc(C(F)(F)F)cc2)cc1C] |

| Compound No. | Chemical name | Chemical structure |
|---|---|---|
| PM10 | 1-benzyl-4-(decylamino)-5-methylpyrimidin-2(1H)-one | 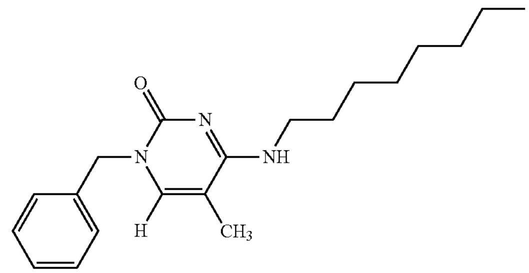 [SMILES: CCCCCCCCNc1nc(=O)n(Cc2ccccc2)cc1C] |

Pharmaceutical Compositions

In an aspect of some embodiments of the present disclosure, a pharmaceutical composition is provided, comprising one or more decoy peptides as defined herein and, optionally, a pharmaceutically acceptable carrier.

The terms "pharmaceutical composition" and "formulation" as used herein are interchangeable and refer to a medicinal preparation which encompasses a mixture of different components, including one or more active agents, which are accountable for a desired biological effect (e.g., one or more medicinally active agents) combined in a certain way, i.e., according to a particular formula, so as to be applicable for administration to a subject, e.g., a human subject. A formulation may be formulated together with one or more pharmaceutically or physiologically acceptable or suitable carriers so that it can be administered in a specific form, such as, but not limited to, a tablet, linctus, ointment, infusion or injection. The formulation may comprise excipients, stabilizers, solid and/or non-solid, e.g., liquid, gel, semi-solid (e.g., gel, wax) or gas components.

In the context of embodiment described herein, a disclosed formulation essentially comprises at least one decoy peptide as defined and disclosed herein, for example, one or more peptides or peptidomimetics such as any one or more of SEQ ID NOs:1-24, and/or one or more compound of formula (I) as defined herein, or a pharmaceutically acceptable salt thereof.

In some embodiments, a disclosed pharmaceutical composition is for treatment, amelioration, prevention, mitigation and/or curing of sepsis and/or a condition secondary to cardiovascular disease or disorder such as cardiac failure and myocardial infarction. In accordance with these embodiments, a contemplated pharmaceutical composition may further comprise at least one additional therapeutic agent useful for treatment of the indicated diseases and conditions, such as anti-inflammatory agents, antibiotics and the like.

As used herein, the terms "pharmaceutically acceptable", "pharmacologically acceptable" and "physiologically acceptable" are interchangeable and mean approved by a regulatory agency of the Federal or a state government or listed in the U.S. Pharmacopeia or other generally recognized pharmacopeia for use in animals, and more particularly in humans. These terms include formulations, molecular entities, and compositions that do not produce an adverse, allergic or other untoward reaction when administered to an animal, or a human, as appropriate. For human administration, preparations should meet sterility, pyrogenicity, general safety and purity standards as required by, e.g., the U.S. Food and Drug Administration (FDA) agency, and the European Medicines Agency (EMA).

Herein, the term "physiologically acceptable carrier" refers to an approved carrier or a diluent that does not cause significant irritation to an organism and does not abrogate the biological activity and properties of an active agent. Physiologically suitable carriers encompass any and all solvents and dispersion media that are physiologically compatible and approved for use in animals, and more particularly in humans. Examples of pharmaceutically acceptable carriers include water, saline, phosphate buffered saline, dextrose, glycerol, ethanol and the like, as well as combinations thereof.

Herein the term "excipient" refers to an inert substance added to a pharmaceutical composition or formulation to further facilitate process and administration of the active ingredients. "Pharmaceutically acceptable excipients", as used herein, encompass approved stabilizers that provide stabilization to the active agent(s) and optionally protect it against breakdown (e.g., hydrolysis) before it reaches its end target; preservatives; antioxidants (e.g., ascorbic acid (vitamin C) or a salt thereof; cysteine or a cysteine derivative, lipoic acid, uric acid, carotenes, α-tocopherol (vitamin E), and ubiquinol (coenzyme Q)); surfactants (e.g., Tween®-20, Tween®-40, Tween®-60 and Tween®-80); a buffer (e.g., histidine buffer, acetate buffer, sodium acetate buffer, sodium succinate buffer, sodium citrate buffer, sodium phosphate or potassium phosphate buffer, Tris buffer, sodium hydroxide buffer, or a mixture thereof); coatings; isotonic agents; absorption delaying agents; inert diluents (e.g., calcium carbonate, sodium carbonate, lactose, calcium phosphate, or sodium phosphate); lubricating agents (e.g., magnesium stearate, stearic acid, or talc); glidants; disintegrants; coloring agents; flavors, bulking agents (e.g. mannitol); local anesthetics; enhancers (e.g., pyrrolidones such as N-methyl-2-pyrrolidone (NMP) or polyvinyl alcohol (PVP), polyols, glycerol, lauroglycol, propylene glycol, diethylene glycol monoethyl ether, and/or propylene glycol monocaprylate); thickening agents (e.g., cellulose polymers such as hydroxypropyl cellulose, and/or carbomer polymers and derivatives, e.g., polysaccharides (agarose) polyacrylic polymers, poloxamers, and mixtures thereof); terpenes (non-aromatic compounds found in essential oils, which may be extracted from flowers, fruits, and other natural products. For example, d-limonene, dipentene (d/l-limonene), α-pinene, γ-terpinene, β-mircene, p-cimene, α-pinene, α-phellandrene, citronellolio, geraniale (citrale), nerol, beta-carotene, menthol, geraniol, farnesol, phytol and the like); various sugars and types of starch; vegetable oils; granulating and disintegrating agents (e.g., corn starch or alginic acid); binding agents (e.g., starch, gelatin or acacia); fillers (e.g., methylcellulose or sodium carboxymethyl cellulose); organic solvents; and suitable propellants (for aerosol spray formulation, e.g., dichlorodifluoromethane, trichlorofluoromethane, dichlorotetrafluoroethane or carbon dioxide) and any combination thereof, that are compatible with pharmaceutical administration, do not cause significant irritation to an organism and do not abrogate the biological activity and properties of a possible active agent. The use of such media and agents in combination with pharmaceutically active agents is well known in the art.

In some embodiments, a contemplated pharmaceutical composition comprises one or more peptide or peptidomimetic designated by SEQ ID NOs: 1-24 and presented in Table 1 herein.

For example, a contemplated pharmaceutical composition may comprise a peptide or peptidomimetic of SEQ ID NO:1, SEQ ID NO:2, SEQ ID NO:8, SEQ ID NO:9, SEQ ID NO:11, SEQ ID NO:12, SEQ ID NO:13, SEQ ID NO:14 and/or SEQ ID NO: 16, or a pharmaceutically acceptable salt thereof.

In some embodiments, a contemplated pharmaceutical composition comprises a compound of formula (I):

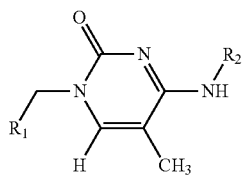

a stereoisomer, enantiomer or pharmaceutically acceptable salt thereof, wherein
$R_1$ and $R_2$ each independently is H, alkyl, alkenyl, alkynyl, cycloalkyl, heteroalicyclyl, aryl, heteroaryl, haloalkyl, nitro and/or amino group, as defined herein.

In some embodiments, $R_1$ is phenyl or naphthyl, optionally substituted by a haloalkyl group or a nitro group.

In some embodiments, $R_2$ is selected from a linear or branched alkyl, optionally substituted with one or more phenyl or amino groups, a cycloalkyl, heteroalicyclic group, aryl or heteroaryl group optionally substituted with one or more of any of the optional substituents as defined herein.

In some embodiments, a disclosed pharmaceutical composition may comprise one or more of the compounds PM1-PM10 as defined herein and presented in Table 2, a stereoisomer, enantiomer or pharmaceutical acceptable salt thereof.

In exemplary embodiments, a contemplated formulation comprises compound PM6 and/or a pharmaceutically acceptable salt thereof.

In some embodiments, a contemplated pharmaceutical composition may comprise one or more peptides or peptidomimetics designated by SEQ ID NOs:1-25 and one or more compounds represented by formula (I).

For example, a contemplated formulation may comprise one or more peptides or peptidomimetics of SEQ ID NOs: 1, 2, 8, 9, 11, 12, 13, 14, and/or 16, and compounds PM2 and/or PM6.

A disclosed pharmaceutical composition comprising decoy peptides may be used in the treatment of a disease and/or disorder which may be treated or prevented by inhibition of a signaling pathway induced by TLR4.

In some embodiments, a contemplated pharmaceutical composition may comprise, besides at least one of the decoy peptides disclosed herein, which may be referred to as "prime active agents" or "main active agents", additional active agents, herein designated "secondary active agents", that include, for example, additional TLR4 activity modulators (e.g., inhibitors) and/or drugs applied for treatment of, for example, cardiovascular diseases, inflammation and/or sepsis. Non-limiting examples of additional TLR4 activity modulators include known decoy peptides derived from the TRAM TIR domain, for example, the peptide IVFAEMPCG (herein designated by SEQ ID NO: 25) as well as other peptides and peptidomimetics disclosed, for example, in Piao et al., 2013 (supra), incorporated herein by reference as if fully described herein. Nutraceuticals and dietary factors that reduce TLR activation are also contemplated such as Curcurmin (tumeric), Cinnamaldehyde (cinnamon), Sulforaphane (broccoli), and Resveratrol.

Non-limiting examples of active agent or drugs for treatment of cardiovascular diseases, inflammation and/or sepsis that may be combined with the decoy peptides disclosed herein are antibiotics; blood diluters and antiplatelet agents such as aspirin and clopidogrel; renin-angiotensin-aldosterone system (RAAS) blockers such as lisinopril, losartan and eplerenone; beta-blockers (also called beta-adrenergic blocking agents) such as metoprolol; statins such as atorvastatin; or any of the known drugs provided for treating a cardiovascular disease or disorder and/or sepsis or inflammation associated with e.g., thrombolytic therapy, reperfusion therapy and/or percutaneous coronary intervention.

The term "cardiovascular disease (CVD)", as referred to herein and in the art, is a class of diseases that involve the heart or blood vessels. Cardiovascular disease includes coronary artery diseases such as angina and myocardial infarction (commonly known as a heart attack). Other CVDs include stroke, heart failure, hypertensive heart disease, rheumatic heart disease, cardiomyopathy, heart arrhythmia, congenital heart disease, valvular heart disease, myocarditis, aortic aneurysms, peripheral artery disease, thromboembolic disease, and venous thrombosis.

In some embodiments, a pharmaceutical composition disclosed herein is useful for the treatment of sepsis.

The term "sepsis", as used herein, refers to the life-threatening condition caused by an immune response triggered by an infection wherein the body's response to the infection causes injury to its own tissues and organs. Most commonly, the infection is bacterial, but it may also be from fungi, viruses, or parasites. Common locations for the primary infection include lungs, brain, urinary tract, skin, and abdominal organs. Risk factors include young or old age, a weakened immune system from conditions such as cancer or diabetes, major trauma, or burns. Sepsis may be diagnosed based on at least two of the following: increased breathing rate, change in level of consciousness, and low blood pressure. Other common signs and symptoms include fever, increased heart rate and confusion. There also may be symptoms related to a specific infection, such as a cough with pneumonia, or painful urination with kidney infection. Severe sepsis is sepsis causing poor organ function or insufficient blood flow. Insufficient blood flow may be evident by low blood pressure, high blood lactate, or low urine output. Septic shock is a low blood pressure due to sepsis that does not improve after reasonable amounts of intravenous fluids are given.

A pharmaceutical composition, in accordance with some embodiments described herein, may comprise from about 0.1% to about 99% w/w of one or more decoy peptides as provided herein. For example, from about 0.5% to about 1.0%, 1.0% to about 5.0%, 2.0% to about 5.5%, 4.0% to about 7.0%, 5.0% to about 8.0%, 6.5% to about 9.0%, 8.5% to about 15.0%, 10.0% to about 20.0%, 15.5% to about 25.0%, 20.5% to about 35.0%, 30% to about 40.0%, 35.5% to about 50.0%, 40.0% to about 60.0%, 50.0% to about 65.0%, 60.0% to about 70.0%, 65.0% to about 75.0%, 70.0% to about 80.0%, 75.5% to about 85.0%, 80.0% to about 90.0%, or 85% to about 98.0%, and any sub-ranges therebetween.

When a contemplated pharmaceutical composition comprises more than one decoy peptide, or comprises one or more decoy peptides and one or more secondary active agents, it may be formulated as a single unit dosage from (namely, all active agents are combined in a single formulation), or, alternatively, it can be formulated as a plurality of unit dosage forms (namely, at least some of the active agents are formulated in separate pharmaceutical compositions). For example, a contemplated formulation may comprise two or more dosage unit forms, at least one comprising one or more of a first active agent (e.g., a decoy peptide, for example a compound of formula (I) or a peptide or peptidomimetic of any of SEQ ID NOs:1-24), and at least one comprising a secondary active agent (e.g., antibiotics or a blood diluter).

The compositions provided herein may be in a variety of forms. These include, for example, liquid solution (e.g., injectable and infusible solutions, syrups), gels, creams, solids (e.g., powders, tablets, troches, suppositories), films, emulsions, dispersions or suspensions, hard or soft-shell gelatin capsule, capsules, liposomes, lyophylisate and aerosol. The selected form depends on the intended mode of administration and therapeutic application. Any one of these forms may be prepared according to any method known in the art for the manufacture of pharmaceutical compositions.

In some embodiments, the compositions are in the form of injectable or infusible solutions. In some embodiments, a contemplated formulation is designed for oral administration, and is formulated as tablets, pills, dragees, capsules, liquids, gels, syrups, slurries, suspensions, and the like.

For example, a contemplated pharmaceutical composition may be formulated as a liquid, for example, aqueous formulation. When the pharmaceutical compositions comprise a plurality of dosage unit forms, for example two dosage unit forms, they can be formulated in different forms. For example, a first unit dosage form comprising, e.g. a decoy peptide, may be formulated as a liquid formulation (e.g., aqueous formulation), and the second unit dosage form comprising, e.g., a second active agent may be formulated as a solid formulation.

Disclosed pharmaceutical compositions may be formulated for any suitable route of administration, e.g., for subcutaneous, transdermal, intradermal, transmucosal, intravenous, intraarterial, intramuscular, intraperitoneal, intratracheal, intrathecal, intraduodenal, intrapleural, intranasal, sublingual, buccal, intestinal, intraduodenally, rectal, intraocular, or oral administration. The compositions may also be formulated for inhalation, or for direct absorption through mucous membrane tissues.

When the pharmaceutical composition comprises a plurality of dosage unit forms, for example two dosage unit forms, they can be administered in different routes. For example, a first unit dosage form, comprising e.g., a decoy peptide as described herein may be administered intravenously as a liquid formulation, and a second unit dosage form comprising e.g., antibiotics, can be administered orally as a tablet.

Also contemplated herein is a stable lyophilized powder comprising a decoy peptide as defined herein, which can be reconstituted into a liquid formulation by addition of water with or without excipients such as antioxidants, surfactants and the like.

The term "physiologically acceptable pH" is understood to mean a pH of, e.g., a formulation or composition that facilitates administration of the formulation or composition to a patient without significant adverse effects, e.g., a pH of about 4 to about 9.8 (for example, about 4±0.3 to about 9.5±0.3).

"Ambient temperature", also referred to herein as "room temperature" (RT), as understood by a person of skill in the art, refers to a temperature of from about 10° C. to about 30° C. In exemplary embodiments, ambient temperature can be 25° C.

Methods of Treatment

Chronic activation of the immune system may benefit from TLR4 inhibition. TLR4 over activation has been reported to play a potent role in sepsis, Rheumatoid arthritis, psoriasis, asthma, and the like. The present inventors have previously shown that there is a continues TLR4 activation leading to higher TNFα secretion in patients with coronary artery disease (Avlas, *PLoS One.*, 2015). Hence, inhibiting TLR4 signaling may prevent the onset of these diseases.

In an aspect of the disclosure, provided herein is a method of treating a subject inflicted with a disease or disorder associated with induction of a TLR4 signaling pathway, comprising administering to the subject a therapeutically effective amount of a TLR4 inhibitor and/or a formulation comprising same, thereby treating the subject.

As used herein, the phrase "disease or disorder associated with induction of a TLR4 signaling pathway" refers to a disease or disorder that is associated with, related to, and/or caused by activation of TLR4. Non-limiting examples of disease and disorders associated with TLR4-induced signaling pathway are diseases and disorders secondary to cardiovascular diseases (CVDs), sepsis, and inflammatory diseases. Further diseases or disorders associated with TLR4-induced signaling pathway include neurodegenerative disorders such as Alzheimer's disease, amyotrophic lateral sclerosis, multiple sclerosis and Parkinson's disease, and liver diseases such as liver fibrosis, and hepatocellular carcinoma. TLR4 signaling is also associated with atherosclerotic plaque progression and destabilization, probably by promoting vascular inflammation under the influence of oxidized low-density lipoprotein. It has been demonstrated that the expression and activity of TLR4 are increased in monocytes of patients with metabolic syndrome, which contributes to an increased risk for diabetes and CVD. Additionally, obesity is associated with an enhanced TLR4 response in patients suffering from established atherosclerotic disease.

In some embodiments, the disease and disorder associated with TLR4-induced signaling pathway is secondary to a cardiovascular disease or disorder such as, but not limited to, myocardial infarction or angina.

"Secondary disease or disorder", as referred to herein, is a disease or disorder that follows or results from, a sequela of, or a complication of an earlier disease, injury, or event, i.e., a morbid condition subsequent to, or a consequence of another disease. A secondary disease or disorder may be manifested by secondary symptoms of the prime disease or disorder, for example, complications of primary symptoms that have the potential to be more troublesome or severe than the problem from which they stem. Although secondary symptoms can develop at any time, they are more likely if primary symptoms are not well managed.

A disease or disorder secondary to a cardiovascular disease may result, for example, form activation of the immune system, for example, following release of pathogen-associated microbial patterns (PAMPs) such as LPS, or release of danger-associated molecular patterns (DAMPs) such as heat shock proteins, high mobility group box 1 protein (HMGB1), or cytokines released actively or passively from injured cells (e.g. IL-1α), which are associated with, or caused by, e.g., cardiac failure, MI, ischemia and the like. Non-limiting examples of disease or disorder secondary to CVD include inflammation, infection, sepsis, kidney failure, leg's edema or lung's edema.

In some embodiments, the disease and disorder associated with TLR4-induced signaling pathway is sepsis, which may result, for example, form activation of the immune system, for example, in response of PAMPs such as LPS, or bacterial or viral infection.

In some embodiments the TLR4 inhibitor interferes with binding to a TIR domain of TLR4 and inhibits a TLR4-induced signaling pathway. In exemplary embodiments, a TLR4 inhibitor used in a contemplated method is a decoy peptide, particularly, any one or more of the decoy peptides contemplated herein or a pharmaceutical composition comprising same.

For example, the decoy peptide may be a peptide or peptidomimetic of SEQ ID NO:1, 2, 3, 4, 5, 6, 7, 8, 9, 10, 11, 12, 13, 14, 15, 16, 17, 18, 19, 20, 21, 22, 23 and/or 24, or a compound of formula (I), for example compound PM1, PM2, PM3, PM4, PM5, PM6, PM7, PM8, PM9 and/or PM10.

In exemplary embodiments, the decoy peptide employed in a contemplated method is designated by SEQ ID NOs:1, 2, 8, 9, 11, 12, 13, 14 or 16.

In exemplary embodiments, the decoy peptide provided to a subject in need thereof, in accordance with a contemplated method, is compound PM6.

Treating a disease, as referred to herein, means ameliorating, inhibiting the progression of, delaying worsening of, and even completely preventing the development of a disease, for example inhibiting the development of cardiac tissue damage or inhibiting the development of sepsis in a person who has a cardiovascular disease or disorder, or inflammation. Treatment refers to a therapeutic intervention that ameliorates a sign or symptom of a disease or a pathological condition after it has begun to develop. In particular examples, however, treatment is similar to prevention, except that instead of complete inhibition, the development, progression or relapse of the disease is inhibited or slowed.

An effective amount of a compound, for example, of a compound of formula (I) herein or a pharmaceutically acceptable salt thereof, or of peptides or peptidomimetics of SEQ ID NOs: 1-24 or a pharmaceutically acceptable salt thereof, is a quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

"Administration" as referred to herein is introduction of the active agent, e.g., a decoy peptide described herein, or a pharmaceutical composition comprising same into a subject by a chosen route. Administration can be local or systemic. Examples of local administration include, but are not limited to, topical administration, subcutaneous administration, intramuscular administration, or administration to the nasal mucosa or lungs by inhalational administration, intravitreal administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Systemic administration includes any route of administration designed to distribute an active compound or composition widely throughout the body via the circulatory system. Thus, systemic administration includes, but is not limited to intra-arterial and intravenous administration, oral administration, topical administration, subcutaneous administration, intramuscular administration, or administration by inhalation, when such administration is directed at absorption and distribution throughout the body by the circulatory system.

In some embodiments, a contemplated decoy peptide or a formulation comprising it may be administered continuously, for example by a designated pump. Alternatively, or additionally, a contemplated decoy peptide or a formulation comprising same may be administered non-continuously, e.g., as bolus injection, a pill taken orally or eye drops. In some embodiments, administration includes acute and immediate administration such as inhalation or injection.

In some embodiments, a particular dosage form may be administered by two or more different routes, for example, both intravenously and orally either simultaneously of subsequently.

The term "subject" as used herein encompasses human and non-human mammals (e.g., dog, cats, monkeys, horses, cows, rats, rabbits etc.).

Kits

An aspect of the disclosure is related to a kit for carrying out one of the methods contemplated herein for treatment of a disease or disorder associated with induction of a TLR4 signaling pathway, the kit comprising one or more of: (a) at least one decoy peptide as defined herein and/or a pharmaceutical composition comprising same; (b) reagents and means for applying the kit, e.g., administrating a decoy peptide to a subject; and (c) instructions for use. A non-limiting list of means for applying the decoy peptides includes syringes, needles such as blood collection needles, sample tubes, and any other device necessary for administering a drug as known to the man skilled in the art.

In some embodiments, a contemplated kit is useful for treating a disease or disorder selected from a cardiovascular secondary disease or disorder, sepsis or inflammation.

It is to be understood that the present disclosure is not necessarily limited in its application to the details set forth in the description above or exemplified by the Examples herein. The invention is capable of other embodiments or of being practiced or carried out in various ways.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments described in the present disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It is appreciated that certain features of the present disclosure, which are, for clarity, described in the context of separate embodiments, may also be provided in combination in a single embodiment. Conversely, various features of the present disclosure, which are, for brevity, described in the context of a single embodiment, may also be provided separately or in any suitable subcombination or as suitable in any other embodiment described herein.

Various embodiments and aspects of the present disclosure as delineated hereinabove and as claimed in the claims section below find experimental support in the following examples.

EXAMPLES

Reference is now made to the following examples, which together with the above descriptions illustrate some embodiments of the disclosure in a non-limiting fashion.

Generally, the nomenclature used herein and the laboratory procedures utilized in the present disclosure include molecular, chemical and/or biochemical. Such techniques are thoroughly explained in the literature. Other general references are provided throughout this document. The procedures therein are believed to be well known in the art and are provided for the convenience of the reader. All the information contained therein is incorporated herein by reference.

Materials and Methods

Materials. Commercially available reagents and solvents were purchased from several companies: Sigma-Aldrich®, Holand-Moran (Yehud, Israel), Acros Organic™ (New Jersey, USA), Alfa Aesar® (Massachusetts, USA), Bio-Lab Ltd. (Jerusalem, Israel), Merck (Herzliya Pituach, Israel) and Chania Peptides (Shanghai, China), and were used without additional purification.

Peptide Synthesis (i) Rink Resin-Based Solid-State Peptide Synthesis

Peptide and peptidomimetics were synthesized by solid phase Fmoc strategy as generally practiced in the art. Specifically, 4-((2,4-dimethoxyphenyl)(Fmoc-amino) methyl) phenoxyalkyl functionalized supports known as Rink amid (RAM) resins useful in the synthesis of peptide carboxamides were used. Detachment of peptide amides from these supports was achieved by treatment with 95% trifluoroacetic acid (TFA). The C-terminal amino acid residue was coupled using standard amide-forming procedures. Synthesis was performed using 0.40 mmol RAM resin (0.52 mmol/gr loading). The resin, after being shaken for 30 min at room temperature (RT), was loaded with the first amino acid of a desired peptide (5 eq) using hexafluorophosphate benzotriazole tetramethyl uronium (HBTU) as a coupling reagent (480 mg/1.25 mmol), and N,N-diisopropylethylamine (DIEA) (0.22 ml/1.25 mmol), and was shaken at RT for further 2 h. Coupling yield was verified by a ninhydrin test performed after each coupling set ($\alpha$-amino acids react with ninhydrin to give a coloured product, which is useful both qualitatively (e.g. for chromatography) and quantitatively for peptide sequencing). Fmoc protecting groups were removed by treatment with a 20% piperidine/dimethylformamide (DMF) solution for 20 min. The next amino acids in the sequence (5 eq each) were coupled using HBTU (480 mg/1.25 mmol) and DIEA (0.22 ml/1.25 mmol) while shaking at RT for 1 h. Finally, removal of protecting groups such as Z-butyloxycarbonyl (Boc), Z-butylester (OtBu) or triphenyl (Trf), and release of the peptides were carried out by using a solution containing 95% TFA, 2.5% isopropanolsilane and 2.5% $H_2O$. During synthesis, mass spectra (MS) was utilized to verify that the desired compounds were obtained. All peptides were purified using preparative HPLC and characterized by additional MS.

In the synthesis of peptides of SEQ ID NOs: 15-17 and 24, the last, non-natural amino acid at the C-terminus was added while the forming sequence was still conjugated to the Rink amide resin. Multiple washing steps with DMF (4×2.0 ml) and dichloromethane (DCM) (3×2.0 ml) were applied after conjugating the last, non-natural amino acid. Following deprotection of this amino acid, bromoacetic acid (695 mg/4 ml DMF) and N,N'-diisopropylcarbodiimide (DIC) (0.78 ml) in DMF were added, and the mixture was shaken at RT for 2 h. Deprotection and the release of the crude peptide were carried out as described above.

(ii) N-Terminus Acetylation

Acetic anhydride (1.9 ml), DIEA (0.9 ml), 1 M hydroxybenzotriazole (HOBt) in N-methyl-2-pyrrolidone (NMP) solution (0.6 ml), and an additional 6.6 ml of NMP were mixed in a flask to obtain an acetylene solution.

The Fmoc-protecting group was removed from the N-terminus by a 20% piperidine/DMF solution. The degree of deprotection was evaluated by a ninhydrin test. Next, 5 ml of the acetylating solution was added to the solid-state synthesis mixture and it was shaken for 30 min at RT. This procedure was repeated with another 5 ml of the acetylation mix. Then, other protecting groups were removed as described above, and the crude peptides were released from the resin In Vitro Assays (i) Cell Culture Rat hearts (1-2 days old) were removed under sterile conditions and washed three times in phosphate-buffered saline (PBS) to remove excess blood cells. The hearts were minced and then gently agitated in RBD (a solution of proteolytic enzymes (Biological Institute, Ness-Ziona, Israel) prepared from fig tree extract, and diluted 1:100 in $Ca^{2+}$- and $Mg^{2+}$-free PBS) for a few cycles of 10 min each. Dulbecco's modified Eagle's medium (Biological Industries, Kibbutz Beit Haemek, Israel) containing 10% horse serum was added to supernatant suspensions containing the dissociated cells. The mixture was centrifuged at 1400 rpm for 4 min. The supernatant phase was discarded, and the cells were re-suspended. The cell suspension was diluted to $1.0\times10^6$ cells/ml, unless stated otherwise, and 1.5 ml of the suspension was placed in 35-mm plastic culture dishes collagen- or gelatin-coated, or on coated cover glasses. The cultures were incubated in a humidified atmosphere of 5%

$CO_2$ and 95% air at 37° C. Confluent monolayer exhibiting spontaneous contractions were developed in the culture within 2 days.

(ii) Hypoxia

Using a vacuum pump, the oxygen rich air was evacuated from an incubator containing plates with cell cultures, and a 100% Argon atmosphere was let in, while maintaining a temperature of 37° C. The cell cultures were washed with PBS twice to remove glucose from the medium. Hypoxic treated cells were cultures in PBS without glucose. These cells lasted for 180 minutes.

(iii) Creatine Kinase (CK) and Lactate Dehydrogenase (LDH) Assay

Primary human cardiac myocytes (HCM) are isolated from the ventricles of the adult heart. They are qualified for in vitro research on cardiac diseases and for pharmacological studies. Their specialized high-oxygen-content with a large number of mitochondria contributes to the major role of cardiac muscles in the heart's rhythmic pumping. Initially, the HCM act more like progenitor cells in that they are not yet fully differentiated. When they are grown to confluency and cultivated for an extended period of time, the differentiation process begins.

Primary cardiomyocytes which were obtained by method described above, were treated with exemplary decoy peptides described herein. After 30 minutes of incubation, sepsis like (LPS treatment for 6 hours), or myocardial infarction (MI) like (hypoxia for 3 hours) conditions were imposed to measure the release of CK and LDH to the medium and determine the potential cardioprotective effect of the tested decoy peptides. Cytotoxicity and level of cell damage were assessed by spectrophotometric measurement of lactate dehydrogenase (LDH) and creatine kinase (CK) activities (at 30° C.). Results are presented as CK and LDH release in arbitrary units (a.u.)

Activity of LDH and CK was determined in the cell-culture medium (25 μl) transferred into 96-well plates, using commercial L-LDH/CK kits (such as those manufactured, e.g., by Sigma-Aldrich, BioVision™ or Thermo Fisher Scientific®).

Lactate dehydrogenase is an oxidoreductase which catalyzes the interconversion of lactate and pyruvate. When disease or injury affects tissues containing LDH, the cells release LDH into the bloodstream, where it is identified in higher than normal levels. As LDH is a fairly stable enzyme, the LDH assay is widely used as a marker for damage to cells and tissues, i.e., to measure damage that is severe enough to allow LDH to leak from the cell. In some LDH assay protocols, LDH reduces nicotinamide adenine dinucleotide (NAD) to NADH, which then interacts with a specific probe to produce a color (for example, reduction of the tetrazolium salt MTT in a NADH-coupled enzymatic reaction to a reduced form of MTT which exhibits an absorption maximum at 565 nm). A kit can detect 1-100 mμ/mL of LDH directly in samples. When NADH is the compound being measured in the assay, the level of this compound being produces (as observed by optical density at 340 nm) is indicative of, or corresponds to, elevated LDH release to the medium.

Creatine kinase is widely expressed in various tissues and cell types, with highest activity in striated muscles, heart tissue and brain. Increased CK level is associated with many diseases such as myocardial infarction, muscular dystrophy, pulmonary infarction and brain tumors. In the creatine kinase assay protocol, CK converts creatine and ATP into phosphocreatine and ADP, respectively. In an exemplary assay/kit, the phosphocreatine and ADP are allowed to react with the CK enzyme mix to form an intermediate, which reduces a colorless probe to a colored product with strong absorbance (e.g., at $\lambda=450$ nm).

(iv) Mononuclear Cells Isolation

Density gradients are often used in a Ficoll-Hypaque method for the isolation of mononuclear cells (MNCs) from peripheral blood, cord blood, and bone marrow by exploiting differences in cell density. Mononuclear cells include all blood cells with a single nucleus. There are two main types of white blood mononuclear cells: lymphocytes and monocytes, and 5 key subtypes within these two main categories. Monocytes are the largest of the white cells and are formed in the bone marrow. Half are stored in the spleen and the other half migrate to the bloodstream and then into other tissues, where they mature into macrophages (typically about 24 hours after release into the bloodstream).

Differences in cell density are exploited in density gradient-based isolation to separate granulocytes and erythrocytes from MNCs. Granulocytes and erythrocytes have a higher density at the osmotic pressure of an applied density gradients medium such as Lymphoprep™ or Ficoll-Paque™ and sediment through the gradient layer during centrifugation. The polysaccharide, e.g., in Lymphoprep™, enhances erythrocyte aggregation, thereby increasing erythrocyte sedimentation. Mononuclear cells such as monocytes, with lower densities, remain at the plasma:Lymphoprep™ interface.

Peripheral blood (20 ml) was obtained from one person for isolation of MNCs. Peripheral blood mononuclear cells (PBMCs) were isolated by density gradient centrifugation over density gradient medium Ficoll-Paque™ or Lymphoprep™ (STEMCELL™ Technologies, Canada). The blood was centrifuged for 40 minutes at 800 g with a 20-minute brake time. During centrifugation, erythrocytes and granulocytes were aggregated and rapidly settled to the bottom of the tube; lymphocytes and monocytes, collectively referred to herein as "white blood cells" (WSCs) remained at the plasma:Lymphoprep™. The layer of WBC was collected with a 10 ml pipet by moving the pipet in a circular motion around the inside of the tube just below the surface of the plasma layer. The WBCs were transferred to another tube and 5 ml of PBS was added. The WBC/PBS mixture was centrifuged for 10 min at 1200 rpm and the PBS was discarded. The pellet was then suspended in 3 ml of PBS with 2% FBS.

(v) Real-time quantification of mRNA

Gene expression was determined using the real-time reverse transcriptase polymerase chain reaction (RT-qPCR) method previously described (see, for example, Real-Time PCR an essential guide, K. Edwards, et al., ed., Horizon Bioscience, 2004).

PCR, in all of its forms, is an amplification technique which enables to increase the number of copies of a nucleic acid molecule in a sample or specimen. Basically, a biological sample collected from a subject is contacted with a pair of oligonucleotide primers under conditions that allow for the hybridization of the primers to nucleic acid template in the sample. The primers are extended under suitable conditions with a specific polymerase enzyme, dissociated from the template, and then re-annealed, extended, and dissociate so as to amplify the number of copies of the nucleic acid. Hence, DNA is amplified by 3 repeating steps, each step being effected at a distinct temperature range (each PCR cycle is also referred to as a "thermal cycle"): denaturation, annealing and elongation. The product of in vitro amplification can be characterized by electrophoresis, restriction endonuclease cleavage patterns, oligonucleotide hybridization or ligation, and/or nucleic acid sequencing, using standard techniques.

Real time PCR also termed herein "quantitative PCR" or "qPCR" is a method for detecting, characterizing and quantifying DNA products generated during each cycle of a PCR amplification, which products are proportionate to the amount of template nucleic acid present prior to the start of PCR. The information obtained, such as an amplification curve, is used for quantitating the initial amounts of template nucleic acid sequences. Real-time PCR combines PCR amplification and detection into a single step. As in standard PCR, DNA is amplified by 3 repeating thermal cycles, however, in qPCR, fluorescent dyes are used to label PCR products during thermal cycling, whereby during each cycle the fluorescence is measured, enabling the collection of data as PCR progresses. The cycle threshold (Ct) is defined as the number of cycles required for the fluorescent signal to cross a threshold (i.e., exceed background level). Ct levels are inversely proportional to the amount of target nucleic acid in the sample, i.e., the lower the Ct level, the greater the amount of target nucleic acid in the sample, wherein Cts<29 are strong positive reactions indicative of abundant target nucleic acid in the sample. A "delta-Ct", as referred to herein, is the difference between Ct specific to the sequence of interest and Ct of a reference sequence, usually the sequence of an abundant "housekeeping gene" which thus uses as a normalization means (particularly where the target sequence does not have the same concentration in all samples tested). The reference sequence, also referred to herein as "reference gene" may be one or more constantly expressed genes, for example, but not limited to, TATA-binding protein (TBP) or NONO (non-POU domain containing, octamer-binding). In exemplary embodiments, TBP gene serves as a reference gene and TBP mRNA is reverse transcribed and amplified. TATA-binding protein is a central eukaryotic transcription factor used by all three cellular RNA polymerases. Real-time PCR instruments measure the accumulation of fluorescent signal during the exponential phase of the reaction for fast, precise quantification of PCR products and objective data analysis.

Reverse transcription PCR (RT-PCR) allows the detection and amplification of RNA templates. The RNA is reverse transcribed into complementary DNA (cDNA), using reverse transcriptase. The first step of RT-PCR is the synthesis of a DNA/RNA hybrid. The single stranded DNA molecule is then completed by the DNA-dependent DNA polymerase activity of the reverse transcriptase into cDNA. Reverse transcriptase also has an RNase function, which degrades the RNA portion of the hybrid. From here on, the standard PCR procedure is employed to amplify the cDNA. The possibility to revert RNA into cDNA by RT-PCR has many advantages. Most commonly, it serves as a first step in qPCR, which quantifies RNA transcripts in a biological sample, and allows the detection of low abundance RNAs in a sample.

Quantitative reverse transcription PCR (RT-qPCR) also referred to herein as "real time RT-PCR", allows the real time detection, amplification and quantification of RNA templates. RNA is first transcribed into cDNA by reverse transcriptase from total RNA or messenger RNA (mRNA). The cDNA is then used as the template for the qPCR reaction as described above.

A primer is a short nucleic acid sequence that provides a starting point for DNA synthesis, namely, it serves to prime and lay a foundation for DNA synthesis by enzymes that synthesize DNA (i.e., DNA polymerases) that can only attach new DNA nucleotides to an existing strand of nucleotides in the presence of a primer. In in vitro studies, the primer is designed specifically for the DNA region of interest such that it matches the beginning of the DNA template or target to be amplified. After annealing to a target DNA, the primers are extended along the target DNA strand by a DNA polymerase enzyme, preferably a thermostable DNA polymerase such as the Taq polymerase (isolated from the heat-tolerant bacterium *Thermus aquaticus*). Two primers are used per amplified DNA in a PCR reaction, having sequences that promote their hybridization to opposite strands of the template DNA. These primers are interchangeably referred to herein as "primer pair" or "forward and reverse primers".

Real-time RT-PCR experiments were performed in duplicates on an ABI 7900 instrument (Applied Biosystems™) using Taqman™ Master Mix (Applied Biosystems™). The average threshold cycles (Ct) of the duplicates were used to calculate the relative expression levels of the following genes: TLR4 (Applied Biosystems™ assay primer ID: Mm00569848_m1 Tlr4), TLR2 (assay primer ID: Mm01769726_m1 Tlr2), TNF-α (assay primer ID: Mm00443260_g1 Tnf) and IL-1β (assay primer ID: Mm00434228_m1 Il1b) in vitro and in vivo following hypoxia or ischemia, respectively. The reference gene was TBP and the primer used was derived from mouse TATA-box binding protein (Applied Biosystems™ assay primer ID: Mm00446973_m1 Tbp). Amounts of TLR2, TLR4, TNF-α and IL-1β mRNAs in each sample were calculated relative to TBP mRNA, based on the corresponding Cts, as Relative Quantity (RQ) values, and normalized taking as 1 a randomly selected sample of the control group (TBP mRNA). Calculation were performed using the Applied Biosystems Analysis™ software (StepOnePlus V2.2.2). All mRNA scores are presented in arbitrary units.

(vi) Fluorescence Activated Cell Sorting (FACS)

Flow cytometry is an analytical cell-biology technique that utilizes light to count and profile cells in a heterogenous fluid mixture. Flow cytometry analysis was used to evaluate binding of antibodies to TLR4 presenting cells. In this assay, an anti-TLR4 antibody was added to a monocytes suspension and cells which bound the antibody were visualized by a fluorescently labeled secondary antibody that bound to the anti-TLR4 antibody (Ab). Accordingly, samples were first "labeled" with the anti-TLR4 antibody, then incubated with Fluor® 488 conjugated to a secondary Ab for TLR4 (CD284) positive cells visualization.

In order to confirm the specificity of binding, and further in order to correct for non-specific or background staining, isotypes control mouse IgGs were added to cell suspensions at the same concentration as the anti-TLR4 Abs. To deduct the non-specific or background staining from the positive staining due to direct Ab binding to the antigen, the level of background staining was assessed by the use of the same fluorochrome as that used for staining the anti-TLR4 Ab.

All cells were prepared for FACS analysis according to a routine procedure: for cell lines, floating cells were collected from the growth media by centrifugation; adherent cells were treated with trypsin to detach them from the surface of the growth dishes.

Peripheral blood (30 ml) was obtained for the isolation of monocytes. Monocytes were purified by density gradient centrifugation as described above, and/or by adherence to plastic in RPMI 1640 medium supplemented with 10% fetal bovine serum (FBS) and antibiotics. Peripheral blood mononuclear cells (PBMCs) ($10^6$ cells/ml) were first seeded into 24-well plates (0.5 ml per well), after 2 hours, non-adherent cells were removed by several washes with warm PBS.

Monocytes freshly isolated either by density gradient centrifugation by adherence differentiated into macrophages in complete RPMI 1640 medium supplemented with human recombinant macrophage colony stimulating factor (100 ng/ml) for 6 days. To confirm macrophage cell lineage, direct immunostaining was performed with an antibody directed against CD11b/mac1 (Biolegend® Inc., San Diego, Calif., USA). Eighty percent (80%) of positive staining was observed by flow cytometry analysis. The proportion of TLR4 in this separated cell fraction was examined by FACS analysis using, as isotype control, mouse IgG2a IsoControl (eBioscience™ #53-4724-80), and mouse anti-human CD284 Alexa Fluor® 488 Clone FITA125 secondary Ab (Isotype IgG2a. eBioscience™ #53-9917-41), which recognizes the human TLR4 (also known as CD284) cell surface antigen. Cells were analyzed in a BC Gallios Flow Cytometer (Beckman Coulter, Indianapolis Ind., USA) and were initially gated on the basis of forward and side scatter characteristics. Kaluza Software was used to analyze the results. Results are expressed as mean fluorescence intensity (MFI) and also as normalized to control.

(vii) Lysis and Sample Preparation, and Western Blot Analysis

Western blotting, also known as immunoblotting or protein blotting, is a core technique useful in separating and identifying proteins from a complex mixture of proteins extracted from cells. The term "blotting" refers to the transfer of a biological sample from a gel to a membrane and its subsequent detection on the surface of the membrane. The technique is based on three main steps: (1) separation of cell extract (or homogenate) proteins by molecular weight (and thus by type) through gel electrophoresis using agarose gel such as the stacking gel sodium dodecyl sulfate polyacrylamide gel electrophoresis (SDS-PAGE; has a lower acrylamide concentration making it a porous gel); (2) transfer to a solid support (membrane) which produces a band for each protein. The membrane may be nitrocellulose or polyvinylidene difluoride (PVDF); and (3) identifying specific desired proteins by incubation of the membrane with antibodies specific to the proteins of interest (herein "primary antibodies"), and labelling the antibodies by the use of secondary, e.g., fluorescently or otherwise labelled, antibodies. The bound antibodies may be detected, for example, by developing the film and/or by using a designated analysis kit. As the antibodies only bind to the protein of interest, only one band should be visible for a specific protein. The thickness of the band corresponds to the amount of protein present. Multiplexing fluorescent western blotting enables multiple proteins to be detected and quantified in a single sample. Direct protein abundance comparisons and normalization may be conducted against a control (herein also termed "loading control"), mostly a ubiquitously and constitutively expressed protein encoded by a control or so-called "housekeeping" gene. An inherent assumption in the use of housekeeping genes is that expression of the genes remains constant in the cells or tissues under investigation. Glyceraldehyde-3-phosphate dehydrogenase (GAPDH) and β-actin are exemplary loading controls.

Frozen tissue/cell cultures of liver or heart were pulverized under liquid nitrogen and placed in a homogenization buffer (10 mmol/F phosphate buffer, 250 mmol/F sucrose, 1 mmol/F EDTA, 0.1 mmol/F phenylmethylsulfonyl fluoride (PMSF), and 0.1% vol/vol tergitol, pH 7.5). Myocytes from cell cultures were homogenized in lysis buffer.

Homogenates were centrifuged at 12K rpm for 10 minutes at 4° C., the supernatant was isolated, and protein levels were visualized by immunoblotting with antibodies. Briefly, proteins (60 μg/sample) were separated using SDS-PAGE gel (12%-15%) under denaturing conditions and electrotransferred (blotted) onto nitrocellulose (Bio-Rad) for 1 hour at 100 V. Membranes were blocked with 5% nonfat milk in Tris-buffered saline with 0.1% Tween® 20 (TBST) for 1 hour at room temperature. Primary antibodies were used at a 1:200-1:1000 concentration in TBST with 5% nonfat milk overnight at 4° C. Immunodetection of β-actin/GPDH was performed as an internal control. Dye 800/680 secondary antibodies were added at a concentration of 1:15000 for 1 hour at room temperature (LI-COR® Biosciences, NE, USA). Detection was carried out with LI-CORE® Odyssey® imaging system. Quantification of signals was carried out with the Odyssey® program.

In Vivo Assays (i) Animals.

Male wild type mice (C57BL) were purchased from Harlan™ (Jerusalem, Israel). Mice were grown in a temperature-controlled atmosphere, 12/12 hours light/dark cycle and given standard food and tap water. The experiments were performed on 2-3-month-old male mice. All experiments were carried out in accordance with the guidelines of the Animal Care and Use Committee of Tel Aviv University with the Guide for the Care and Use of Laboratory Animals published by the US National Institutes of Health.

(ii) Left Anterior Descending Artery (LAD) Ligation

Mice were anesthetized (with a mixture of 100 mg/kg ketamine and 10 mg/kg xylazine), intubated and ventilated with air until spontaneous breathing commenced. The left anterior descending artery (LAD) was ligated with one single stitch, forming an ischemia that can be observed almost immediately. By closing the LAD, no further blood flow is permitted in that area, while the surrounding myocardial tissue is almost not affected. This surgical procedure imitates the pathobiological and pathophysiological aspects occurring in infarction-related myocardial ischemia.

(iii) Serum Isolation

Blood was drawn out from the mice and immediately centrifuged at 4 rpm for 10 minutes to isolate the serum, which was obtained from the top portion of the test tube. The serum was mixed with double distilled water (DDW) in a ratio of 1:10 and was ready for assaying. Various markers were observed (CK, LDH & troponin) to determine cardiac damage in the serum. Additionally, hepatic enzymatic activity of GOT was observed to determine liver functions.

(iv) Heart Infarct Size

Hearts of mice from tested groups were isolated, and pictures were taken to determine the extent of infarct relative to total area of the left ventricle to thereby determine the extent of cardio-protection by an exemplary decoy peptide. The viable heart sections were put in a 1% solution of 2,3,5-triphenyl tetrazolium chloride (TTC) in phosphate buffer for 10 min at 37° C. TTC stained the viable tissue in red while necrotic tissue remained discolored. Sections were fixed overnight in 4% formaldehyde to enhance the contrast between stained and unstained tissue. The sections were then placed between two cover slips and digitally photographed using a Nikon Coolpix 5000 camera, at a resolution of 1400×960 pixels, and quantified by using ImageJ software. The area of ischemia/infarction (TTC-negative) was presented as a percentage of the entire area of the section.

(v) Hematoxylin and Eosin (H&E) Staining and Masson's Trichrome (MT) Staining

Preparation of paraphing blocks. Heart dissects were incubated in 4% formalin for 48 hours for fixation. The dissects were then put in 70% ethanol over-night. Fixation in paraphing was done by the following protocol: for drying, the samples were dipped in 70% ethanol twice, each time for 15 minutes, then put in 80% ethanol for 45 minutes, and lastly put in 90% ethanol for 45 minutes. Finally, they were washed in 100% ethanol 3 times, for about 45 minutes each time. The dissects were put in xylene twice, each time for about 30 minutes. After these drying steps, the dissects were put in hot paraphing for fixation. This process was done 3 times, 45 minutes each time. The final fixation was done in Embedding Station EG 1160 machine of Leica™. Finally, the blocks were cut to a width of 3 μm and were glued to a microscopic slide (HistoBond®, Marienfeld, Germany). The slides were ready for staining and kept at room temperature until used.

Hematoxylin and Eosin (H&E) Staining. Heart dissects that were prepared on slides as described above, were wormed up to 60° C. for 40 minutes, transferred to a xylene solution, and then put in 70%, 96% and 100% alcohol, for 5 minutes each, so as to get rid of the paraphing remnants. For staining, the samples were put in hematoxylin (Pioneer Research, UK) for 15 minutes, which stains acidic cellular components (like DNA) purple. The samples were drawn out of the hematoxylin solution, washed with water for a minute and dipped 3 times in a solution consisting 70% alcohol and 0.4 M HCl. Thereafter, samples were washed with running water for 5 minutes to discard the HCl. The slides were then put in eosin (Pioneer Research, UK), which stains the basic cellular components (like mitochondria) pink. Thereafter, slides were dipped in 70%, 96% and 100% alcohol, twice. After drying, the samples were covered with a glass covering slip coated with glue. Finally, the samples were viewed and photographed using a Zeiss light microscope.

Masson's Trichrome (ML) Staining. Masson's trichrome is a three-colour staining protocol used in histology, e.g., in studies of cardiac pathologies (infarct). Four different stains are used: Weigert's iron hematoxylin for nuclei, picric acid for erythrocytes, a mixture of acid dyes, also termed "plasma stain" (acid fuchsin-"ponceau de xylidine") for cytoplasm, and aniline blue, also termed "fiber stain", for connective tissue. The trichrome is applied by immersion of the fixated sample into Weigert's iron hematoxylin, and then in the three other solutions. Weigert's hematoxylin is a sequence of three solutions: ferric chloride in diluted hydrochloric acid, hematoxylin in 95% ethanol, and potassium ferricyanide solution alkalized by sodium borate. It is used to stain the nuclei.

The plasma stain solution contains acid fuchsin, xylidine ponceau, glacial acetic acid, and distilled water. Other optional red acid dyes include, e.g. the Biebrich scarlet in Lillie's trichrome. The fiber stain used to stain collagen. When blue staining is desired, aniline blue, methyl blue or water blue may be used. For green staining, the fiber stain may contain Light Green SF yellowish, or Fast Green FCF.

Collagen fibers were stained blue, nuclei were stained black and cytoplasm, muscle erythrocytes were stained red. Four different stains were used: Weigert's iron hematoxylin for nuclei, picric acid for erythrocytes, a mixture of acid dyes for cytoplasm and aniline blue for a connective tissue. Slides with the heart dissects (samples) were put under distilled water. On the slides, 6 drops of Weigert's iron hematoxylin was added. Next, the slides were dried for 10 minutes without washing, and 10 drops of picric acid alcoholic solution were added. The slides were dried for 4 minutes, washed quickly (3-4 seconds) in distilled water, and 10 drops of ponceau acid fuchsin were added. The slides were dried for 4 minutes, then washed in distilled water and 10 drops of phosphomolybdic acid solution was added. The slides were dried for 10 minutes. The scarlet-acid fuchsin stain mixture binds to all tissue components because of its small size. This includes both muscle and collagen. Phospho acids such as phosphotungstic and phosphomlybdic acids selectively remove these dyes from collagen and also act as a mordant for the larger dye molecules of aniline blue. If the scarlet-acid fuchsin is insufficiently removed from the collagen, the aniline blue stains poorly or not at all. Without washing, the slides were drained and 10 drops of aniline blue (Masson) were added. Next, the slides were dried for 5 minutes, then washed in distilled water and dehydrated rapidly through treatment with 70% ethanol for 5 minutes. Finally, the samples were viewed and photographed using a Zeiss light microscope.

(vi) RNA Extraction from Myocardium

Total RNA was extracted from auricles by a solution of the RNA isolation reagent TRI Reagent® (Ambion AM9738, NY, USA), concentrated using chloroform, and then centrifuged for 15 minutes at 10600 rpm at 4° C. The RNA was then purified with isopropanol and washed with 70% ethanol. RNA was diluted to a 100 ng/μl mixture and converted to cDNA using the Applied Biosystems™ High Capacity Reverse Transcription Kit (Cat #4368814, Applied Biosystem™ Inc., USA).

Physical and Chemical Analytical Methods

Nuclear Magnetic Resonance (AMR). The $^1$H, $^{13}$C, $^{19}$F NMR and 2D NMR spectra were recorded at room temperature on a Bruker Advance NMR spectrometer (Vernon Hills, Ill., USA) operating at 400 and 600 MHz. Spectra are reported in ppm units (δ) and referenced to TMS at 0 ppm. The samples were prepared by dissolving the synthesized compounds in $CDCl_3$ ($\delta H$=7.26 ppm), $D_2O$ ($\delta_H$=4.79 ppm), DMSO-d ($\delta_H$=2.50 ppm), acetone-$d_6$ ($\delta_H$=2.05 ppm) and/or $CD_3CN$ ($\delta_H$=1-94 ppm). The splitting pattern abbreviations are as follows: "s": singlet; "d": doublet; "t": triplet; "q": quartet; "qui": quintet; "m": unresolved multiplet and "br.": broad.

High-resolution mass spectra (HRMS) were obtained on a Q-TOF instrument (Agilent, Santa Clara, Calif., USA), using electrospray ionization (ESI).

Melting points were measured with a Fisher-Johns melting point apparatus (Waltham, Mass., USA).

Column Flash Chromatography (FC). Flash column chromatography is a specialized chromatography technique that uses compressed gas (such as nitrogen or air) or a pump to push solvent through the column. This technique allows for faster flow rates of the solvent, as opposed to simple gravity flow. In FC, a finer particle size is used for the stationary phase. Flash chromatography was performed on silica gel 60 (230-400 mesh ASTM) from Merck.

Analytical TLC. Thin layer chromatography (TLC) is a chromatographic technique used to separate the components of a mixture using a thin stationary phase supported by an inert backing. It may be performed on the analytical scale as a means of monitoring the progress of a reaction, or on the preparative scale to purify small amounts of a compound. TLC functions on the same principle as all chromatographies: a compound will have different affinities for the mobile and stationary phases, and this affects the speed at which it migrates. After a separation is complete, individual compounds appear as spots separated vertically. Each spot has a retention factor ($R_f$) which is equal to the distance migrated over the total distance covered by the solvent. The solvent may be mixture of polar and non-polar solvents at various ratios. Non-limiting examples of solvent mixtures include dichloromethane (DCM) and hexane (CDM/hexane), DCM/ethanol, hexane/ethyl acetate, toluene/ethyl acetate, TEA/methanol/ethyl acetate and the like.

Organic compounds most commonly appear colorless on the white background of a TLC plate, and have to be "visualized" after elution, namely, temporarily convert into something visible. Visualization methods can be either non-destructive or destructive (compound is converted into something new after the process. Viewing a TLC plate under ultraviolet light is non-destructive, while using a chemical stain is destructive. Ultraviolet (UV) light is non-destructively seed for visualization of aromatics and conjugated systems; a semi-destructive visualization method is to expose a developed TLC plate to iodine ($I_2$) vapor. An "iodine chamber" can be created by adding a few iodine crystals to a TLC chamber. Iodine visualizes aromatics and conjugated groups; The p-anisaldehyde and vanillin stains work for many strong and weak nucleophiles (alcohols, amines), and for many aldehydes and ketones. Vanillin is used for visualization of any aldehydes, ketones, and alcohols.

Analytical TLC was carried out on aluminum TLC plate, silica gel coated with fluorescent indicator $F_{254}$ (TLC Silica gel 60$F_{254}$) (Merck). UV absorption, iodine and vanillin physical adsorption were used for visualization.

Preparative separation was performed by a high pressure liquid chromatography (HPLC) column (Luna®; particle size: 10-micron; phase: C18(2); pore size: 100 Å; AX 100×30.00 mm (length 300 mm, internal diameter 30 mm)), using a $H_2O$/acetonitrile (MeCN) system of solvents: 0-20 min [100/0], and a gradient of 20 min [100/0]-100 min [0/100]. The flow rate was 5 ml/min.

Example 1

Synthesis of Peptides and Peptidomimetics of SEQ ID NOs: 1-24

Synthesis of peptide and peptidomimetics of SEQ ID NOs: 1-24 was carried out using a Rink amide resin as described in Materials and Methods. An acetyl group was substituted at the N-terminus to mimic the amide bond of the original peptide, and to prevent the N-terminus from becoming positively charged.

SEQ ID NOs:1 and 2 served as basic sequences and based thereon most of the peptides and peptidomimetics were designed and synthesized.

Peptidomimetic of SEQ ID NO:7 is similar in structure to SEQ ID NO:5 except for a cleavable protecting group (OtBu) maintained on the side chain of Glu. Corresponding similarity exists also between SEQ ID NO: 18 and SEQ ID NO:20, but β-Ala in SEQ ID NO: 18 is replaced with Ala in SEQ ID NO:20. Peptidomimetics comprising tert-butylated Glu residue have increased lipophilicity and, in addition, the presence of the bulky group near a peptide bond makes the molecule more stable against proteases.

The structure of peptidomimetic of SEQ ID NO:8 is similar to that of SEQ ID NO:2, but it contained only 3 amino acids instead of 4 (Val is missing).

In peptidomimetics of SEQ ID NOs:9 and 10, the amino acid residue alanine (Ala) was replaced by β-Ala (via introduction of Fmoc-β-Ala-OH in the synthesis process). Introduction of the unnatural amino acid β-Ala increases the metabolic stability of the peptidomimetics.

Peptidomimetic of SEQ ID NO: 13 was synthesized based on SEQ ID NO:2 but contains 3 residues (Glu is missing).

SEQ ID NO:14 is similar to SEQ ID NO:13, except for Val being replaced by Ile.

Peptidomimetic of SEQ ID NO: 11 has a structure similar to SEQ ID NO:8, except for Phe being replaced by a naphthalene derivative of Glycine (naphthalen-1-ylmethyl-L-Gly), which is an unnatural and more lipophilic amino acid. Such manipulation accounts for a peptidomimetic having increased lipophilicity and metabolic stability.

Peptidomimetic of SEQ ID NO: 12 was synthesized based on SEQ ID NOG, while replacing Phe with a naphthalene derivative of Glycine (naphthalen-1-ylmethyl-L-Gly).

Peptidomimetic of SEQ ID NO: 19 was synthesized based on SEQ ID NO:2, while replacing Phe with the naphthalene derivative of Glycine (naphthalen-1-ylmethyl-L-Gly).

Peptidomimetic of SEQ ID NO: 15 is an analog of SEQ ID NO: 13, except for Val, the amino acid in the C-terminus, being replaced by unnatural amino acid tert-butylamine (tBuGly), which is a derivative of Glycine.

Peptidomimetic of SEQ ID NO: 16 was synthesized as a derivative of SEQ ID NOG, but replacing Ile was with the unnatural amino acid propylamine, a derivative of Glycine (ProGly).

Peptidomimetic of SEQ ID NO: 17 was synthesized similarly SEQ ID NO: 16, but replacing ProGly with another derivative of Glycine: (S)-(+)-3,3-dimethyl-2-butylamine (diMetButGly).

Peptidomimetic of SEQ ID NO:24 is similar in structure to SEQ ID NO: 16 except for replacing ProGly with tert-pentylamine, a further derivative of Glycine (tPenGly).

Peptidomimetics of SEQ ID NOs:21, 22 and 23 were synthesized as derivatives of SEQ ID NOG, except for using D-Ala instead of L-Ala in SEQ ID NO:21, D-Phe instead of L-Phe in SEQ ID NO:22, and D-Val instead of L-Val in SEQ ID NO:23. These modifications were introduced in order to achieve better metabolic or proteolytic stability.

Mass spectra and NMR analysis of the synthesized peptidomimetics produced the following data:

SEQ ID NO:1: HRMS (ESI): calcd. for $C_{25}H_{40}N_5O_5$ [M+H$^+$]: 490.30240; found: 490.30284;

SEQ ID NO:2: HRMS (ESI): calcd. for $C_{24}H_{36}N_5O_7$ [M+H$^+$]: 506.26092; found: 506.26177;

SEQ ID NO:3: MS (ES+): 538.2 (MH$^+$), 560.2 (MNa$^+$);

SEQ ID NO:4: MS (ES+): 510.2 (MNa$^+$).

SEQ ID NO:5: MS (ES+): 542.1 (MNa$^+$), 558.0 (MK$^+$).

SEQ ID NO:7: MS (ES+): 576.2 (MH$^+$), 598.2 (MNa$^+$).

SEQ ID NO:6: MS (ES+): 470.2 (MNa$^+$).

SEQ ID NO:8: HRMS (ESI): calcd. for $C_{19}H_{27}N_4O_6$ [M+H$^+$]: 407.19251; found: 407.19256.

SEQ ID NO:20: HRMS (ESI): calcd. for $C_{23}H_{35}N_4O_6$ [M+H$^+$]: 463.25511; found: 463.25503.

SEQ ID NO:9: HRMS (ESI): calcd. for $C_{19}H_{27}N_4O_6$ [M+H$^+$]: 407.19251; found: 407.19242.

SEQ ID NO:18: HRMS (ESI): calcd. for $C_{23}H_{35}N_4O_6$ [M+H$^+$]: 463.25511; found: 463.25515.

SEQ ID NO:10: HRMS (ESI): calcd. for $C_{25}H_{40}N_5O_5$ [M+H$^+$]: 490.30240; found: 490.30319.

SEQ ID NO:13: HRMS (ESI): calcd. for $C_{19}H_{29}N_4O_4$ [M+H$^+$]: 377.21833; found: 377.21834. (not a novel compound).

SEQ ID NO:14: HRMS (ESI): calcd. for $C_{20}H_{31}N_4O_4$ [M+H$^+$]: 391.23398; found: 391.23400. (not a novel compound).

SEQ ID NO:11: HRMS (ESI): calcd. for $C_{22}H_{27}N_4O_6$ [M+H$^+$]: 443.19251; found: 443.19227.

SEQ ID NO:12: HRMS (ESI): calcd. for $C_{28}H_{40}N_5O_5$ [M+H$^+$]: 526.30240; found: 526.30238.

SEQ ID NO:19: HRMS (ESI): calcd. for $C_{28}H_{38}N_5O_7$ [M+H$^+$]: 556.27658; found: 556.27630.

SEQ ID NO:21: HRMS (ESI): calcd. for $C_{25}H_{40}N_5O_5$ [M+H$^+$]: 490.30240; found: 490.30206.

SEQ ID NO:22: HRMS (ESI): calcd. for $C_{25}H_{40}N_5O_5$ [M+H$^+$]: 490.30240; found: 490.30232.

SEQ ID NO:23: HRMS (ESI): calcd. for $C_{25}H_{40}N_5O_5$ [M+H$^+$]: 490.30240; found: 490.30219.

SEQ ID NO:15: HRMS (ESI): calcd. for $C_{18}H_{29}N_4O_3$ [M+H$^+$]: 349.22342; found: 349.22340.

SEQ ID NO:16: HRMS (ESI): calcd. for $C_{22}H_{36}N_5O_4$ [M+H$^+$]: 434.27618; found: 434.27686.

SEQ ID NO:17: HRMS (ESI): calcd. for $C_{25}H_{42}N_5O_4$ [M+H$^+$]: 476.32313; found: 476.32441.

SEQ ID NO:24: HRMS (ESI): calcd. for $C_{24}H_{40}N_5O_4$ [M+H$^+$]: 462.30748; found: 462.30946.

Example 2

Synthesis of Compounds PM1-PM10

Compounds PM1-PM10 were synthesized according to a procedure presented in Scheme 1, as follows:

(a) 2,4-dichloro-5-methylpyrimidine (compound 1) (12.35 mmol, 2.00 g) was dissolved in 10 ml of dry ethanol, and a solution of sodium ethoxide (3 equivalents, 37.04 mmol) in 27 ml ethanol was added slowly. The mixture was heated to about 60° C. for 1 hour. The sodium chloride was filtered off; ethanol was removed by reduced pressure to afford a crude material, which was dissolved again in ethyl ether, washed with water and with brine, dried and the solvent was removed under reduced pressure so as to obtain the di-ethyl ester derivative of 1 (compound 2). The total yield was 77% (beige solid).

$R_f$ (TLC)=0.15 (DCM/hexane, 6:4). $^1$HNMR: (400 MHz, CDCl$_3$), $\delta_H$ (ppm): 1.30 (t, J=7.2 Hz, 3H, COCH$_2$CH$_3$), 1.32 (t, J=7.2 Hz, 3H, CH$_3$CCOCH$_2$CH$_3$), 1.95 (d, J=0.8 Hz, 3H, CH$_3$—Ar), 4.27 (q, J=7.2 Hz, 2H, CH$_3$CCOCH$_2$CH$_3$), 4.34 (q, J=7.2 Hz, 2H, COCH$_2$CH$_3$), 7.86 (d, J=0.8 Hz, 1H, CH—Ar). $^{13}$CNMR: (100 MHz, CDCl$_3$) $\delta$, ppm, 11.81 (CH$_3$—Ar), 14.35 (CH$_3$CCOCH$_2$CH$_3$), 14.49 (OCH$_2$CH$_3$), 62.31 (OCH$_2$CH$_3$), 62.97 (CH$_3$CCOCH$_2$CH$_3$), 110.80 (OCCCH$_3$CH), 156.83 (OCCCH$_3$CH), 163.58 (COCH$_2$CH$_3$), 169.21 (OCCCH$_3$CH).

HRMS (ESI): calcd. for $C_9H_{15}N_2O_2$ [M+H$^+$]: 183.11280; found: 183.11333;

(b) benzyl or naphthyl moieties were introduced to the pyrimidine ring by reacting 2 with one of: benzyl bromide, 4-nitrobenzyl bromide, 2-(bromomethyl)naphthalene, or 4-(trifluoromethyl)benzyl bromide in the presence of lithium iodide in dry THF or acetonitrile (MeCN), while heating overnight at about 50-75° C., so as to obtain intermediate compounds 3-6.

(i) synthesis of 1-benzyl-4-ethoxy-5-methylpyrimidin-2 (1H)-one (compound 3). To compound 2 (5.49 mmol, 1 g), lithium iodide (16.47 mmol) and benzyl bromide (17.02 mmol) in 40 ml of dry THF were quickly added, under an inert atmosphere. The reaction mixture was warmed up to about 50° C. overnight. Then, the reaction mixture was poured into a 300 ml solution of saturated sodium bicarbonate and stirred for 1 hour. Thereafter, the solution was extracted with DCM, to the organic layer sodium thiosulfate (8.20 g) and sodium sulfate were added, and the suspension was stirred overnight. Next, the mixture was filtered, and the solvent was removed under reduced pressure to yield an oily residue. Purification of the residue by SiO$_2$ chromatography yielded compound 3. Yield: 95% (white solid).

$R_f$ (TLC)=0.41 (DCM/ethanol, 97:3). mp 123-125° C. $^1$HNMR: (400 MHz, CDCl$_3$), $\delta_H$ (ppm): 1.37 (t, J=6.8 Hz, 3H, COCH$_2$CH$_3$), 1.895 (d, J=0.8 Hz, 3H, CH$_3$CCHN), 4.45 (q, J=7.2 Hz, 2H, COCH$_2$CH$_3$), 5.02 (s, 2H, NCH$_2$Ar), 7.11 (d, J=0.8 Hz, 1H, CH$_3$CCHN), 7.29-7.35 (m, 5H, NCH$_2$Ar). $^{13}$CNMR: (100 MHz, CDCl$_3$) $\delta$, ppm, 12.26 (CH$_3$CCHN), 14.38 (COCH$_2$CH$_3$), 52.35 (NCH$_2$Ar), 63.37 (COCH$_2$CH$_3$), 105.20 (CH$_3$CCHN), 128.31 (NCH$_2$CCH$_{ab}$CH$_{ab}$CH), 128.40 (NCH$_2$CCH$_{ab}$CH$_{ab}$CH), 129.10 (NCH$_2$CCH$_{ab}$CH$_{ab}$CH), 136.34 (NCH$_2$CCH$_{ab}$CH$_{ab}$CH), 143.37 (CH$_3$CCHN), 157.13 (NC=O), 170.38 (COCH$_2$CH$_3$).

HRMS (ESI): calcd. for $C_{14}H_{17}N_2O_2$ [M+H$^+$]: 245.12845; found: 245.12829.

(ii) Synthesis of 4-ethoxy-5-methyl-1-(4-nitrobenzyl)pyrimidin-2(1H)-one (Compound 4). To compound 2 (4.62 mmol, 0.84 g), lithium iodide (13.87 mmol) and 4-nitrobenzyl bromide (14.33 mmol) in 40 ml of dry MeCN were quickly added, under an inert atmosphere. The reaction mixture was warmed up to about 75° C. overnight. The reaction mixture was then poured into a 300 ml solution of saturated sodium bicarbonate and stirred for 1 hour. Thereafter, the solution was extracted with DCM, to the organic layer sodium thiosulfate (8.20 g) and sodium sulfate were added, and the suspension was stirred overnight. Next, the mixture was filtered, and the solvent was removed under reduced pressure to yield a yellow solid. Purification of the residue by SiO$_2$ chromatography yielded compound 4. Yield: 27% (white solid).

$R_f$=0.55 (DCM/ethanol, 97:3). mp 78-80° C. $^1$HNMR: (400 MHz, CDCl$_3$), $\delta_H$ (ppm): 1.39 (t, J=7.2 Hz, 3H, COCH$_2$CH$_3$), 1.93 (s, 3H, CH$_3$CCHN), 4.48 (q, J=7.2 Hz, 2H, COCH$_2$CH$_3$), 5.11 (s, 2H, NCH$_2$Ar), 7.17 (s, 1H, CH$_3$CCHN), 7.48 (d, J=8.4 Hz, 2H, NCH$_2$CCH$_{ab}$CH$_{ab}$CNO$_2$), 8.20 (d, J=8.4 Hz, 2H, NCH$_2$CCH$_{ab}$CH$_{ab}$CNO$_2$). $^{13}$CNMR: (100 MHz, CDCl$_3$) $\delta$, ppm, 12.30 (CH$_3$CCHN), 14.34 (COCH$_2$CH$_3$), 52.09 (NCH$_2$Ar), 63.69 (COCH$_2$CH$_3$), 106.03 (CH$_3$CCHN), 124.26 (NCH$_2$CCH$_{ab}$CH$_{ab}$CNO$_2$), 128.80 (NCH$_2$CCH$_{ab}$CH$_{ab}$CNO$_2$), 143.12 (CH$_3$CCHN), 143.60 (NCH$_2$CCH$_{ab}$CH$_{ab}$CNO$_2$), 147.88 (NCH$_2$CCH$_{ab}$CH$_{ab}$CNO$_2$), 156.82 (NC=O), 170.76 (COCH$_2$CH$_3$).

HRMS (ESI): calcd. for $C_{14}H_{16}N_3O_4$ [M+H$^+$]: 290.11353; found: 290.11392.

(iii) Synthesis of 4-ethoxy-5-methyl-1-(naphthalen-2-yl-methyl)pyrimidin-2(1H)-one (Compound 5). To the oily residue of 2 (1.10 mmol, 0.20 g), lithium iodide (3.30 mmol) and 2-(bromomethyl)naphthalene (3.40 mmol) in 10 ml of dry MeCN were quickly added, under an inert atmosphere. The reaction mixture was warmed up to about 50° C. overnight. The reaction mixture was then poured into a 300 ml solution of saturated sodium bicarbonate, extracted with DCM, filtered and purified by SiO$_2$ chromatography as described above in (ii) to yield compound 5. Yield: 41% (orange solid).

$R_f$=0.26 (toluene/ethyl acetate, 1:1). mp 92-96° C. $^1$HNMR: (400 MHz, CDCl$_3$), $\delta_H$ (ppm): 1.25 (t, J=7.2 Hz, 3H, COCH$_2$CH$_3$), 1.73 (s, 3H, CH$_3$CCHN), 4.34 (q, J=7.2 Hz, 2H, COCH$_2$CH$_3$), 5.04 (s, 2H, NCH$_2$Ar), 7.08 (d, J=1.2 Hz, 1H, CH$_3$CCHN), 7.30 (dd, J=8.4, 1.6 Hz, 1H, 3-C$_{NaPh}$H), 7.33-7.38 (m, 2H, 6,7-C$_{NaPh}$H), 7.62 (s, 1H, 1-C$_{NaPh}$H), 7.67-7.69 (m, 3H, 4,5,8-C$_{NaPh}$H). $^{13}$CNMR:

(100 MHz, CDCl$_3$) δ, ppm, 11.99 (CH$_3$CCHN), 14.17 (COCH$_2$CH$_3$), 52.19 (NCH$_2$Ar), 63.10 (COCH$_2$CH$_3$), 105.04 (CH$_3$CCHN), 125.81 (3-C$_{NaPh}$H), 126.23 (6-C$_{NaPh}$H), 126.37 (7-C$_{NaPh}$H), 127.17 (1-C$_{NaPh}$H), 127.62 (5-C$_{NaPh}$H), 127.77 (8-C$_{NaPh}$H), 128.82 (4-C$_{NaPh}$H), 132.89 (10-C$_{NaPh}$), 133.18 (9-C$_{NaPh}$), 133.68 (2-C$_{NaPh}$), 143.38 (CH$_3$CCHN), 156.99 (NC=O), 170.18 (COCH$_2$CH$_3$).

HRMS (ESI): calcd. for C$_{18}$H$_{19}$N$_2$O$_2$ [M+H$^+$]: 295.14410; found: 295.14369.

(iv) Synthesis of 4-ethoxy-5-methyl-1-(4-(trifluoromethyl)benzyl)pyrimidin-2(1H)-one (Compound 6). To the oily residue of 2 (1.65 mmol, 0.30 g), lithium iodide (4.94 mmol) and 4-(trifluoromethyl)benzyl bromide (5.11 mmol) in 10 ml of dry MeCN were quickly added, under an inert atmosphere. The reaction mixture was warmed up to about 75° C. overnight. The reaction mixture was then poured into a 300 ml solution of saturated sodium bicarbonate, extracted with DCM, filtered under reduced pressure to yield an oily residue and purified by SiO$_2$ chromatography as described above in (ii), and compound 6 was yielded. Yield: 74% (beige solid).

R$_f$(TLC)=0.27 (hexane/ethyl acetate, 1:1). mp 99-101° C. $^1$HNMR: (400 MHz, CDCl$_3$), δ$_H$ (ppm): 1.40 (t, J=7.2 Hz, 3H, COCH$_2$CH$_3$), 1.91 (d, J=1.2 Hz, 3H, CH$_3$CCHN), 4.47 (q, J=7.2 Hz, 2H, COCH$_2$CH$_3$), 5.08 (s, 2H, NCH$_2$Ar), 7.15 (d, J=1.2 Hz, 1H, CH$_3$CCHN), 7.43 (d, J=8.0 Hz, 2H, NCH$_2$CCH$_{ab}$CH$_{ab}$CCF$_3$), 7.60 (d, J=8.0 Hz, 2H, NCH$_2$CCH$_{ab}$CH$_{ab}$CCF$_3$). $^{13}$CNMR: (100 MHz, CDCl$_3$) δ, ppm, 12.25 (CH$_3$CCHN), 14.34 (COCH$_2$CH$_3$), 52.10 (NCH$_2$Ar), 63.53 (COCH$_2$CH$_3$), 105.68 (CH$_3$CCHN), 124.07 (q, J=272.1 Hz, CF$_3$), 126.01 (q, J=3.6 Hz, NCH$_2$CCH$_{ab}$CH$_{ab}$CCF$_3$), 128.43 (NCH$_2$CCH$_{ab}$CH$_{ab}$CCF$_3$), 130.55 (q, J=32.6 Hz, NCH$_2$CCH$_{ab}$CH$_{ab}$CCF$_3$), 140.40 (NCH$_2$CCH$_{ab}$CH$_{ab}$CCF$_3$), 143.23 (CH$_3$CCHN), 156.92 (NC=O), 170.60 (COCH$_2$CH$_3$).

HRMS (ESI): calcd. for C$_{15}$H$_{16}$F$_3$N$_2$O$_2$ [M+H$^+$]: 313.11584; found: 313.11709;

(c) the ethyl ester moiety in 3-6 (0.50 mmol) was replaced by various amine moieties (see Table 3 below) using a pressure tube, long incubation times (3 days) at 130° C., and methanol as a solvent (10 ml). In the next steps, the reaction reached RT, methanol was removed under reduced pressure yielding an oily residue, and distillation and purification of the residue by SiO$_2$ chromatography yielded 10 decoy peptides designated as PM1-PM10. The following amines (NH$_2$—R$_2$) (15 ml) were used for preparing PM1-PM10: sec-butylamine (PM1, yield 90%), isopentylamine (PM2, yield 84%), cyclopentylamine (PM3, yield 90%), 3-dimethylamine-propylamine (PM4, yield 90%), benzylamine (PM5, yield 60%), octylamine (PM6, yield 88%), octylamine (PM7, yield 30%), octylamine (PM8, yield 87%), octylamine (PM9, yield 86%) and decylamine (PM10, yield 23%).

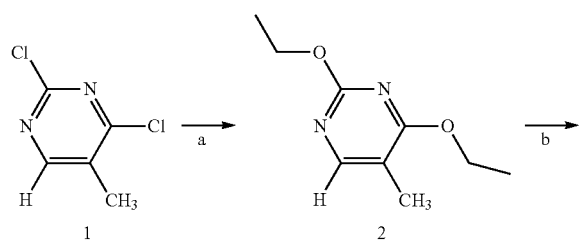

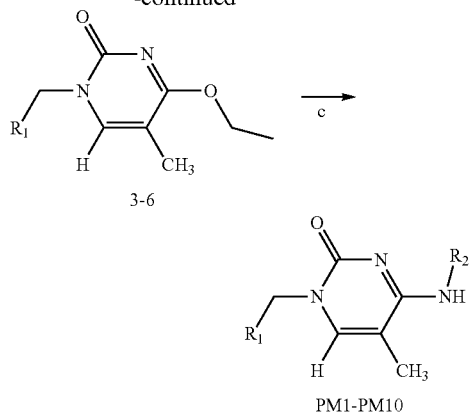

| Scheme 1 | | |
|---|---|---|
| Compound | R1 | R2 |
| PM1 | Ph— | CH$_3$CH$_2$CHCH$_3$— |
| PM2 | Ph— | (CH$_3$)$_2$CH(CH$_2$)$_2$— |
| PM3 | Ph— | (CH$_2$)$_4$CH— |
| PM4 | Ph— | (CH$_3$)$_2$N(CH$_2$)$_3$— |
| PM5 | Ph— | Bn- |
| PM6 | Ph— | CH$_3$(CH$_2$)$_7$— |
| PM7 | pO$_2$N—C$_6$H$_4$— | CH$_3$(CH$_2$)$_7$— |
| PM8 | 2-Naph | CH$_3$(CH$_2$)$_7$— |
| PM9 | pF$_3$C—C$_6$H$_4$— | CH$_3$(CH$_2$)$_7$— |
| PM10 | Ph— | CH$_3$(CH$_2$)$_9$— |

Analytical Data:

PM1: Yield: 90% (beige solid). R$_f$=0.15 (hexane/ethyl acetate, 1:4). mp 96-100° C. $^1$HNMR: (400 MHz, CDCl$_3$), δ$_H$ (ppm): 0.93 (t, J=7.6 Hz, 3H, CH$_3$CH$_2$CHCH$_3$NH), 1.19 (d, J=6.4 Hz, 3H, CH$_3$CH$_2$CHCH$_3$NH), 1.50-1.60 (m, 2H, CH$_3$CH$_2$CHCH$_3$NH), 1.82 (d, J=0.8 Hz, 3H, NHCCCH$_3$CH), 4.36-4.46 (m, 1H, CH$_3$CH$_2$CHCH$_3$NH), 4.50 (brd, 1H, CH$_3$CH$_2$CHCH$_3$NH), 4.99 (s, 2H, NCH$_2$Ar), 6.92 (d, J=0.8 Hz, 1H, NHCCCH$_3$CH), 7.26-7.36 (m, 5H, NCH$_2$Ar). $^{13}$CNMR: (100 MHz, CDCl$_3$) δ, ppm, 10.24 (CH$_3$CH$_2$CHCH$_3$NH), 12.96 (NHCCCH$_3$CH), 20.39 (CH$_3$CH$_2$CHCH$_3$NH), 29.53 (CH$_3$CH$_2$CHCH$_3$NH), 47.35 (CH$_3$CH$_2$CHCH$_3$NH), 51.80 (NCH$_2$Ar), 101.56 (NHCCCH$_3$CH), 127.87 (NCH$_2$CCH$_{ab}$CH$_{ab}$CH), 128.26 (NCH$_2$CCH$_{ab}$CH$_{ab}$CH), 128.83 (NCH$_2$CCH$_{ab}$CH$_{ab}$CH), 137.00 (NCH$_2$CCH$_{ab}$CH$_{ab}$CH), 141.16 (NHCCCH$_3$CH), 157.32 (NC=O), 162.59 (NHCCCH$_3$CH).

HRMS (ESI): calcd. for C$_{16}$H$_{22}$F$_3$N$_3$O [M+H$^+$]: 272.17574; found: 272.17670.

PM2: Yield: 84% (white solid). R$_f$=0.13 (hexane/ethyl acetate, 1:4). mp 101-103° C. $^1$HNMR: (400 MHz, Acetone-D), δ$_H$ (ppm): 0.91 (d, J=6.8 Hz, 6H, CH$_3$CH$_3$CHCH$_2$CH$_2$NH), 1.50 (dt, J=7.6 Hz, 7.2 Hz, 2H, CH$_3$CH$_3$CHCH$_2$CH$_2$NH), 1.60-1.70 (m, 1H, CH$_3$CH$_3$CHCH$_2$CH$_2$NH), 1.88 (d, J=1.2 Hz, 3H, NHCCCH$_3$CH), 3.45-3.50 (m, 2H, CH$_3$CH$_3$CHCH$_2$CH$_2$NH), 4.92 (s, 2H, NCH$_2$Ar), 7.23-7.37 (m, 1H, NHCCCH$_3$CH), 7.23-7.37 (m, 5H, NCH$_2$Ar). $^{13}$CNMR: (100 MHz, Acetone-D) δ, ppm, 13.10 (NHCCCH$_3$CH), 23.00 (CH$_3$CH$_3$CHCH$_2$CH$_2$NH), 26.75 (CH$_3$CH$_3$CHCH$_2$CH$_2$NH), 39.04 (CH$_3$CH$_3$CHCH$_2$CH$_2$NH), 39.83 (CH$_3$CH$_3$CHCH$_2$CH$_2$NH), 52.28 (NCH$_2$Ar), 102.37 (NHCCCH$_3$CH), 128.31 (NCH$_2$CCH$_{ab}$CH$_{ab}$CH), 128.89

(NCH$_2$CCH$_{ab}$CH$_{ab}$CH), 129.43 (NCH$_2$CCH$_{ab}$CH$_{ab}$CH), 139.55 (NCH$_2$CCH$_{ab}$CH$_{ab}$CH), 142.86 (NHCCCH$_3$CH), 157.17 (NC=O), 164.46 (NHCCCH$_3$CH).

HRMS (ESI): calcd. for C$_{17}$H$_{23}$N$_3$ONa [M+Na$^+$]: 308.17333; found: 308.17357.

PM3: Yield: 90% (beige solid). R$_f$=0.10 (hexane/ethyl acetate, 1:4). mp 152-154° C. $^1$HNMR: (600 MHz, DMSO), δ$_H$ (ppm): 1.46-1.54 (m, 4H, CHHCHHCHHCHNH), 1.64-1.72 (m, 2H, CHHCHHCHHCHNH), 1.83 (s, 3H, NHCCCH$_3$CH), 1.86-1.93 (m, 2H, CHHCHHCHHCHNH), 4.30-4.40 (m, 1H, CHHCHHCHHCHNH), 4.82 (s, 2H, NCH$_2$Ar), 6.68 (d, J=7.2 Hz, 1H, NHCCCH$_3$CH), 7.25-7.33 (m, 5H, NCH$_2$Ar), 7.47 (s, 1H, NHCCCH$_3$CH). $^{13}$CNMR: (150 MHz, DMSO) δ, ppm, 12.85 (NHCCCH$_3$CH), 23.52 (CH$_2$CH$_2$CH$_2$CH$_2$CHNH), 31.76 (CH$_2$CH$_2$CH$_2$CH$_2$CHNH), 50.88 (NCH$_2$Ar), 51.54 (CH$_2$CH$_2$CH$_2$CH$_2$CHNH), 101.31 (NHCCCH$_3$CH), 127.20 (NCH$_2$CCH$_{ab}$CH$_{ab}$CH), 127.45 (NCH$_2$CCH$_{ab}$CH$_{ab}$CH), 128.39 (NCH$_2$CCH$_{ab}$CH$_{ab}$CH), 138.15 (NCH$_2$CCH$_{ab}$CH$_{ab}$CH), 142.22 (NHCCCH$_3$CH), 155.70 (NC=O), 162.69 (NHCCCH$_3$CH).

HRMS (ESI): calcd. for C$_{17}$H$_{22}$N$_3$O [M+H$^+$]: 284.17574; found: 284.17595.

PM4: Yield: 90% (yellow oil). R$_f$=0.14 (TEA/methanol/ethyl acetate, 5:20:75). $^1$HNMR: (400 MHz, CD$_3$CN), δ$_H$ (ppm): 1.77-1.83 (m, 2H, CH$_3$CH$_3$NCH$_2$CH$_2$CH$_2$NH), 1.83 (d, 3H, J=1.2 Hz, NHCCCH$_3$CH), 2.37 (s, 6H, CH$_3$CH$_3$NCH$_2$CH$_2$CH$_2$NH), 2.59 (t, J=6.4 Hz, 2H, CH$_3$CH$_3$NCH$_2$CH$_2$CH$_2$NH), 3.47 (m, 2H, CH$_3$CH$_3$NCH$_2$CH$_2$CH$_2$NH), 4.86 (s, 2H, NCH$_2$Ar), 7.22 (d, J=0.8 Hz, 1H, NHCCCH$_3$CH), 7.25-7.36 (m, 5H, NCH$_2$Ar). $^{13}$CNMR: (100 MHz, CD$_3$CN) δ, ppm, 12.97 (NHCCCH$_3$CH), 25.93 (CH$_3$CH$_3$NCH$_2$CH$_2$NH), 40.72 (CH$_3$CH$_3$NCH$_2$CH$_2$CH$_2$NH), 44.82 (CH$_3$CH$_3$NCH$_2$CH$_2$CH$_2$NH), 52.61 (NCH$_2$Ar), 58.16 (CH$_3$CH$_3$NCH$_2$CH$_2$CH$_2$NH), 103.27 (NHCCCH$_3$CH), 128.46 (NCH$_2$CCH$_{ab}$CH$_{ab}$CH), 128.54 (NCH$_2$CCH$_{ab}$CH$_{ab}$CH), 129.59 (NCH$_2$CCH$_{ab}$CH$_{ab}$CH), 139.14 (NCH$_2$CCH$_{ab}$CH$_{ab}$CH), 142.95 (NHCCCH$_3$CH), 157.56 (NC=O), 164.69 (NHCCCH$_3$CH).

HRMS (ESI): calcd. for C$_{17}$H$_{25}$N$_4$O [M+H$^+$]: 301.20229; found: 301.20262.

PM5: Yield: 60% (beige solid). R$_f$=0.21 (hexane/ethyl acetate, 1:4). mp 120-122° C. $^1$HNMR: (400 MHz, DMSO), δ$_H$ (ppm): 1.88 (s, 3H, NHCCCH$_3$CH), 4.56 (d, J=6.0 Hz, 2H, NHCH$_2$Ar), 4.83 (s, 2H, NCH$_2$Ar), 7.20-7.34 (m, 10H, NCH$_2$Ar, NHCH$_2$Ar), 7.53 (s, 1H, NHCCCH$_3$CH), 7.58 (brt, J=8.0 Hz, 1H, NHCH$_2$Ar). $^{13}$CNMR: (100 MHz, DMSO) δ, ppm, 12.72 (NHCCCH$_3$CH), 43.08 (NHCH$_2$Ar), 50.95 (NCH$_2$Ar), 101.26 (NHCCCH$_3$CH), 126.52 (NHCH$_2$CCH$_{ab}$CH$_{ab}$CH), 127.02 (NHCH$_2$CCH$_{ab}$CH$_{ab}$CH), 127.21 (NCH$_2$CCH$_{ab}$CH$_{ab}$CH), 127.48 (NCH$_2$CCH$_{ab}$CH$_{ab}$CH), 128.10 (NHCH$_2$CCH$_{ab}$CH$_{ab}$CH), 128.38 (NCH$_2$CCH$_{ab}$CH$_{ab}$CH), 138.02 (NCH$_2$CCH$_{ab}$CH$_{ab}$CH), 139.54 (NHCH$_2$CCH$_{ab}$CH$_{ab}$CH), 142.57 (NHCCCH$_3$CH), 155.64 (NC=O), 163.05 (NHCCCH$_3$CH).

HRMS (ESI): calcd. for C$_{19}$H$_{20}$N$_3$O [M+H$^+$]: 306.16009; found: 306.16095.

PM6: Yield: 88% (yellow oil). R$_f$=0.15 (hexane/ethyl acetate, 1:4). $^1$HNMR: (400 MHz, DMSO), δ$_H$ (ppm): 0.85 (t, J=7.2 Hz, 3H, NHCH$_2$CH$_2$CH$_2$CH$_2$CH$_2$CH$_2$CH$_3$), 1.25 (m, 10H, NHCH$_2$CH$_2$CH$_2$CH$_2$CH$_2$CH$_2$CH$_3$), 1.50 (m, 2H, NHCH$_2$CH$_2$CH$_2$CH$_2$CH$_2$CH$_2$CH$_3$), 1.81 (s, 3H, NHCCCH$_3$CH), 3.29 (m, 2H, NHCH$_2$CH$_2$CH$_2$CH$_2$CH$_2$CH$_2$CH$_3$), 4.81 (s, 2H, NCH$_2$Ar), 7.00 (t, J=5.6 Hz, 1H, NHCCCH$_3$CH), 7.24-7.34 (m, 5H, NCH$_2$Ar), 7.46 (s, 1H, NHCCCH$_3$CH). $^{13}$CNMR: (100 MHz, DMSO) δ, ppm, 12.77 (NHCCCH$_3$CH), 13.93 (NHCH$_2$CH$_2$CH$_2$CH$_2$CH$_2$CH$_2$CH$_3$), 22.06 (NHCH$_2$CH$_2$CH$_2$CH$_2$CH$_2$CH$_2$CH$_3$), 26.49 (NHCH$_2$CH$_2$CH$_2$CH$_2$CH$_2$CH$_2$CH$_3$), 28.59 (NHCH$_2$CH$_2$CH$_2$CH$_2$CH$_2$CH$_2$CH$_3$), 28.65 (NHCH$_2$CH$_2$CH$_2$CH$_2$CH$_2$CH$_2$CH$_3$), 28.79 (NHCH$_2$CH$_2$CH$_2$CH$_2$CH$_2$CH$_2$CH$_3$), 31.22 (NHCH$_2$CH$_2$CH$_2$CH$_2$CH$_2$CH$_2$CH$_3$), 40.16 (NHCH$_2$CH$_2$CH$_2$CH$_2$CH$_2$CH$_2$CH$_3$), 50.90 (NCH$_2$Ar), 101.32 (NHCCCH$_3$CH), 127.22 (NCH$_2$CCH$_{ab}$CH$_{ab}$CH), 127.46 (NCH$_2$CCH$_{ab}$CH$_{ab}$CH), 128.41 (NCH$_2$CCH$_{ab}$CH$_{ab}$CH), 138.19 (NCH$_2$CCH$_{ab}$CH$_{ab}$CH), 142.14 (NHCCCH$_3$CH), 155.78 (NC=O), 162.97 (NHCCCH$_3$CH).

HRMS (ESI): calcd. for C$_{20}$H$_{30}$N$_3$O [M+H$^+$]: 328.23834; found: 328.23918.

PM7: Yield: 30% (yellow oil). R$_f$=0.43 (DCM/ethanol, 97:3). $^1$HNMR: (400 MHz, CDCl$_3$), δ$_H$ (ppm): 0.86 (t, J=7.2 Hz, 3H, NHCH$_2$CH$_2$CH$_2$CH$_2$CH$_2$CH$_2$CH$_3$), 1.20-1.30 (m, 10H, NHCH$_2$CH$_2$CH$_2$CH$_2$CH$_2$CH$_2$CH$_3$), 1.59 (m, 2H, NHCH$_2$CH$_2$CH$_2$CH$_2$CH$_2$CH$_2$CH$_3$), 1.87 (s, 3H, NHCCCH$_3$CH), 3.52 (m, 2H, NHCH$_2$CH$_2$CH$_2$CH$_2$CH$_2$CH$_2$CH$_3$), 4.98 (brs, 1H, NHCCCH$_3$CH), 5.04 (s, 2H, NCH$_2$Ar), 6.96 (s, 1H, NHCCCH$_3$CH), 7.44 (d, J=8.4 Hz, 2H, NCH$_2$CCH$_{ab}$CH$_{ab}$CNO$_2$), 8.14 (d, J=8.4 Hz, 2H, NCH$_2$CCH$_{ab}$CH$_{ab}$CN O$_2$). $^{13}$CNMR: (100 MHz, CDCl$_3$) δ, ppm, 12.99 (NHCCCH$_3$CH), 14.16 (NHCH$_2$CH$_2$CH$_2$CH$_2$CH$_2$CH$_2$CH$_3$), 22.72 (NHCH$_2$CH$_2$CH$_2$CH$_2$CH$_2$CH$_2$CH$_3$), 27.06 (NHCH$_2$CH$_2$CH$_2$CH$_2$CH$_2$CH$_2$CH$_3$), 29.29 (NHCH$_2$CH$_2$CH$_2$CH$_2$CH$_2$CH$_2$CH$_3$), 29.39 (NHCH$_2$CH$_2$CH$_2$CH$_2$CH$_2$CH$_2$CH$_3$), 29.79 (NHCH$_2$CH$_2$CH$_2$CH$_2$CH$_2$CH$_2$CH$_3$), 31.87 (NHCH$_2$CH$_2$CH$_2$CH$_2$CH$_2$CH$_2$CH$_3$), 41.39 (NHCH$_2$CH$_2$CH$_2$CH$_2$CH$_2$CH$_2$CH$_3$), 51.69 (NCH$_2$Ar), 102.57 (NHCCCH$_3$CH), 124.04 (NCH$_2$CCH$_{ab}$CH$_{ab}$CNO$_2$), 128.63 (NCH$_2$C CH$_{ab}$CH$_{ab}$CN O$_2$), 141.04 (NHCCCH$_3$CH), 144.59 (NCH$_2$CCH$_{ab}$CH$_{ab}$CNO$_2$), 147.61 (NCH$_2$CCH$_{ab}$CH$_{ab}$CNO$_2$), 157.02 (NC=O), 163.42 (COCH$_3$).

HRMS (ESI): calcd. for C$_{20}$H$_{29}$N$_4$O$_3$ [M+H$^+$]: 373.22342; found: 373.22310.

PM8: Yield: 87% (yellow oil). R$_f$=0.09 (toluene/ethyl acetate, 5:6). $^1$HNMR: (400 MHz, CDCl$_3$), δ$_H$ (ppm): 0.84 (t, J=6.8 Hz, 3H, NHCH$_2$CH$_2$CH$_2$CH$_2$CH$_2$CH$_2$CH$_3$), 1.20-1.30 (m, 10H, NHCH$_2$CH$_2$CH$_2$CH$_2$CH$_2$CH$_2$CH$_3$), 1.57 (m, 2H, NHCH$_2$CH$_2$CH$_2$CH$_2$CH$_2$CH$_2$CH$_3$), 1.78 (s, 3H, NHCCCH$_3$CH), 3.50 (m, 2H, NHCH$_2$CH$_2$CH$_2$CH$_2$CH$_2$CH$_2$CH$_3$), 5.08 (s, 2H, NCH$_2$Ar), 5.16 (brt, J=5.2 Hz, 1H, NHCCCH$_3$CH), 6.90 (s, 1H, NHCCCH$_3$CH), 7.38-7.50 (m, 3H, 3,6,7-C$_{NaPh}$H), 7.68 (s, 1H, 1-C$_{NaPh}$H), 7.74-7.77 (m, 3H, 4,5,8-C$_{NaPh}$H). $^{13}$CNMR: (100 MHz, CDCl$_3$) δ, ppm, 12.92 (NHCCCH$_3$CH), 14.09 (NHCH$_2$CH$_2$CH$_2$CH$_2$CH$_2$CH$_2$CH$_3$), 22.63 (NHCH$_2$CH$_2$CH$_2$CH$_2$CH$_2$CH$_2$CH$_3$), 27.00 (NHCH$_2$CH$_2$CH$_2$CH$_2$CH$_2$CH$_2$CH$_3$), 29.22 (NHCH$_2$CH$_2$CH$_2$CH$_2$CH$_2$CH$_2$CH$_3$), 29.32 (NHCH$_2$CH$_2$CH$_2$CH$_2$CH$_2$CH$_2$CH$_3$), 31.79 (NHCH$_2$CH$_2$CH$_2$CH$_2$CH$_2$CH$_2$CH$_3$), 41.21 (NHCH$_2$CH$_2$CH$_2$CH$_2$CH$_2$CH$_2$CH$_3$), 51.81 (NCH$_2$Ar), 102.14 (NHCCCH$_3$CH), 125.99 (7-C$_{NaPh}$H), 126.10 (6-C$_{NaPh}$H), 126.31 (3-C$_{NaPh}$H), 126.95 (1-C$_{NaPh}$H), 127.67 (8-C$_{NaPh}$H), 127.80 (5-C$_{NaPh}$H), 128.71 (4-C$_{NaPh}$H), 132.88

(10-C$_{NaPh}$), 133.27 (9-C$_{NaPh}$), 134.58 (2-C$_{NaPh}$), 140.95 (NHCCCH$_3$CH), 157.37 (NC=O), 163.14 (NHCCCH$_3$CH).

HRMS (ESI): calcd. for C$_{24}$H$_{32}$N$_3$O [M+H$^+$]: 378.25399; found: 378.25372.

PM9: Yield: 86% (yellow oil). R$_f$=0.16 (hexane/ethyl acetate, 1:4). $^1$HNMR: (400 MHz, CDCl$_3$), δ$_H$ (ppm): 0.88 (t, J=6.8 Hz, 3H, NHCH$_2$CH$_2$CH$_2$CH$_2$CH$_2$CH$_2$CH$_3$), 1.24-1.37 (m, 10H, NHCH$_2$CH$_2$CH$_2$CH$_2$CH$_2$CH$_2$CH$_3$), 1.61 (m, 2H, NHCH$_2$CH$_2$CH$_2$CH$_2$CH$_2$CH$_2$CH$_3$), 1.87 (d, J=0.8 Hz, 3H, NHCCCH$_3$CH), 3.54 (m, 2H, NHCH$_2$CH$_2$CH$_2$CH$_2$CH$_2$CH$_2$CH$_3$), 4.86 (brs, 1H, NHCCCH$_3$CH), 5.03 (s, 2H, NCH$_2$Ar), 6.94 (d, J=0.8 Hz, 1H, NHCCCH$_3$CH), 7.42 (d, J=8.4 Hz, 2H, NCH$_2$CCH$_{ab}$CH$_{ab}$CCF$_3$), 7.58 (d, J=8.4 Hz, 2H, NCH$_2$CCH$_{ab}$CH$_{ab}$CCF$_3$). $^{13}$CNMR: (100 MHz, CDCl$_3$) δ, ppm, 13.03 (NHCCCH$_3$CH), 14.20 (NHCH$_2$CH$_2$CH$_2$CH$_2$CH$_2$CH$_2$CH$_3$), 22.76 (NHCH$_2$CH$_2$CH$_2$CH$_2$CH$_2$CH$_2$CH$_3$), 27.10 (NHCH$_2$CH$_2$CH$_2$CH$_2$CH$_2$CH$_2$CH$_3$), 29.34 (NHCH$_2$CH$_2$CH$_2$CH$_2$CH$_2$CH$_2$CH$_3$), 29.44 (NHCH$_2$CH$_2$CH$_2$CH$_2$CH$_2$CH$_2$CH$_3$), 29.46 (NHCH$_2$CH$_2$CH$_2$CH$_2$CH$_2$CH$_2$CH$_3$), 31.92 (NHCH$_2$CH$_2$CH$_2$CH$_2$CH$_2$CH$_2$CH$_3$), 41.40 (NHCH$_2$CH$_2$CH$_2$CH$_2$CH$_2$CH$_2$CH$_3$), 51.71 (NCH$_2$Ar), 102.24 (NHCCCH$_3$CH), 124.17 (q, J=273.6 Hz, CF$_3$), 125.87 (q, J=3.6 Hz, NCH$_2$CCH$_{ab}$CH$_{ab}$CCF$_3$), 128.35 (NCH$_2$CCH$_{ab}$CH$_{ab}$CCF$_3$), 130.26 (q, J=32.0 Hz, NCH$_2$CCH$_{ab}$CH$_{ab}$CCF$_3$), 141.12 (NHCCCH$_3$CH), 141.22 (NCH$_2$CCH$_{ab}$CH$_{ab}$CCF$_3$), 157.17 (NC=O), 163.32 (NHCCCH$_3$CH).

HRMS (ESI): calcd. for C$_{21}$H$_{29}$F$_3$N$_3$O [M+H$^+$]: 396.22572; found: 396.22537.

PM10: Yield: 23% (yellow oil). R$_f$=0.43 (hexane/ethyl acetate, 1:4). $^1$HNMR: (400 MHz, CDCl$_3$), δ$_H$ (ppm): 0.80 (t, J=6.4 Hz, 3H, NHCH$_2$CH$_2$CH$_2$CH$_2$CH$_2$CH$_2$CH$_2$CH$_2$CH$_3$), 1.15-1.25 (m, 14H, NHCH$_2$CH$_2$CH$_2$CH$_2$CH$_2$CH$_2$CH$_2$CH$_2$CH$_3$), 1.51 (m, 2H, NHCH$_2$CH$_2$CH$_2$CH$_2$CH$_2$CH$_2$CH$_2$CH$_2$CH$_3$), 1.76 (s, 3H, NHCCCH$_3$CH), 3.43 (m, 2H, NHCH$_2$CH$_2$CH$_2$CH$_2$CH$_2$CH$_2$CH$_2$CH$_2$CH$_3$), 4.89 (s, 2H, NCH$_2$Ar), 5.05 (brt, J=4.8 Hz, 1H, NHCCCH$_3$CH), 6.84 (s, 1H, NHCCCH$_3$CH), 7.17-7.25 (m, 5H, NCH$_2$Ar). $^{13}$CNMR: (100 MHz, CDCl$_3$) δ, ppm, 12.96 (NHCCCH$_3$CH), 14.12 (NHCH$_2$CH$_2$CH$_2$CH$_2$CH$_2$CH$_2$CH$_2$CH$_2$CH$_3$), 22.68 (NHCH$_2$CH$_2$CH$_2$CH$_2$CH$_2$CH$_2$CH$_2$CH$_2$CH$_3$), 27.01 (NHCH$_2$CH$_2$CH$_2$CH$_2$CH$_2$CH$_2$CH$_2$CH$_2$CH$_3$), 29.31 (NHCH$_2$CH$_2$CH$_2$CH$_2$CH$_2$CH$_2$CH$_2$CH$_2$CH$_3$), 29.34 (NHCH$_2$CH$_2$CH$_2$CH$_2$CH$_2$CH$_2$CH$_2$CH$_2$CH$_3$), 29.39 (NHCH$_2$CH$_2$CH$_2$CH$_2$CH$_2$CH$_2$CH$_2$CH$_2$CH$_3$), 29.58 (NHCH$_2$CH$_2$CH$_2$CH$_2$CH$_2$CH$_2$CH$_2$CH$_2$CH$_3$), 31.89 (NHCH$_2$CH$_2$CH$_2$CH$_2$CH$_2$CH$_2$CH$_2$CH$_2$CH$_3$), 41.20 (NHCH$_2$CH$_2$CH$_2$CH$_2$CH$_2$CH$_2$CH$_2$CH$_2$CH$_3$), 51.76 (NCH$_2$Ar), 101.98 (NHCCCH$_3$CH), 127.80 (NCH$_2$CCH$_{ab}$CH$_{ab}$CH), 128.09 (NCH$_2$CCH$_{ab}$CH$_{ab}$CH), 128.77 (NCH$_2$CCH$_{ab}$CH$_{ab}$CH), 137.08 (NCH$_2$CCH$_{ab}$CH$_{ab}$CH), 141.03 (NHCCCH$_3$CH), 157.31 (NC=O), 163.16 (NHCCCH$_3$CH).

HRMS (ESI): calcd. for C$_{22}$H$_{34}$N$_3$O [M+H$^+$]: 356.26964; found: 356.27079.

Example 3

Synthesis of Unnatural Amino Acid (Compound 10)

An unnatural amino acid derived from naphthalene, herein designated compound 10, was synthesized for the purpose of, e.g., replacing phenylalanine (Phe), in exemplary peptidomimetics provided herein. Compound 10 is more lipophilic than Phe and, when introduced into a peptide, may increase the lipophilicity and metabolic stability of the peptide. The synthetic pathway, shown in Scheme 2, has the following steps.

(a) Synthesis of 2-amino-2-(naphthalen-1-yl)acetonitrile (Compound 8)

A 7 N ammonia solution in methanol (NH$_3$/MeOH) (10 ml) was added rapidly, at 0° C., to 1-naphthaldehyde (compound 7) (6.40 mmol, 1.00 g) and stirred for 20 min.

Thereafter, trimethylsilyl cyanide (TMSCN) (9.60 mmol) was added slowly and stirred at RT overnight ("Strecker synthesis"). Methanol was removed under reduced pressure, ethyl acetate was added, and then the reaction mixture was extracted with water, the organic layer was separated, washed with brine, dried over MgSO$_4$, and the solvent was removed under reduced pressure to yield an oily residue. Purification of the residue by SiO$_2$ chromatography yielded compound 8 (50%). Obtained NMR data corresponded to the literature data.

(b) Synthesis of 2-amino-2-(naphthalen-1-yl)acetic Acid (Compound 9)

To compound 8 (2.79 mmol, 0.51 g), 6M HCl (13 ml) was added, and the reaction mixture was refluxed for 6 hours. Then, the reaction mixture was cooled to RT and water was removed under reduced pressure. The product was dissolved in DCM, filtered, and washed with DCM and ethyl acetate to yield the white solid, carboxylic derivative compound 9 (76%). Obtained NMR data corresponded to the literature data.

(c) Synthesis of Fmoc-(D,L)-α-naphthyl-phenylglycine (Compound 10)

A solution of 9 (1.84 mmol, 0.37 g), Fmoc-N-hydroxysuccinimide ester (Fmoc-ONSu) (2.02 mmol) and sodium bicarbonate (7.21 mmol) in water (10 ml), and acetone (7 ml) were stirred at RT overnight. The reaction mixture was then washed with diethyl ether (50 ml), acidified with 1 N HCl (to pH=3), and extracted with DCM (three times). The organic layer was separated, washed with brine, dried over MgSO$_4$, and the solvent was removed under reduced pressure to yield a white solid 10 (53%). Obtained NMR data corresponded to the literature data.

Scheme 2

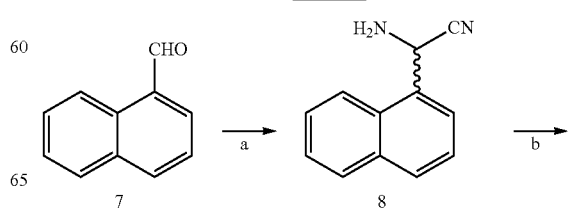

-continued

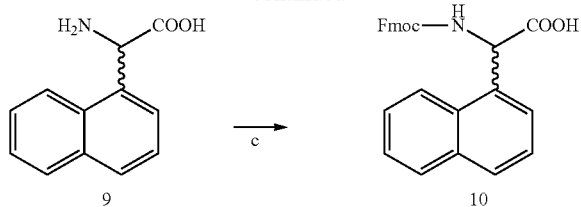

Example 4

In Vitro Evaluation of Decoy Peptides

Primary cardiomyocytes were treated with peptides and peptidomimetics of SEQ ID NOs:1-7 provided at concentrations ranging from 1 µM to 20 µM. Following 30 minutes of incubation, sepsis like (LPS treatment for 6 hours) or MI like (hypoxia for 3 hours) conditions were induced to determine the potential cardioprotective effect of the tested compounds. Creatine kinase (CK) and lactate dehydrogenase (LDH) activity were assayed to determine the level of cellular damage and cell protection effect. The experimental procedure is described in Materials and Methods above. Results are presented as CK and LDH release in arbitrary units (a.u.).

Figure 1B:
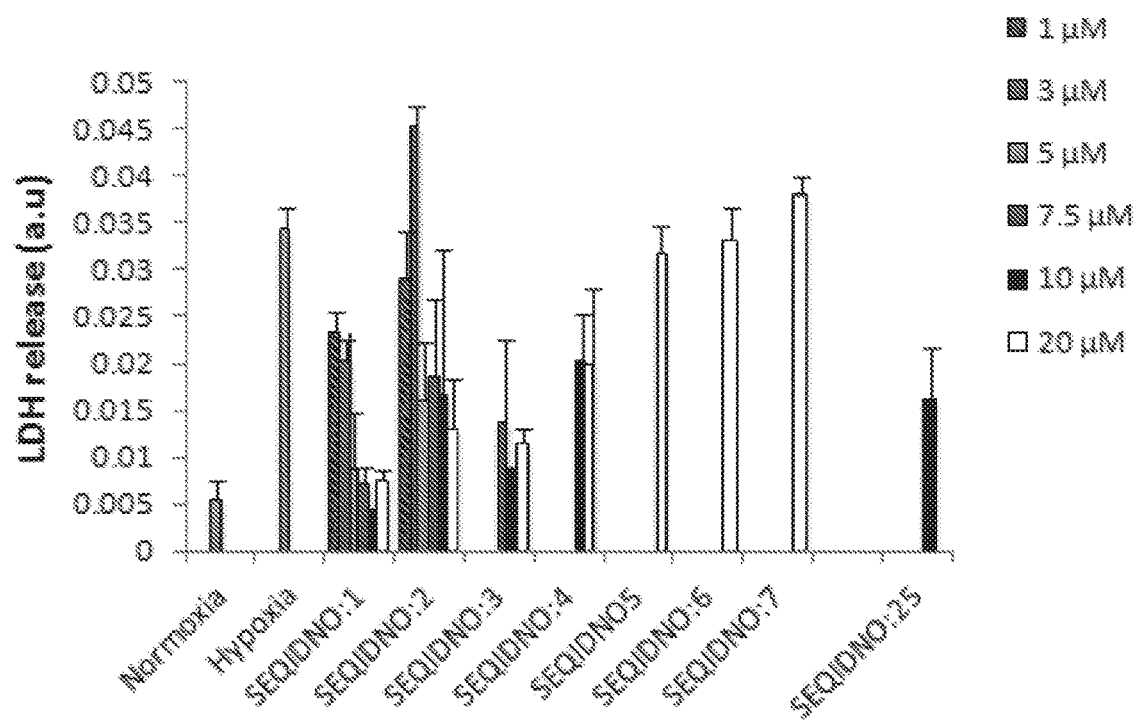

Four peptidomimetics of SEQ ID NOs:1-4 were found to be cardioprotective. They decreased the enzymatic activity of both CK and LDH enzymes in MI-like conditions (Hypoxia), as seen in FIGS. 1A and 1B, respectively. The N-acetylated peptide of SEQ ID NO:25 (10 µM) derived from the peptide disclosed in Piao et al., 2013 (supra) was used as a positive control. Peptidomimetic of SEQ ID NO:1 showed a dose-response dependent effect with minimal effective concertation at 1 µM. Peptidomimetics of SEQ ID NOs:2-4 presented cardioprotective activity at higher concertation (20 µM). Peptidomimetics of SEQ ID NOs:5-7 were not effective in preventing CK and LDH release even at 20 µM.

Figure 1C:
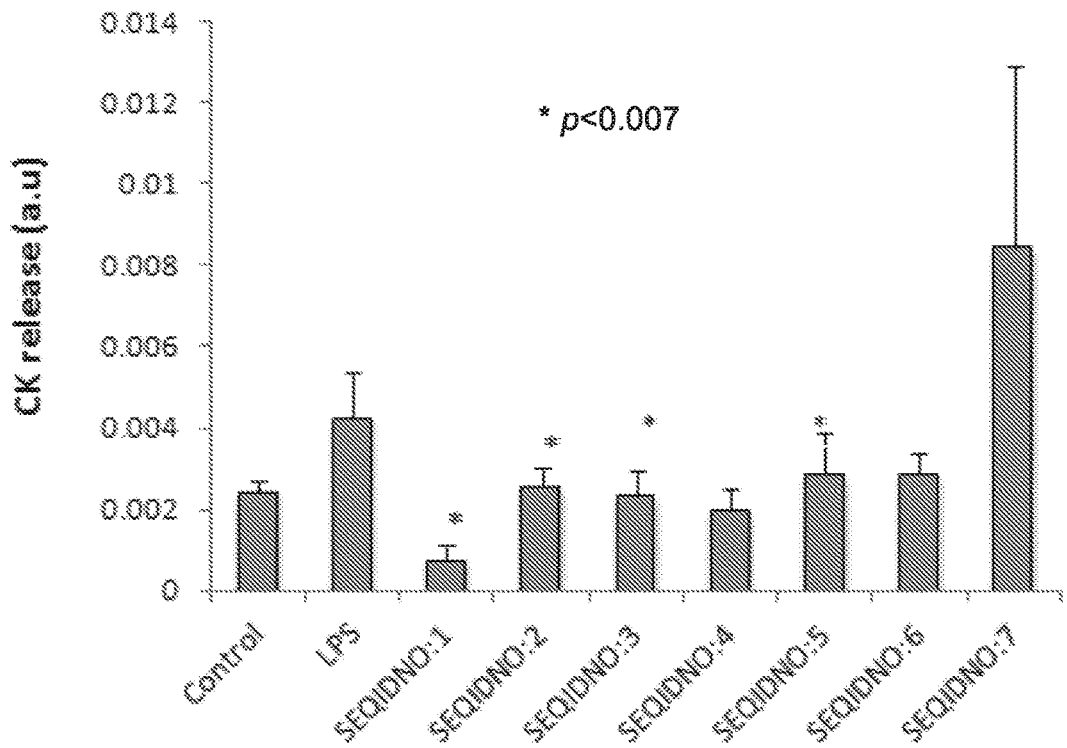
Figure 1D:
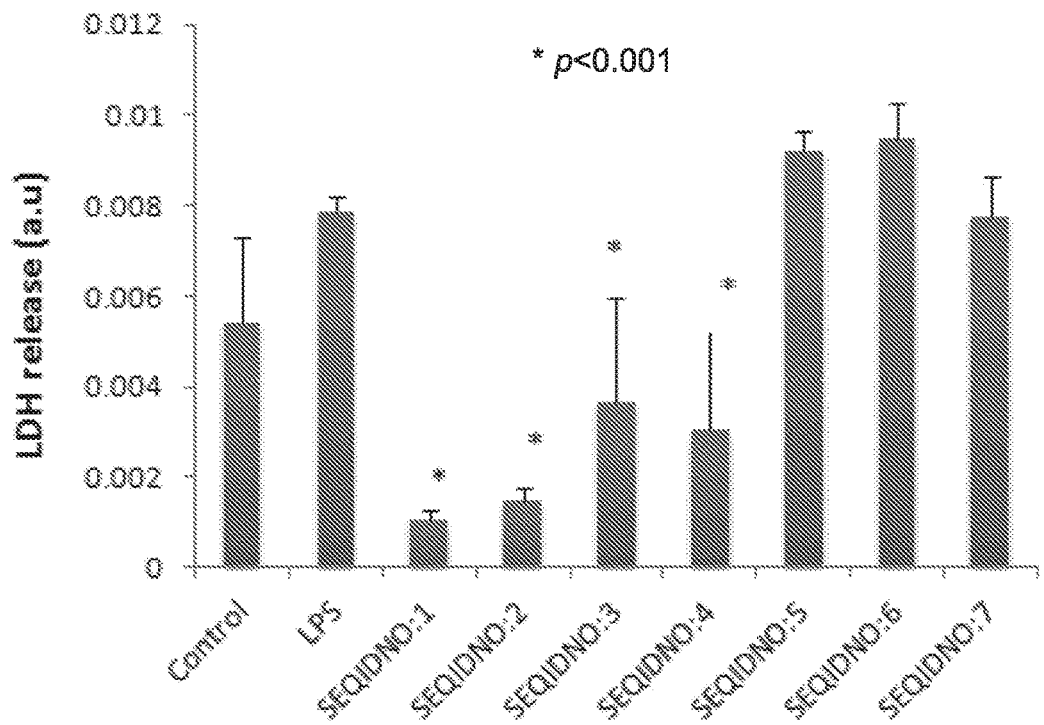

The four peptidomimetics of SEQ ID NOs:1-4 were found to confer cell protection under LPS treatment, as shown in FIGS. 1C and 1D, at a concertation of 20 µM. SEQ ID NO:1 was most effective, decreasing the release of both enzymes (LDH and CK) to subnormal levels.

Figure 2A:
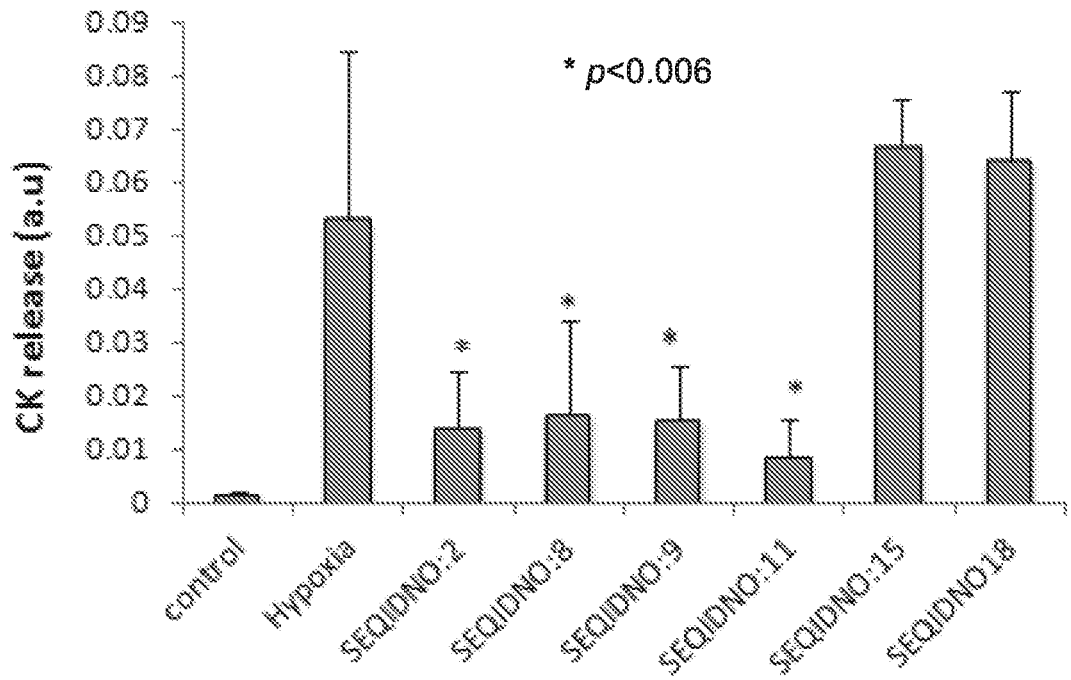
FIGS. 2A-2D are bar graphs showing the in vitro effect of peptidomimetics of SEQ ID NOs:1, 2, 8-16 and 18 on release of the enzymes CK and LDH by primary cardiomyocytes undergoing hypoxia (FIGS. 2A, 2B) or exposure to LPS t (FIGS. 2C, 2D). Primary cardiomyocytes undergoing hypoxia were pretreated with 10 µM of each of the indicated peptidomimetics. Release of CK and LDH is expressed in arbitrary units (a.u.)
Figure 2B:
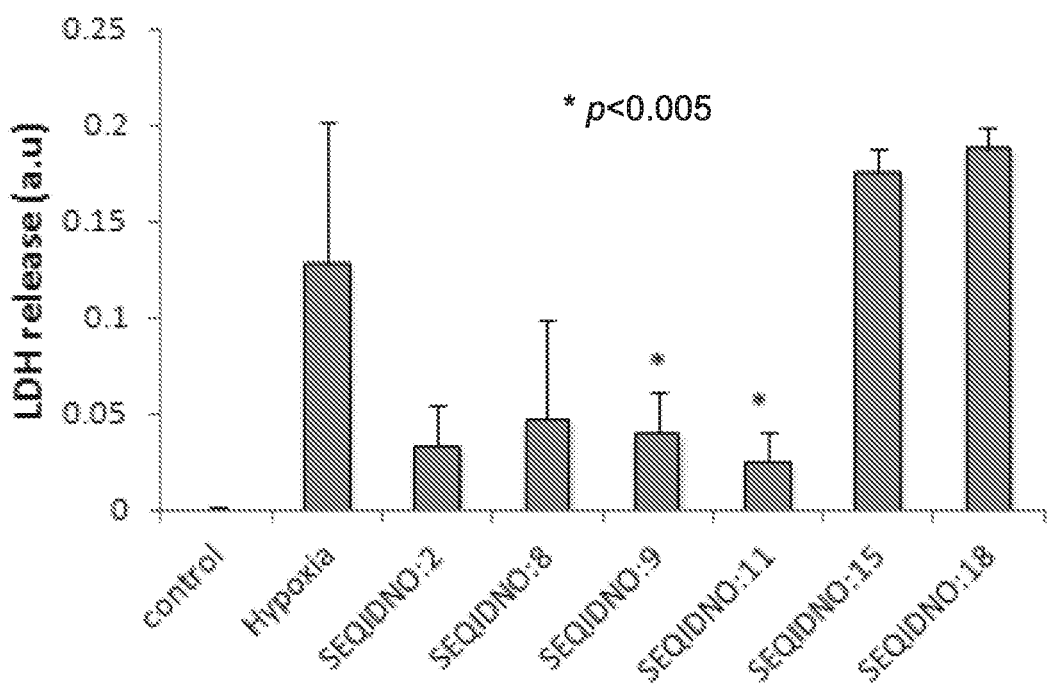

Peptidomimetics of SEQ ID NOs:8-16 and 18, which were synthesized based on scaffolds of SEQ ID NOs:1 and 2, were evaluated in vitro in identical cellular systems as described above. Exemplary results for CK and LDH release in primary cardiomyocytes treated with 10 µM of SEQ ID NOs:2, 8, 9, 11, 15 and 18 under hypoxia conditions are presented in FIGS. 2A and 2B, respectively. Peptidomimetics of SEQ ID NOs:8, 9 and 11, which were synthesized based on the scaffold of SEQ ID NOs:2, presented a substantial cell protective effect, comparable to that of SEQ ID NOs:2.

Figure 2C:
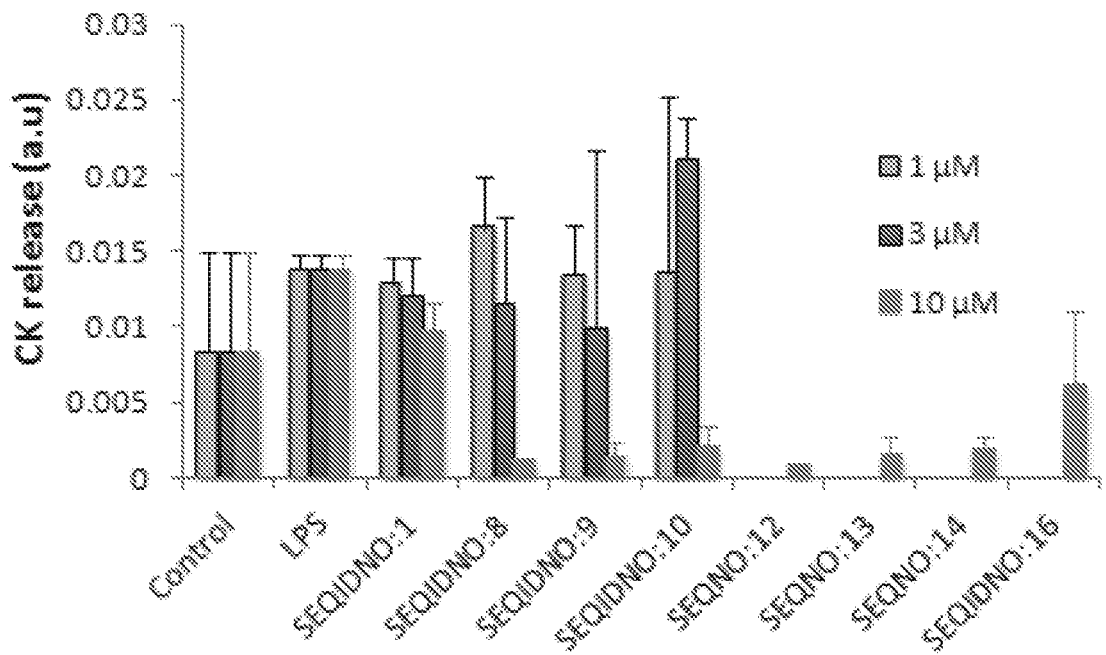
Figure 2D:
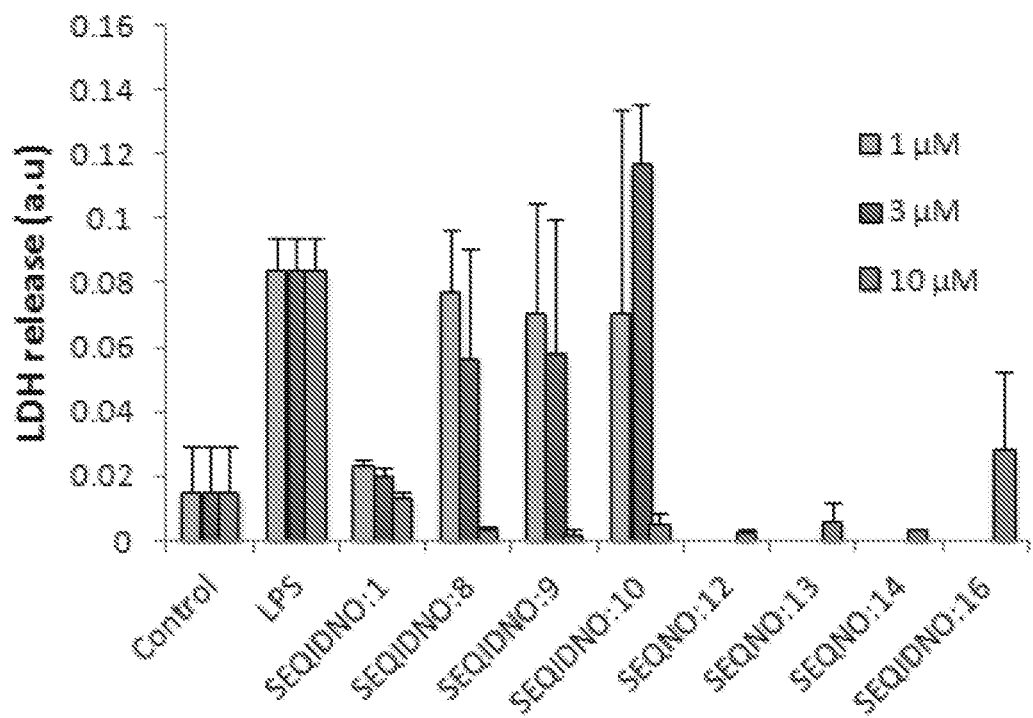

However, as seen in FIGS. 2C and 2D, when tested in the LPS system (i.e., under LPS stimulation), more prominent cellular protection was achieved at 10 µM concertation by decoy peptides designed based on the scaffolds of SEQ ID NOs:1-2 as compared to the parent SEQ ID NOs: 1.

Figure 3A:
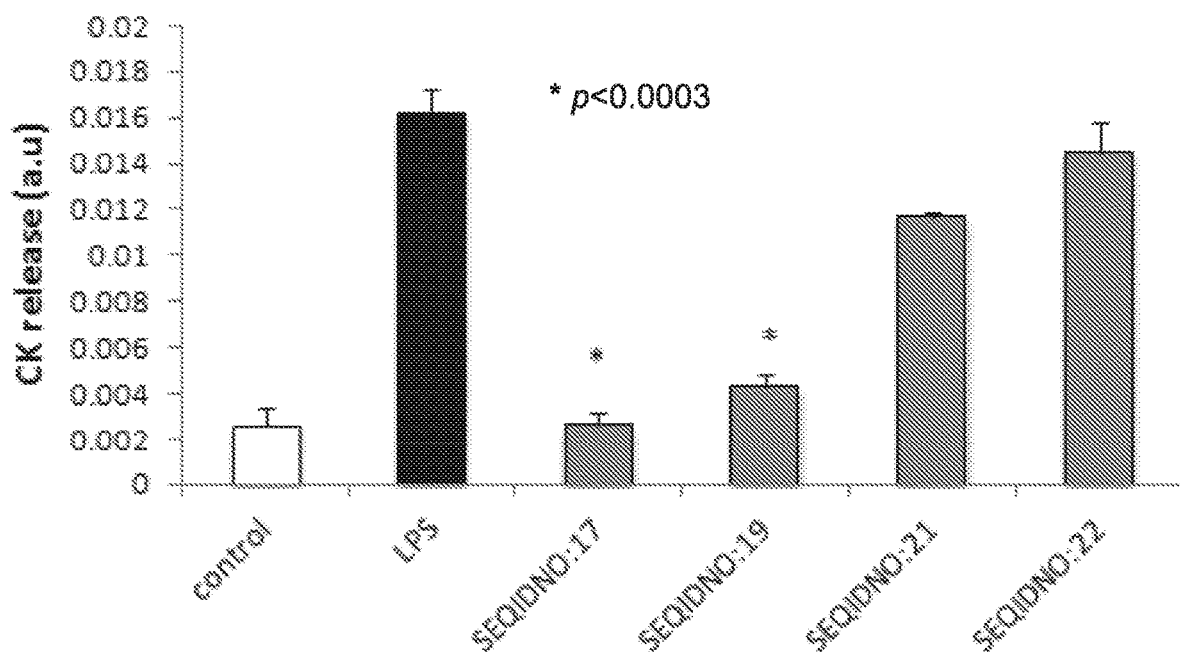
FIGS. 3A-3B are bar graphs showing the in vitro effect of peptidomimetics of SEQ ID NOs:17, 19, 21 and 22 (10 µM) on release of the enzymes CK and LDH by primary cardiomyocytes undergoing LPS treatment. Release of CK and LDH is expressed in arbitrary units (a.u.)
Figure 3B:
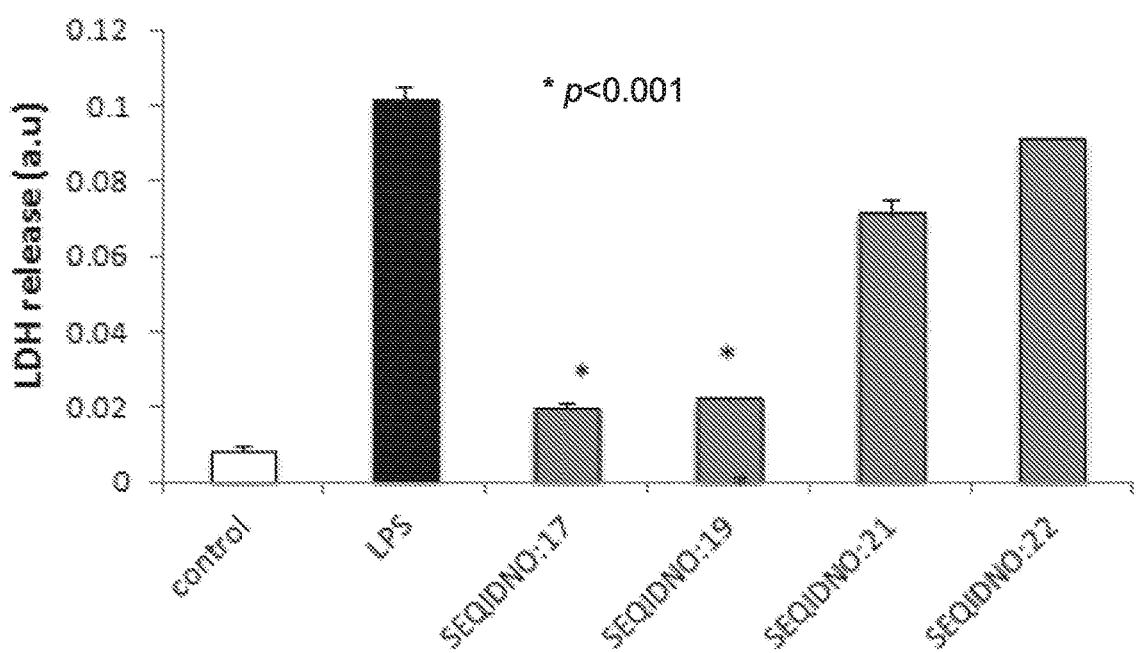

Another set of peptidomimetics presented by SEQ ID NOs: 17, 19-24, also synthesized based on the structures of SEQ ID NOs:1 and 2, were evaluated in vitro in identical cellular systems as described above. Results of exemplary peptidomimetics of SEQ ID NOs: 17, 19, 21 and 22 presented in FIGS. 3A-3B, demonstrate significant cytoprotective effect at 10 µM in the LPS system for SEQ ID NOs: 17 and 19.

Example 5

In Vitro Activity of Peptidomimetics of SEQ ID NOs:1, 2 and 12

The mechanism of action of peptidomimetics of SEQ ID NOs:1, 2 and 12 was studied in vitro in cardiomyocytes, under hypoxic conditions, by determining the expression level of the IκB gene, which is regulated by activation of TLR4, and by measuring the TLR4 mRNA levels. In addition, TLR4 expression level was measured in macrophage (derived from monocytes) treated with LPS.

All TLR signaling pathways culminate in activation of the transcription factor NF-κB, which controls the expression of an array of inflammatory cytokine genes. Under unstimulated conditions, NF-κB is sequestered in the cytoplasm as an inactive form by interaction with a family of inhibitor proteins known as inhibitory κB (IκB) proteins. NF-κB activation requires the phosphorylation and degradation of IκB proteins, which is triggered by two kinases, IκB kinase alpha (IKKα) and IκB kinase beta (IKKβ). Stimulation with TLR4 ligands triggers the rapid phosphorylation of specific serine residues of IκB proteins. Phosphorylated IκB proteins are subsequently polyubiquitinated and degraded by the 26S proteasome, allowing NF-κB to move into the nucleus. This pathway is called the 'canonical pathway' and is responsible for TLR-mediated induction of inflammatory cytokines such as tumor necrosis factor-α (TNF-α) and IL-6.

IκB protein level was determined by Western blot as described in Material and Methods. The amount of IκB was normalized via-a-vis the amount of β-actin serving as the loading control (the β-actin is coded by a housekeeping gene and its level is expected to remain constant under any experimental conditions).

As seen in FIGS. 4A-4B, high levels of IκB were obtained under treatment with both peptidomimetics of SEQ ID NOs:1 and 12, almost up to the level of normoxia, indicating that TLR4 activation was arrested and implying that less cytokines were produced under hypoxic condition as would be expected in absence of treatment with the peptidomimetics.

Next, peptidomimetics of SEQ ID NOs:1 and 2 were tested for their ability to affect the expression of TLR4. The level of TLR4 mRNA was measured by real-time reverse transcriptase polymerase chain reaction (RT-qPCR) method as described in Materials and Methods. The possible effect of both compounds on expression levels of TLR2 mRNA was used as a negative control. The results are presented in FIGS. 5A-5B.

Figure 5A:
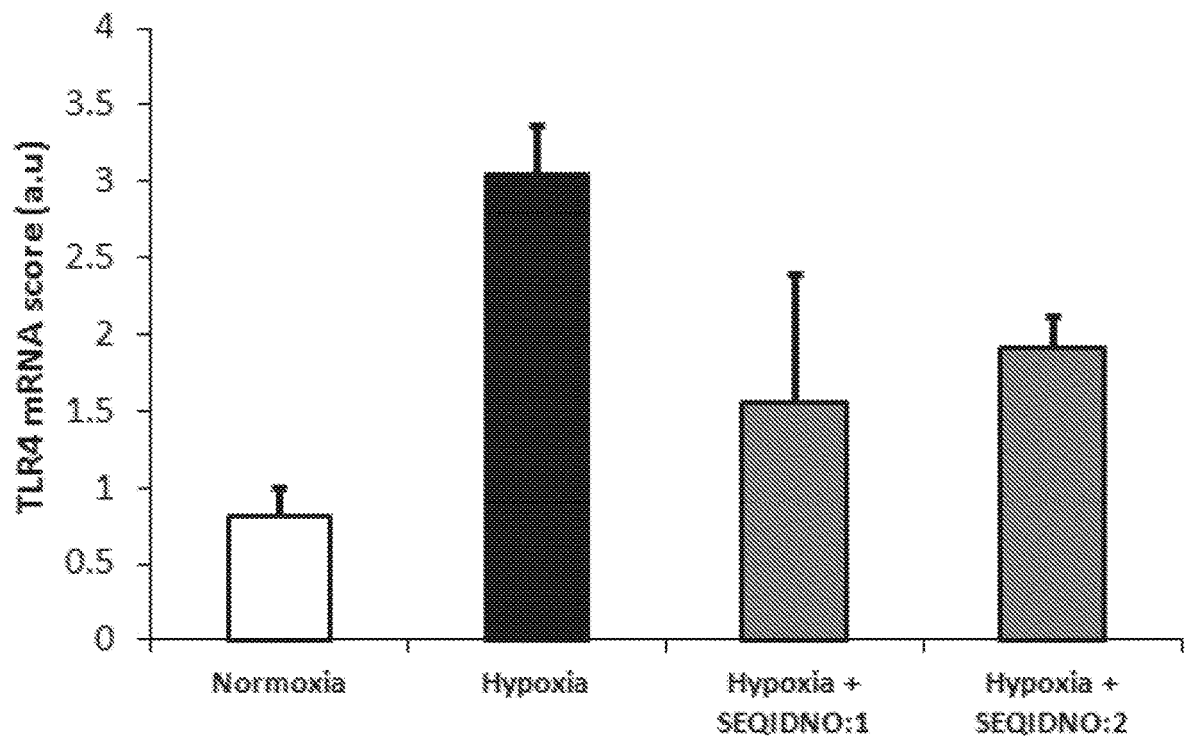
FIGS. 5A-5B are bar graphs showing the effect of peptidomimetics of SEQ ID NOs:1 and 2 on TLR4 mRNA level (FIG. 5A) and TLR2 mRNA level (FIG. 5B) in cardiomyocytes under hypoxic versus normal conditions. TLR mRNA scores are expressed in arbitrary units (a.u.)
Figure 5B:
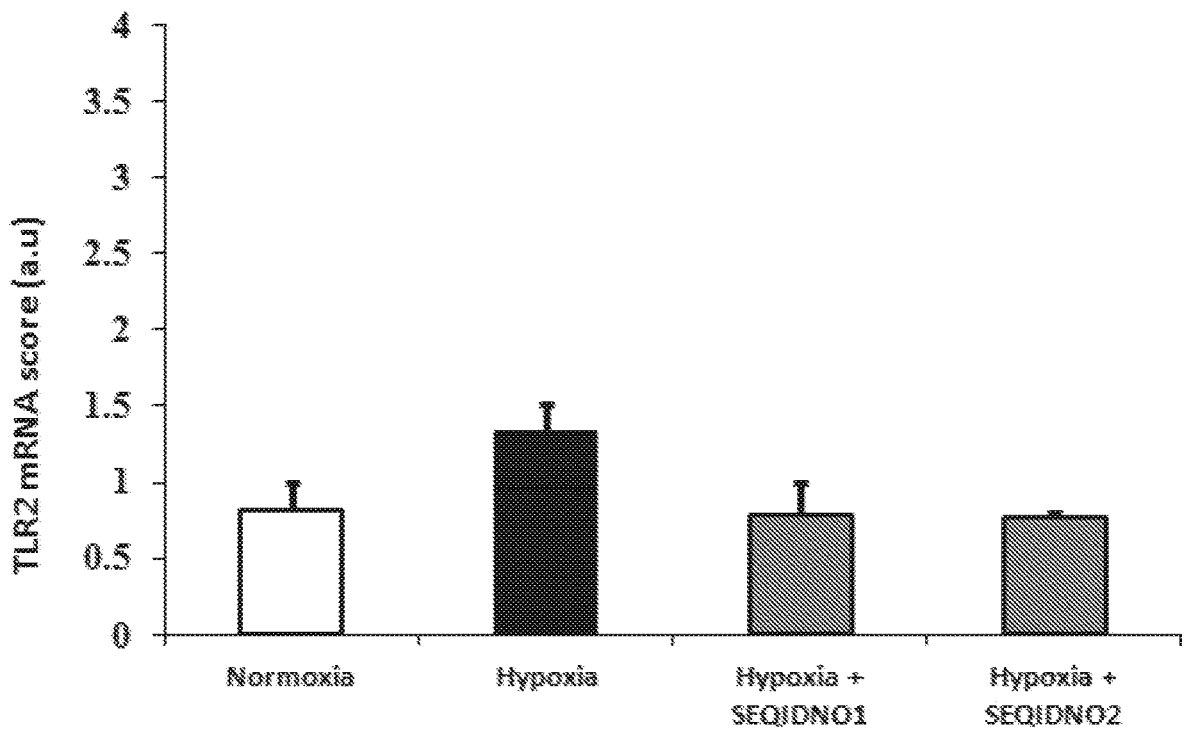

As shown in FIG. 5A, both decoy peptides significantly decreased TLR4 mRNA expression level under hypoxic conditions, whereas expression levels of TLR2 mRNA was relatively unaffected by these peptides (FIG. 5B). These results demonstrate that the effect of peptidomimetics SEQ ID NOs:1 and 2 is at least partially mediated by TLR4.

Finally, FACS analysis to test the expression of TLR4 protein by macrophages under LPS treatment in the presence or absence of peptidomimetics of SEQ ID NOs:1 and 2 was conducted (as described in Materials and Methods). The peptidomimetic of SEQ ID NO:25 was used as a positive control. The decoy peptides were administered to the macrophages 30 min before introducing LPS to the system. Then, macrophages were incubated with LPS for 4 hours.

Two LPS concentrations were applied: high (20 μg/ml) and low (100 ng/ml). Decoy peptides were used in concentration of 10 μM. Eleven test groups were employed: (1) nontreated macrophages (control); (2) macrophages treated with SEQ ID NO:1 without exposure to LPS (SEQ ID NO:1); (3) macrophages treated with SEQ ID NO:2 without exposure to LPS (SEQ ID NO:2); (4) macrophages exposed to low concentration of LPS but not treated with a decoy peptide (LPS low 100 ng/ml); (5) macrophages exposed to high concentration of LPS but not treated with a decoy peptide (LPS high 20 μM/ml); (6) macrophages treated with SEQ ID NOD and exposed to high concentration of LPS (LPS high+SEQ ID NOD); (7) macrophages treated with SEQ ID NOD and exposed to high concentration of LPS (LPS high+SEQ ID NOD); (8) macrophages treated with SEQ ID NO:25 (10 μM) and exposed to high concentration of LPS (LPS high+SEQ ID NO:25); (9) macrophages treated with SEQ ID NO: 1 and exposed to low concentration of LPS (LPS low+SEQ ID NOD); (10) macrophages treated with SEQ ID NOD and exposed to low concentration of LPS (LPS low+SEQ ID NOD); and (11) macrophages treated with SEQ ID NO:25 (10 μM) and exposed to low concentration of LPS (LPS low+SEQ ID NO:25). Flow cytometry histograms showing the amount (count) of TLR4 expressed by the macrophages in the different test groups are depicted in FIGS. 6A-6C. The LACS results from all experiments are summarized in FIG. 6D.

As seen in FIG. 6A, following LPS challenge, TLR4 was highly expressed in the macrophages not treated with a decoy peptide (test groups 4 and 5) (2 folds compared to controls). However, as seen in FIGS. 6B-6C, administration of LPS to macrophages pre-treated with SEQ ID NOD or 2 shifted the TLR4 expression level to the left and toward baseline levels (tests groups 6, 7, 9 and 10). No difference in the effects of either SEQ ID NOD or 2 was observed between low and high concentration of LPS. In addition, decoy peptides of SEQ ID NOs:1 and 2 were more effective than the prior art decoy peptide (SEQ ID NO: 25) in lowering the expression of TLR4 in the presence of LPS (test groups 8 and 11). These results, when accumulated in FIG. 6D, strengthen the findings that decoy peptides such as SEQ ID NOs:1 and 2 abolish physiological TLR4 elevation following LPS exposure and are superior to known decoy peptides.

Example 6

In Vitro Activity of Compounds PM2 and PM6

Decoy peptides represented by compounds PM1-PM10 were tested in vitro for their ability to decrease the level of CK and LDH released by stressed cardiomyocytes following exposure to LPS or hypoxic stimulation, and further evaluated for their ability to affect the level of IL-1β and TLR4 mRNA, and expression of IκB and TLR4 proteins, according to the protocols described in Materials and Methods and in Example 5 herein above.

Figure 7A:
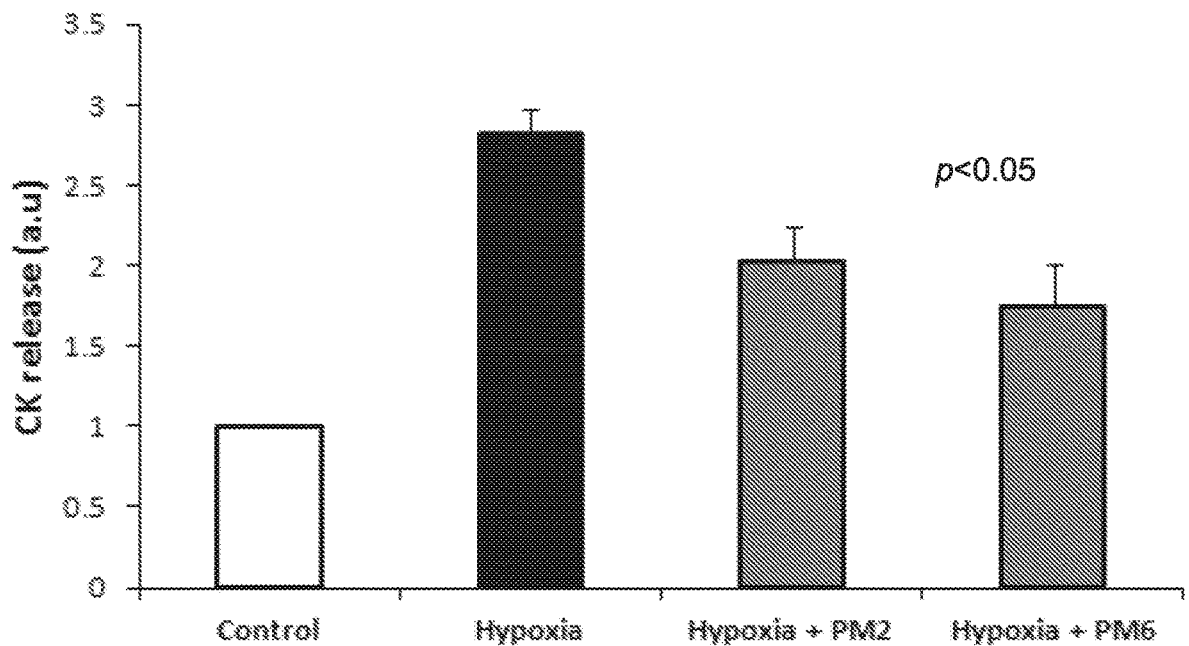
FIGS. 7A-7D are bar graphs showing the effect of exemplary decoy peptides PM2 and PM6 on CK and LDH release by cardiomyocytes undergoing hypoxic stimulation (FIGS. 7A and 7B, respectively) or exposure to LPS stimulation (FIGS. 7C and 7D, respectively). Control are untreated cells. Release of CK and LDH is expressed in arbitrary units (a.u.)
Figure 7B:
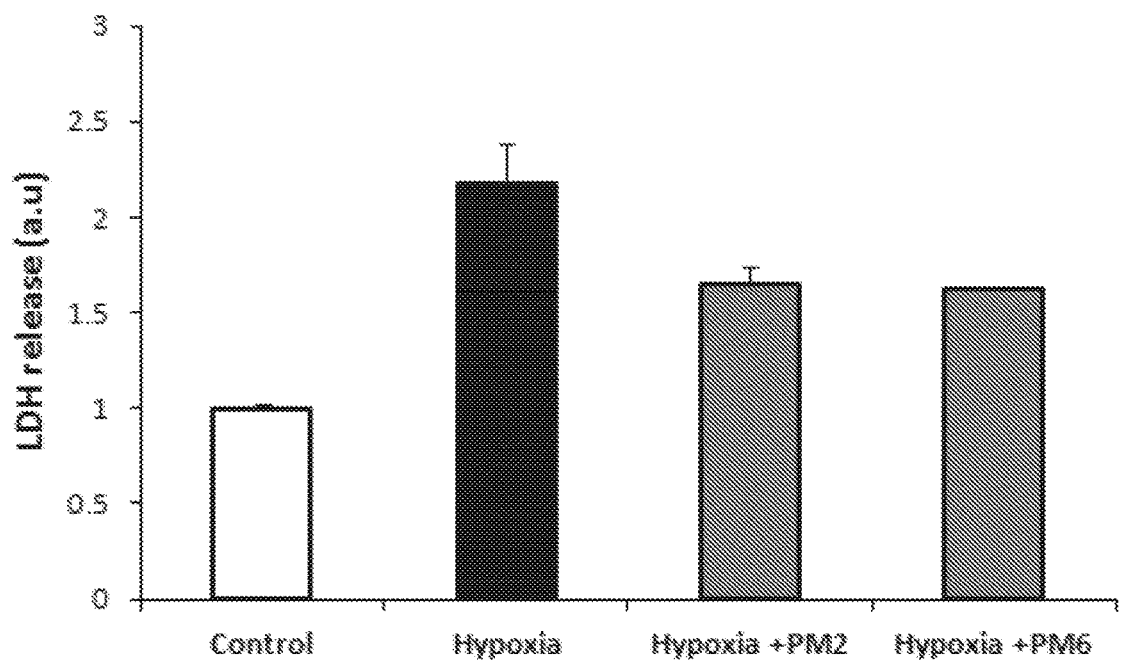
Figure 7C:
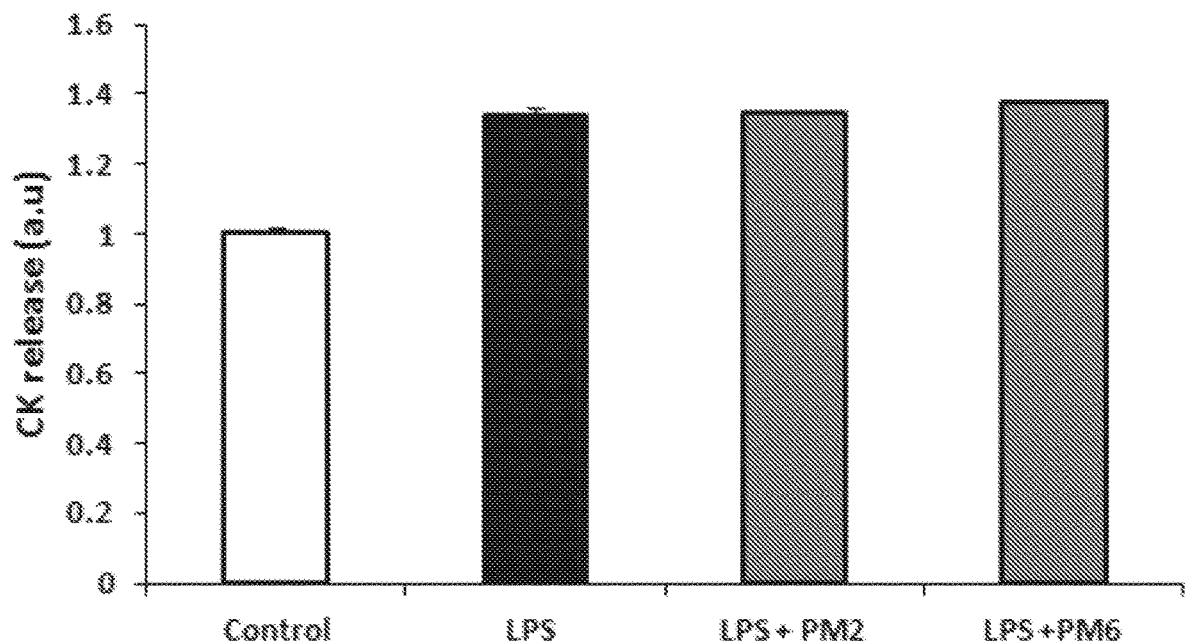
Figure 7D:
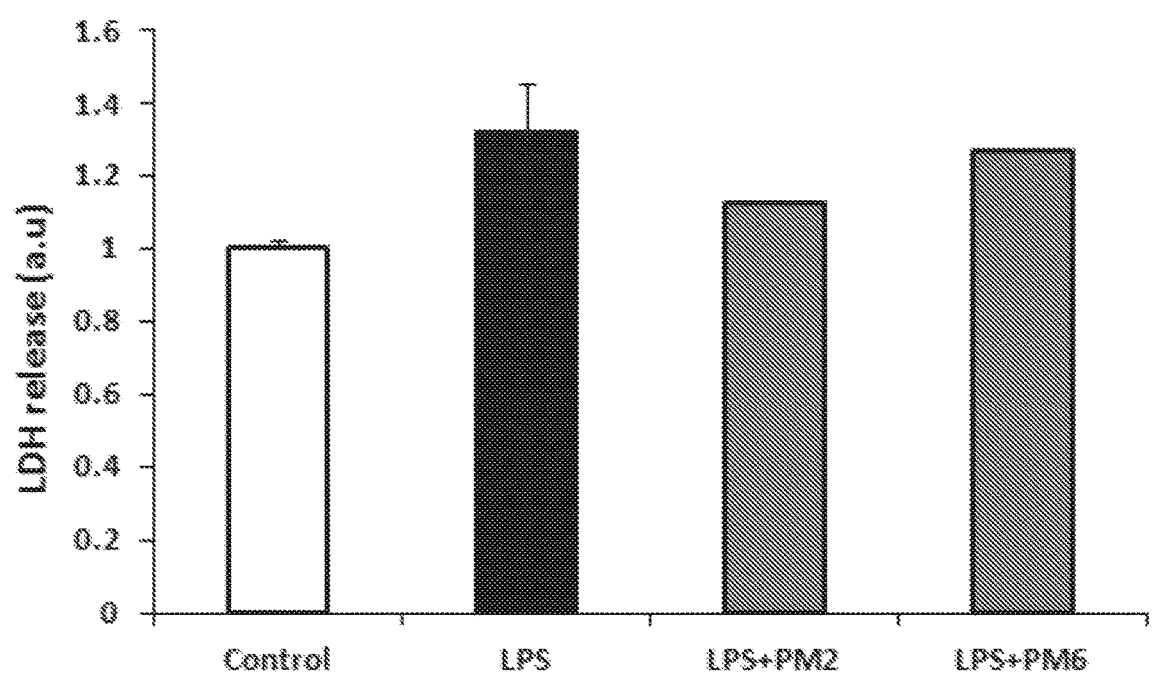

Exemplary results for two compounds, PM2 and PM6 (20 μM each), tested for their ability to affect CK and LDH release are presented in FIGS. 7A-7D. As seen in the figures, both PM2 and PM6 conferred a significant reduction in the level of both CK and LDH (FIGS. 7A and 7B, respectively), release under hypoxia conditions, but had no significant effect on CK and LDH levels in the LPS assay (FIGS. 7C, 7D respectively).

Figure 8A:
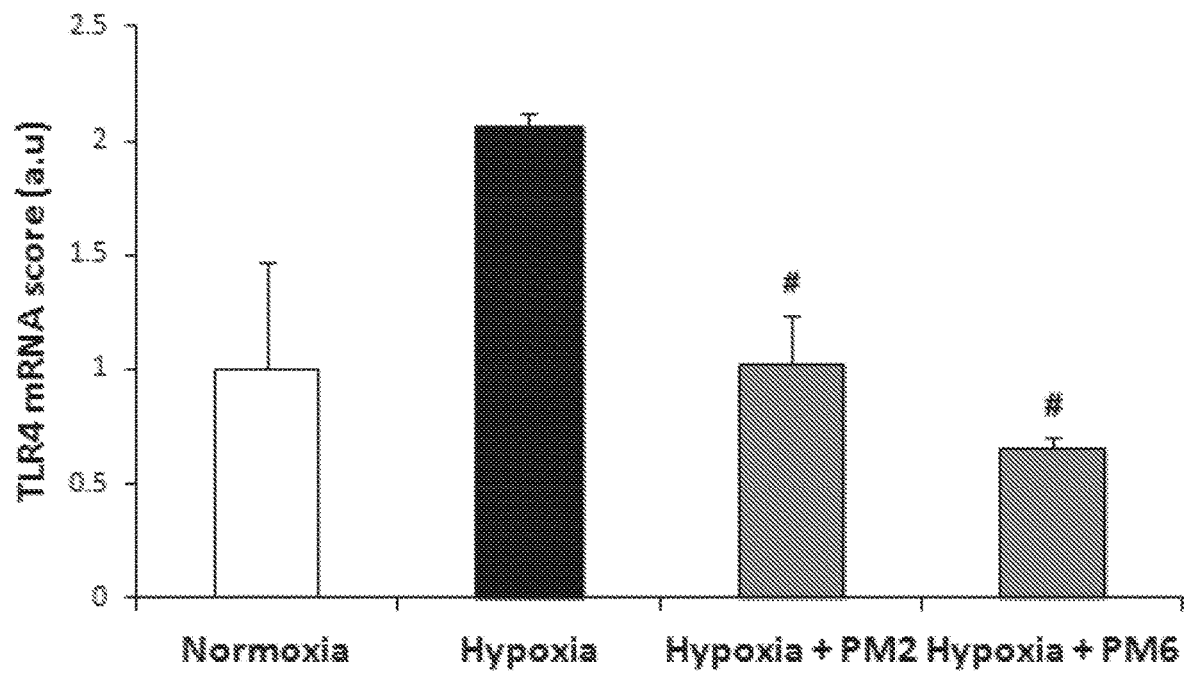
FIGS. 8A-8B are bar graphs showing the effect of exemplary decoy peptides PM2 and PM6 on TLR4 and IL-1β mRNA levels (8A and 8B, respectively) in hypoxic cardiomyocytes. TLR4 and IL-1β m RNA scores are expressed in arbitrary units (a.u.)
Figure 8B:
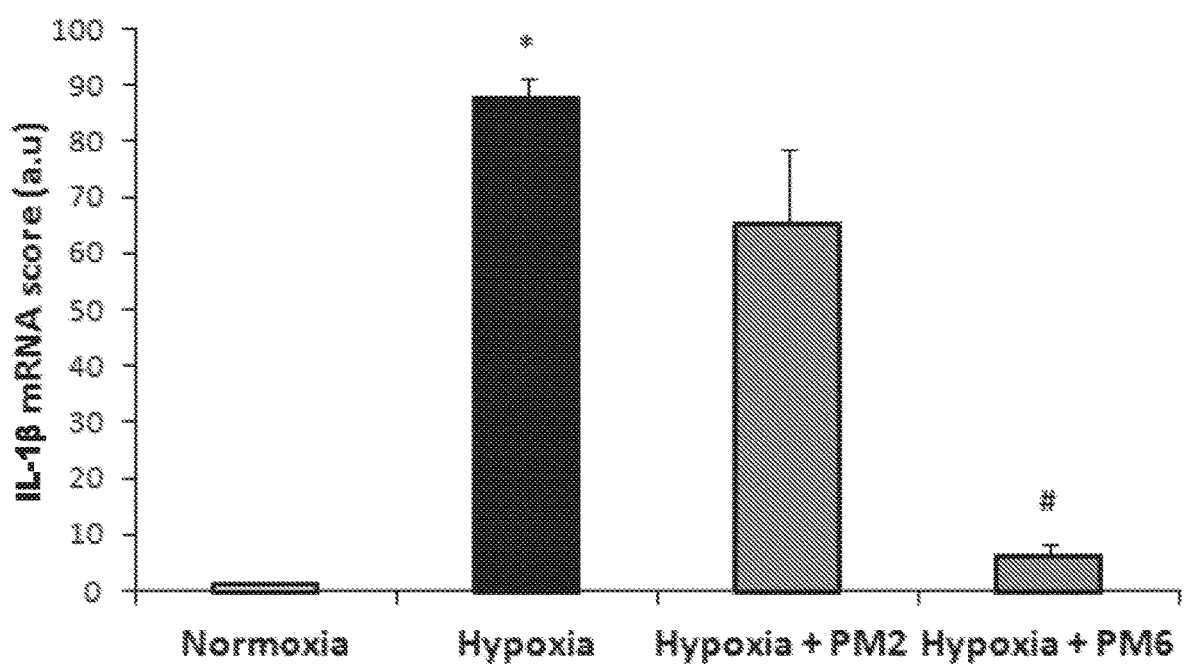

Exemplary results for PM2 and PM6 tested for their ability to affect mRNA levels of TLR4 and IL-1β in cardiomyocytes under hypoxic conditions are presented in FIGS. 8A-8B. As seen in these figures, both PM2 and PM6 conferred significant decrease in mRNA levels of TLR4 and IL-1β, wherein PM6 inhibited mRNA production approximately by 3.3-fold and by 12-fold for TLR4 and IL-1β, respectively, and PM2 inhibited mRNA production by 2-fold and 1.3-fold for TLR4 and IL-1β, respectively, under hypoxic conditions.

Figure 9A:
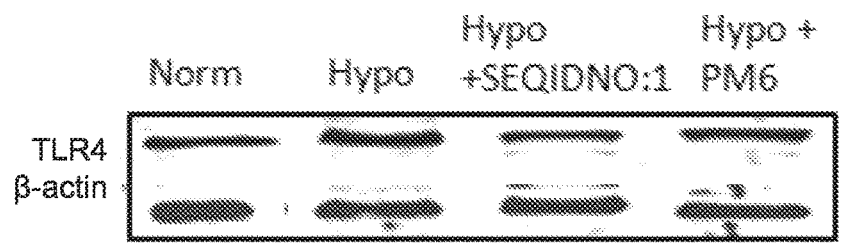
FIGS. 9A-9D are Western blot presentation (FIGS. 9A, 9C) and bar graph (FIGS. 9B, 9D) showing the effect of exemplary decoy peptides PM6 and SEQ ID NO:1 on TLR4 protein level (FIGS. 9A-9B), and the effect of PM6 on IκB protein level (FIGS. 9C-9D) in hypoxic cardiomyocytes. β-actin level was used as internal control. Proteins levels are expressed in arbitrary units (a.u.)
Figure 9B:
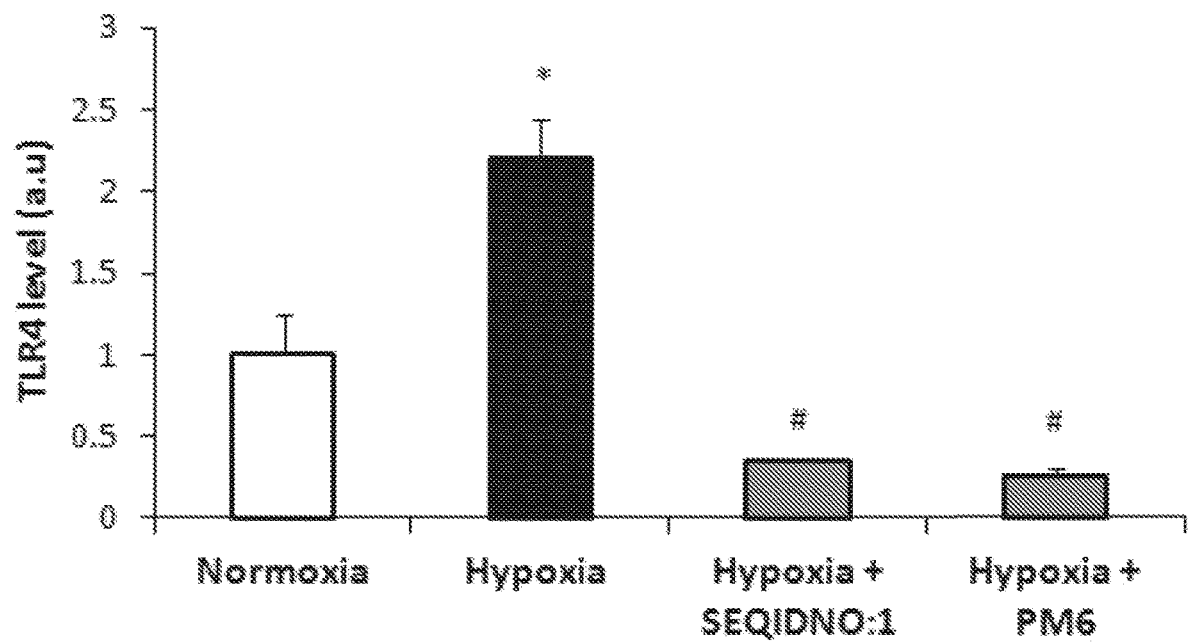

A possible effect of PM6 (20 μM) on TLR4 protein expression under hypoxic conditions was tested and compared to the effect of decoy peptide SEQ ID NO:1 (20 μM) serving as a positive control. As seen in FIGS. 9A-9B, under hypoxic conditions, PM6 significantly decreased (by 7.6-fold) expression of TLR4, to the same extent as SEQ ID NO: 1.

Figure 9C:
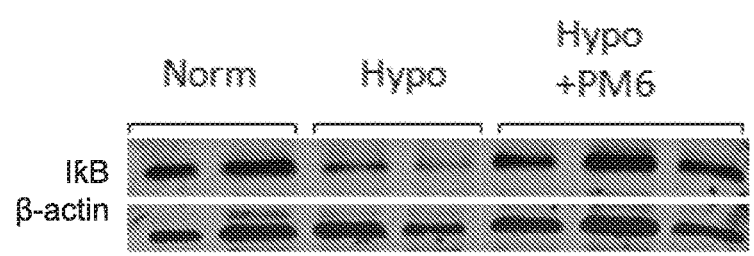
Figure 9D:
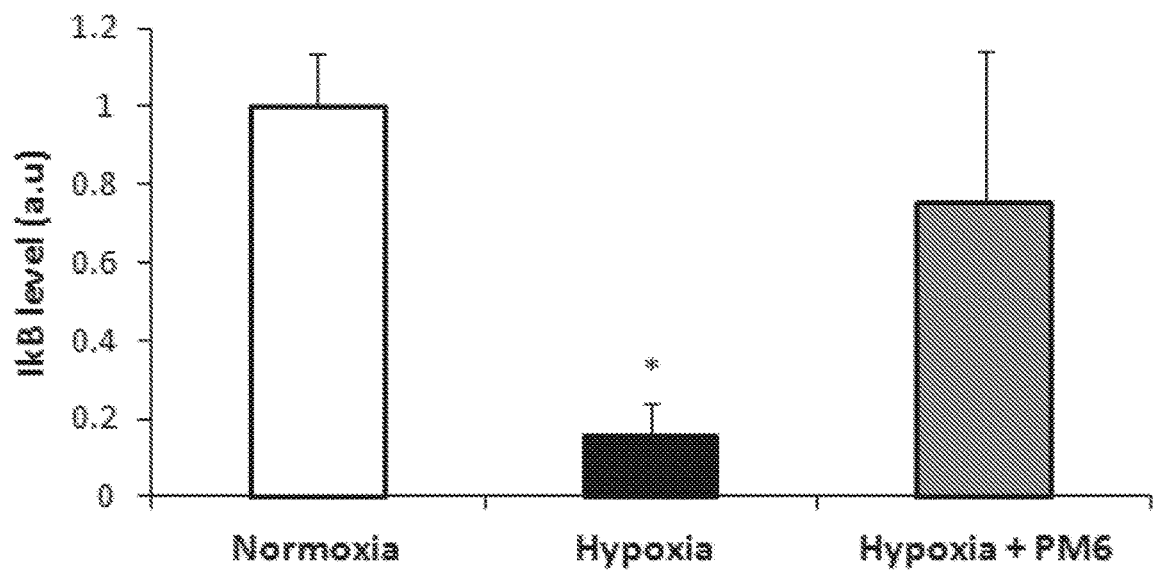

Finally, the effect of 20 μM PM6 on IκB protein level was tested. As seen in FIGS. 9C-9D, PM6 inhibited decrease of IκB protein level in treated hypoxic cardiomyocytes by roughly 7-fold compared hypoxic cells not treated with PM6.

Example 7

In Vivo Study

Myocardial infarction (MI) in animals may be mimicked by a procedure called left anterior descending artery (LAD) ligation, described in Materials and Methods above. A pilot dose response experiment was first conducted. Decoy peptide represented by compound PM6 (0.5, 1.0 and 5.0 mg/kg) or aqueous solution of 40% polyethylene glycol (PEG 600) were administered intravenously (IV) to C57BL mice, 1 hour before LAD ligation. All mice were kept under standard animal facility conditions for 24 hours. The heart infarct size was measured in all three groups.

Figure 10:
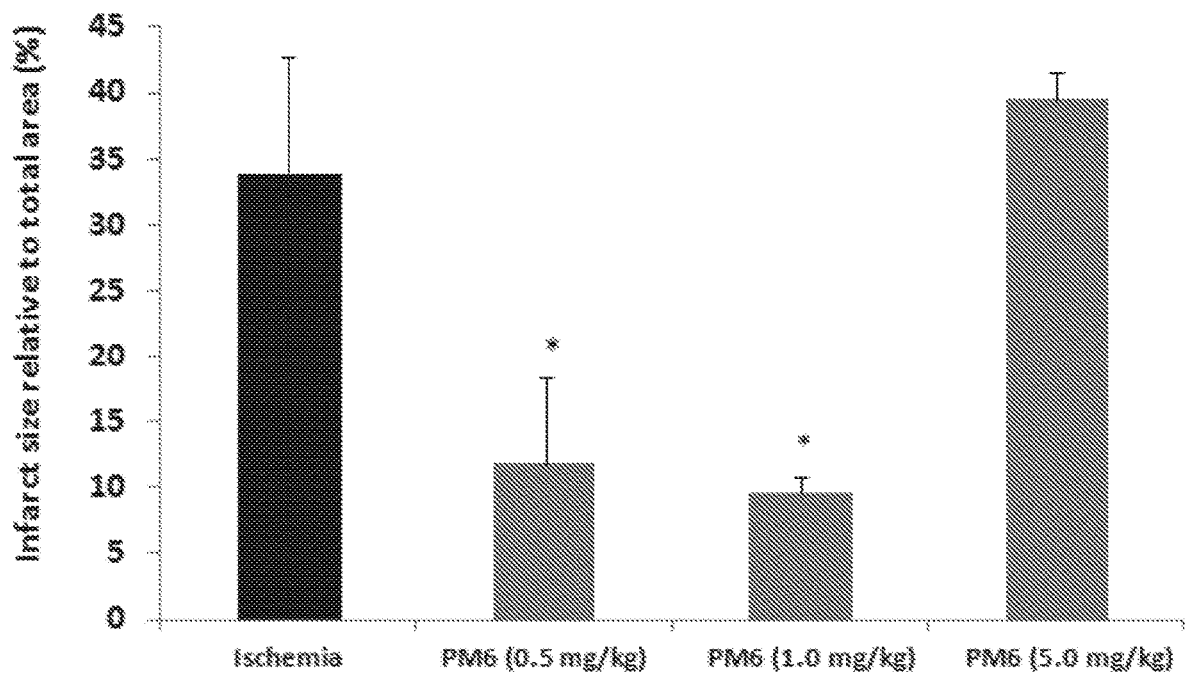
FIG. 10 is a bar graph showing the effect of decoy peptide PM6 on infarct size in the left ventricular. Various concentration of PM6 were administrated to C57BL mice 1 hour before inducing ischemia. The "Ischemia" column represents ischemic mice not treated with decoy peptide PM6 (control)

Surprisingly, as seen in FIG. 10, a significant effect on the size of the infarct was obtained in PM6 low dose (0.5 mg/kg) treated mice.

A dose response experiment was conducted using the experiment design of the pilot experiment. PM6 was given to mice in three doses: 0.05, 0.30 and 1.00 mg/kg. Blood levels of four serum markers were assessed. The levels of three markers CK, LDH and troponin were correlated with MI severity. Troponin is a complex of three regulatory proteins that is integral to muscle contraction in skeletal muscle and cardiac muscle, and serves as a highly specific marker for myocardial infarction or heart muscle cell death. The level of the fourth marker GOT was used as an indicator for liver functions.

Figure 11:
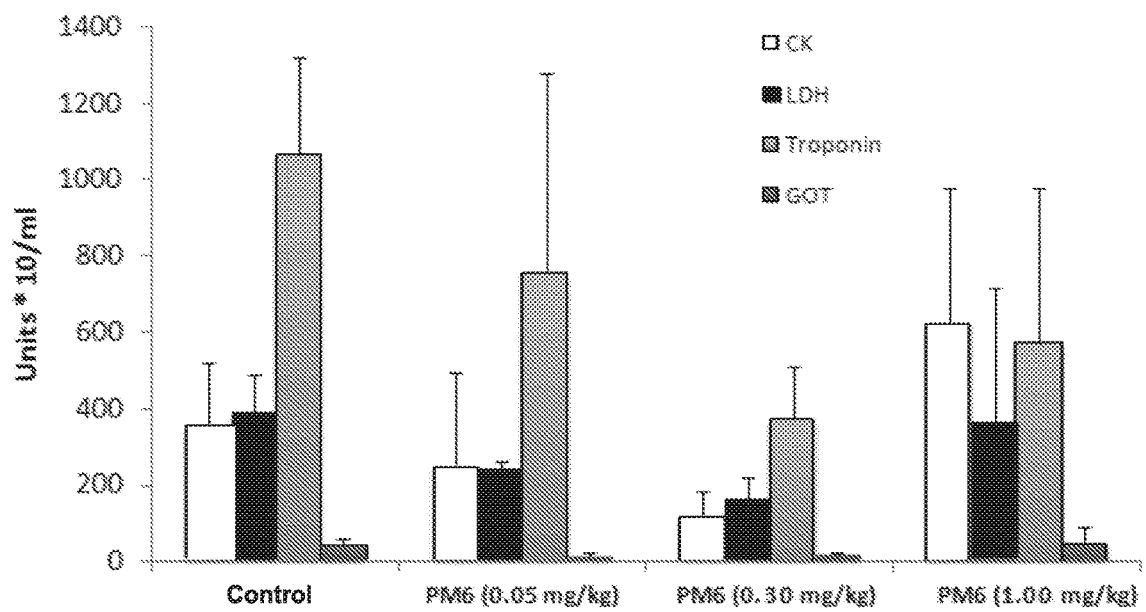
FIG. 11 is a bar graph showing the dose response effect on levels of the MI markers CK, LDH and troponin, and liver marker GOT, exerted by exemplary decoy peptide PM6 administrated 1 hour before inducing ischemia in a MI mice model. Control are ischemic mice not treated with PM6.

As seen in FIG. 11, PM6 did not affect GOT level in all three doses, meaning that no damage was observed in liver function as a result of drug administration. All three MI markers were significantly reduced by PM6 in ischemic mice treated with 0.3 mg/kg dose.

Figure 12:
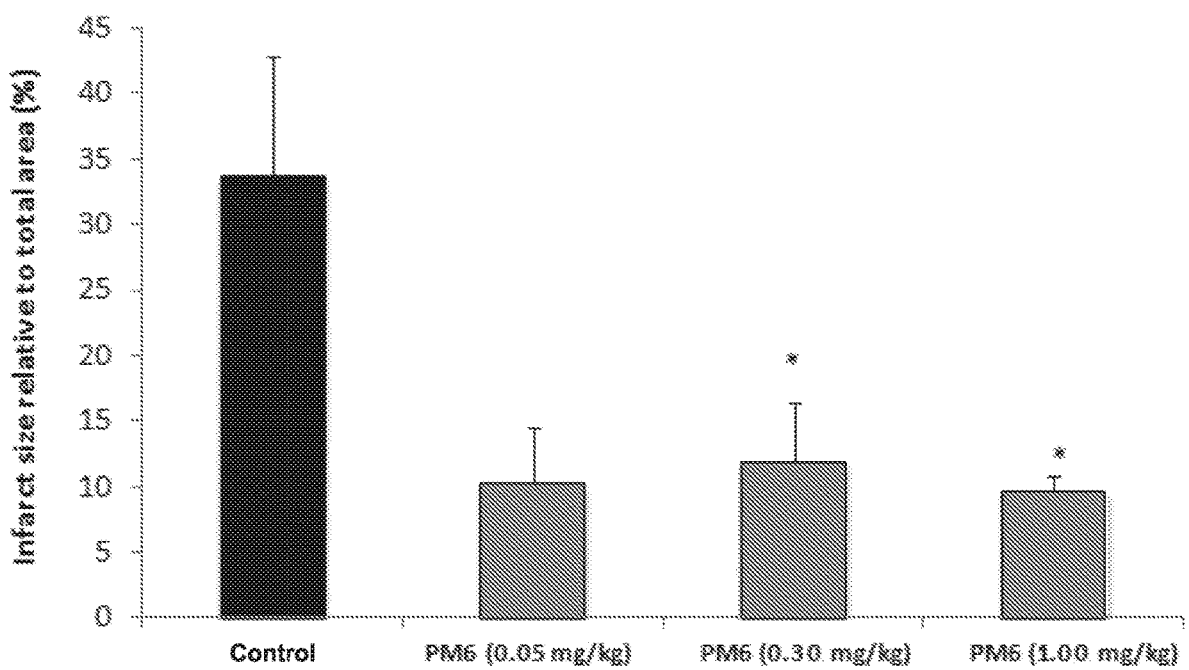
FIG. 12 is a bar graph showing the dose response effect of exemplary decoy peptide PM6 on infarct size in the left ventricular of ischemic mice. PM6 was administrated 1 hour before inducing ischemia in a MI mice mode. Control are ischemic mice not treated with PM6.

Heart infarct size was significantly reduced in mice treated with either 0.05, 0.30 or 1.00 mg/kg PM6, as seen in FIG. 12.

Next, a time course experiment was conducted with 0.3 mg/kg of PM6 administered at 3 time-points: 30 min, 1 h and 2 h before LAD ligation. The experiment was designed identically to the dose response experiments described above. The results are shown in FIGS. 13 and 14.

Figure 13:
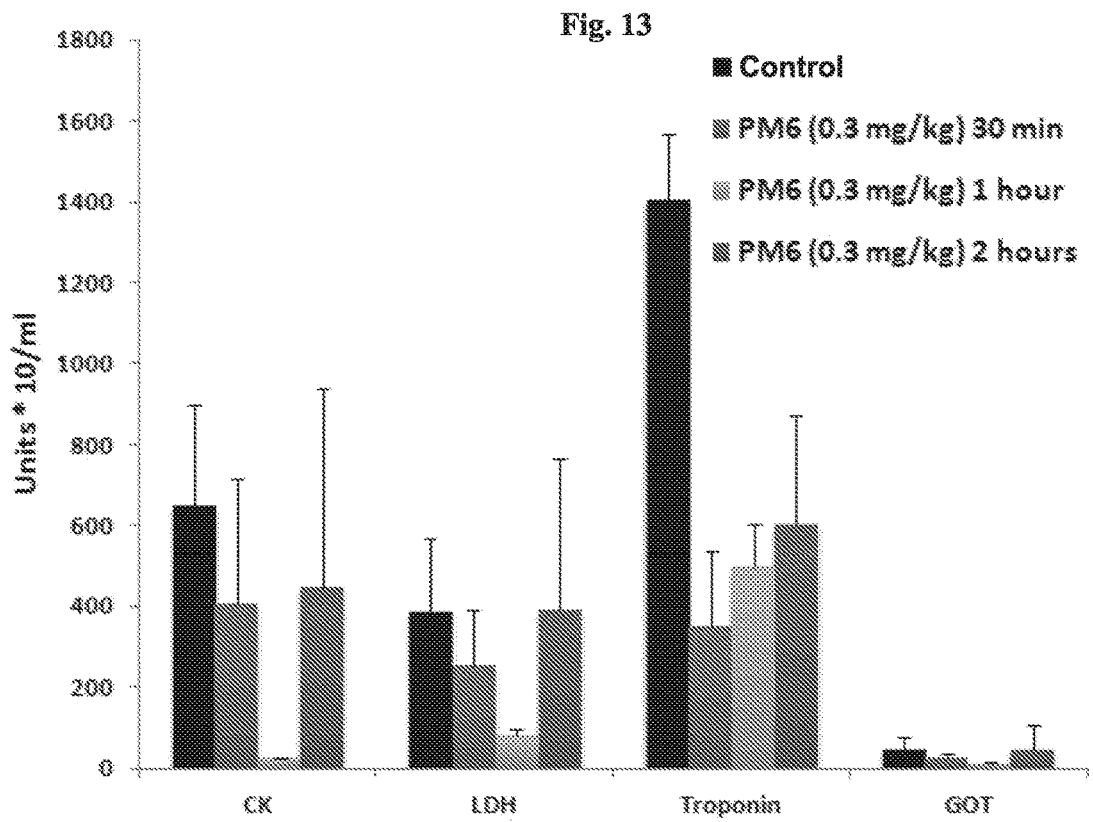
FIG. 13 is a bar graph showing the time course effect of exemplary decoy peptide PM6 on levels of MI markers CK, LDH and troponin, and liver marker GOT in ischemic mice. PM6 was administrated 2 h, 1 h or 30 min before inducing ischemia. Control are ischemic mice not treated with PM6.
Figure 14:
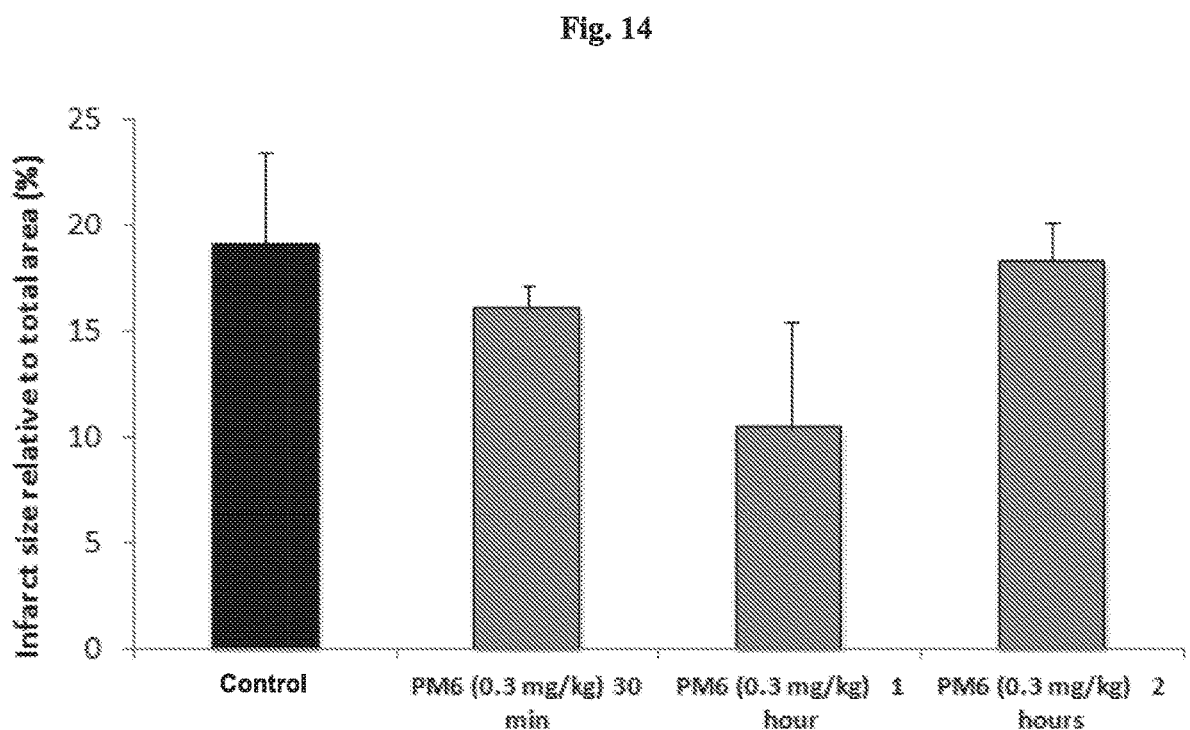
FIG. 14 is a bar graph showing the time course effect of exemplary decoy peptide PM6 on infarct size of the left ventricular of the mice. PM6 was administrated 2 h, 1 h or 30 min before inducing ischemia in a MI mice model. Control are ischemic mice not treated with PM6.

As seen in FIG. 13, administration of the exemplary decoy peptide PM6 1 hour prior to LAD ligation resulted in significant reduction of all three MI blood markers. As seen in FIG. 14, a dose of 0.3 mg/kg administered 1 h before ligation was significantly effective in reducing the infarct size.

Myocardial infarction is a phenomenon, which occurs suddenly and unexpectedly not enabling the provision of a preventive cardioprotective treatment. Thus, cardioprotective drug may be given to a patient only after being diagnosed as undergoing a cardiac attack. The ability of decoy peptides described herein to confer cardio protection after LAD ligation (mimicking the real MI in humans) was tested. Exemplary decoy peptide PM6 (0.3 mg/kg) was injected IV one hour after ligation. Blood levels of CK, LDH and GOT were tested 24 h and 7 days after ligation.

Figure 15A:
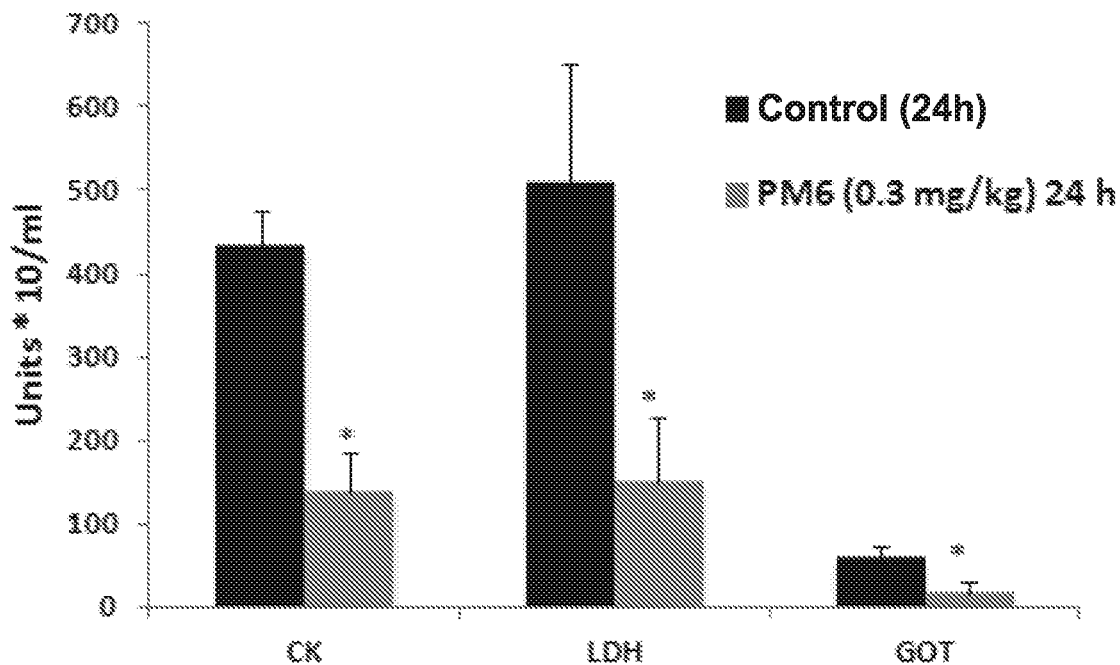
FIGS. 15A-15B are bar graphs showing the effect of intravenous administration of an exemplary decoy peptide PM6 (0.3 mg/kg) 1 hour after inducing ischemia in mice on levels of MI markers CK and LDH and liver marker GOT, as measured 24 h (FIG. 15A) and 7 days (FIG. 15B) after the ischemic event. Control are ischemic mice not treated with PM6.
Figure 15B:
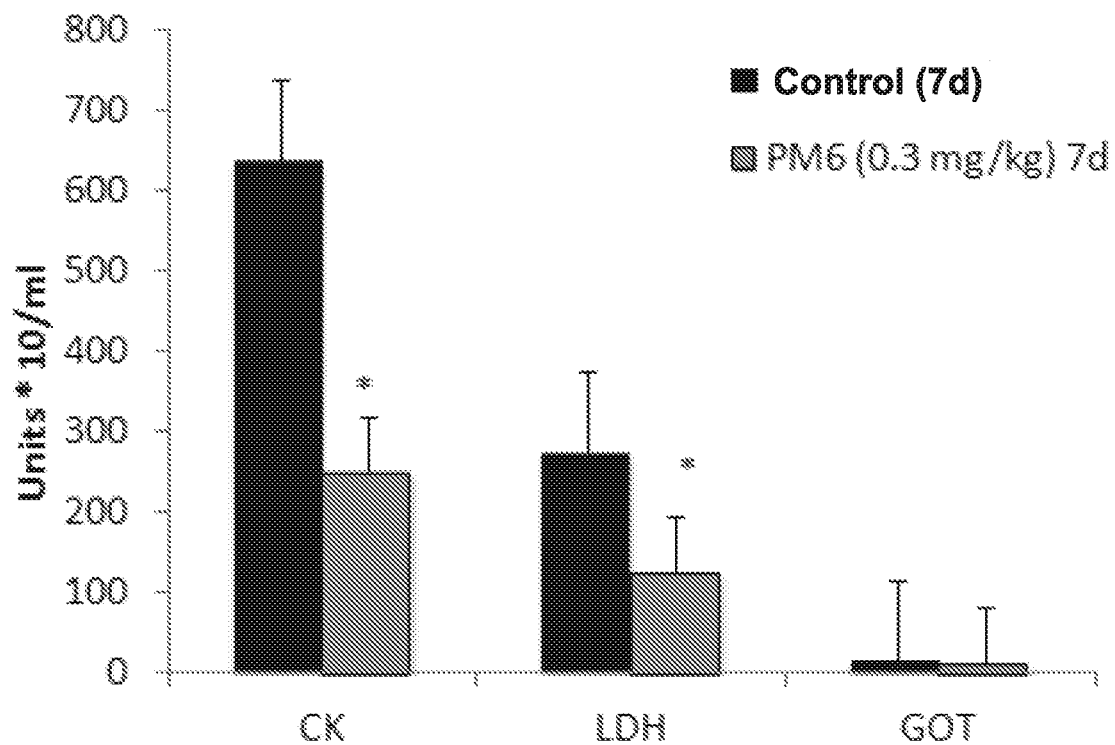

As seen in FIGS. 15 A and 15B, surprisingly, a very impressive down regulation in blood levels of both cardio damage markers (CK and LDH) was obtained 24 hours (FIG. 15A) as well as and 1 week (FIG. 15B) after treatment with PM6. The level of GOT did not changed dramatically.

Figure 16A:
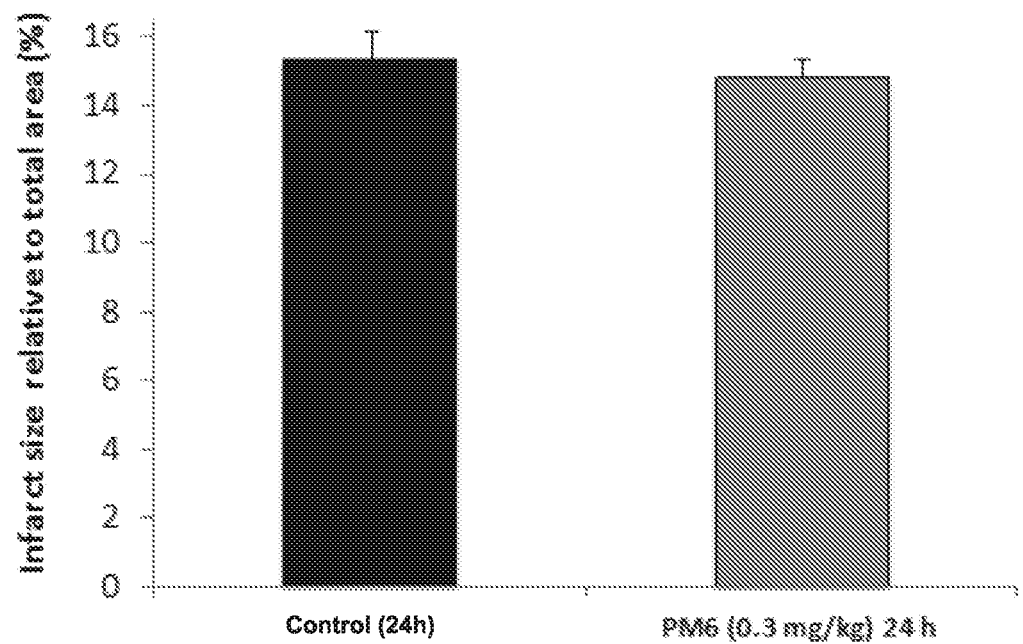
FIGS. 16A-16B are bar graphs showing the effect of intravenous administration of an exemplary decoy peptide PM6 (0.3 mg/kg) 1 hour after inducing ischemia in mice, on the infarct size in the left ventricular. Infract size was measured 24 h (FIG. 16A) and 7 days (FIG. 16B) after the ischemic event. Control are ischemic mice not treated with PM6.
Figure 16B:
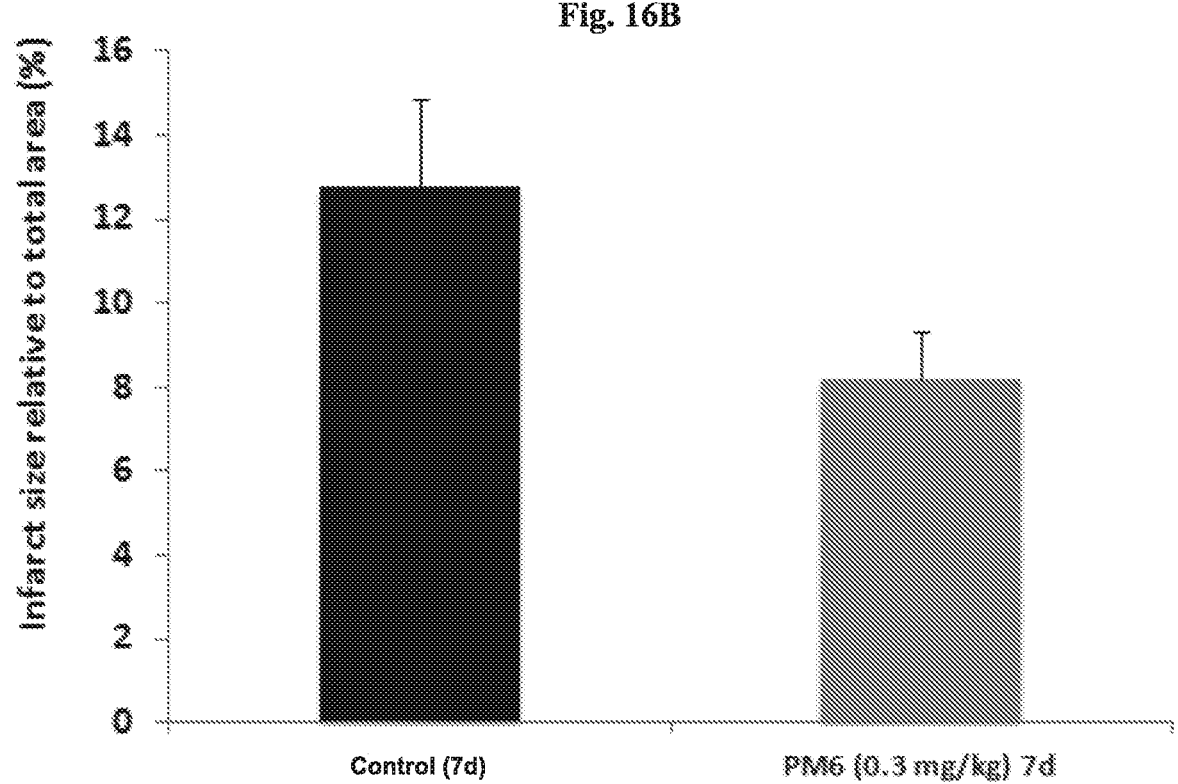

As seen in FIGS. 16A-16 B, infarct size was significantly reduced 7 days after administration of PM6.

Furthermore, as seen FIGS. 17A-17D, a histological evaluation of the myocardial tissue damage using H&E and Masson trichrome staining (left ventricle) as described in Materials and Methods, revealed that a massive damage as seen by leukocytes infiltration and fibrosis was observed in control mice (FIGS. 17A, 17C) but did not develop in the decoy peptide treated group (FIGS. 17B, 17D).

Figure 18A:
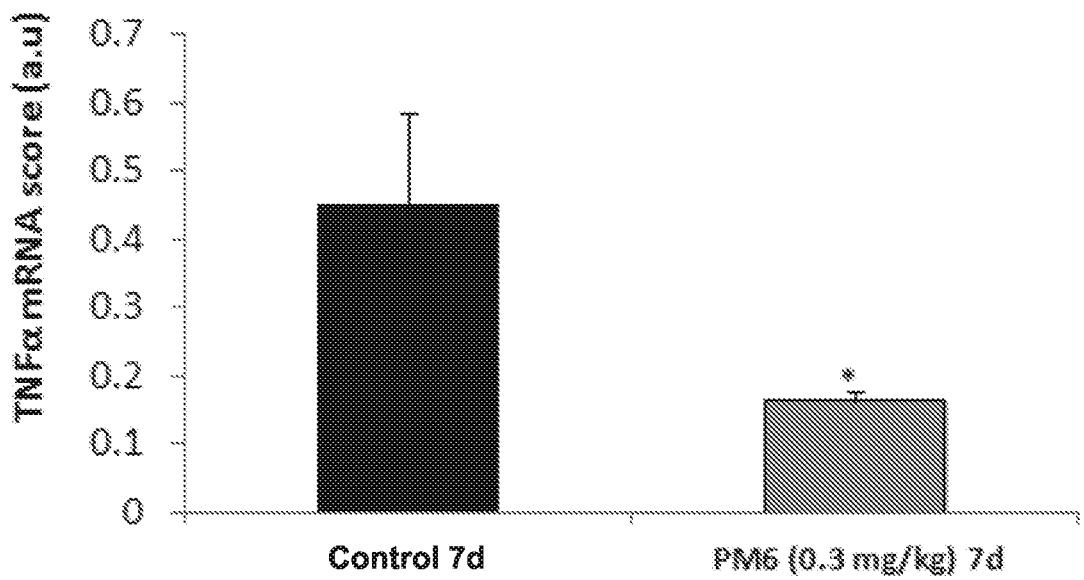
FIGS. 18A-18B are bar graphs showing the effect of an exemplary decoy peptide PM6 on the level of TNF-α mRNA in mouse myocardium as measured by RT-qPCR 24 h (FIG. 18A) and 7 days (FIG. 18B) after inducing ischemia in mice. PM6 (0.3 mg/kg) was administered IV 1 hour after ischemia induction. Control are ischemic mice not treated with PM6. mRNA scores are expressed in arbitrary units (a.u.).
Figure 18B:
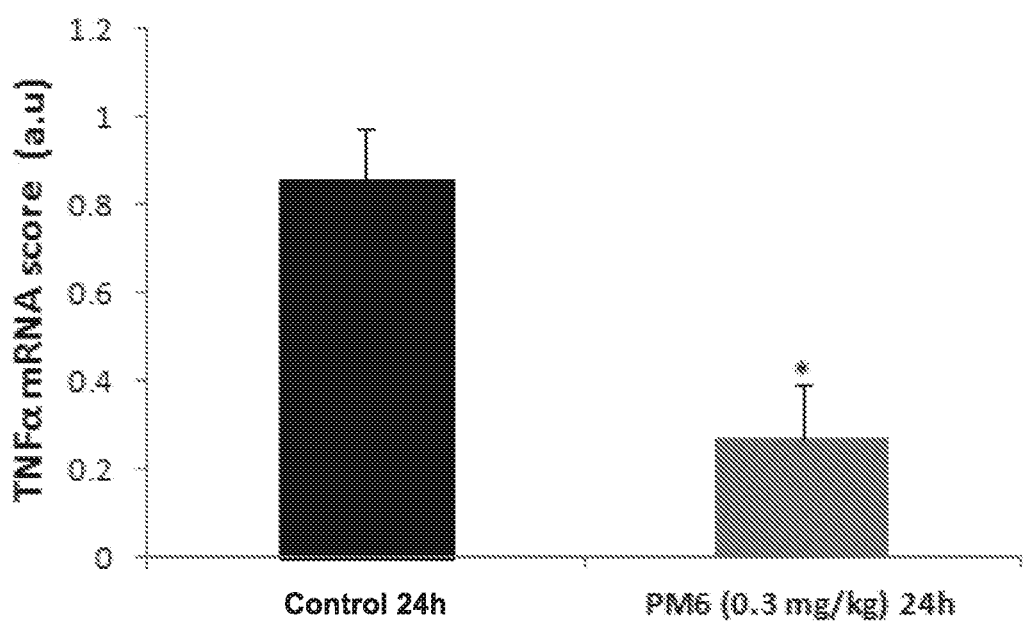

Real time reverse transcriptase PCR (RT-qPCR) was conducted to identify the effect of a disclosed decoy peptide on TLR-mediated induction of the inflammatory cytokine TNF-α. The effect of an exemplary decoy peptide PM6 (0.3 mg/kg; administered 1 hour after MI induction) on TNF-α mRNA expression in mice myocardium was assessed 24 h and 7 days after ischemia induction. Twelve (12) ischemic mice were treated with PM6, whereas 12 ischemic mice did not receive any treatment (control). The results are shown in FIGS. 18A and 18B. As seen in these figures, at both time points PM6 conferred a significant reduction in TNF-α mRNA levels.

Finally, all 12 mice treated with PM6 showed 100% survival rate 7 days after ischemia induction. On the other hand, 5 out of 12 untreated mice died, which accounts for a survival rate of 58% after ischemia for the untreated mice.

Although specific embodiments have been described herein, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. A compound represented by the formula (I):

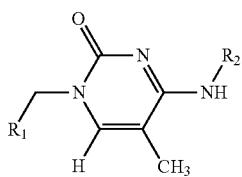

or a stereoisomer, enantiomer or pharmaceutically acceptable salt thereof, wherein
$R_1$ is aryl or heteroaryl; and
$R_2$ is alkyl, alkynyl, or cycloalkyl, wherein the alkyl is a lower alkyl having 3 to 10 carbon atoms; the alkynyl is a medium size alkynyl having 2 to 8 carbon atoms; the cycloalkyl is a saturated, all-carbon monocyclic or polycyclic (fused ring) group, having 3 to 8 carbon atoms; the aryl is an all-carbon, non-saturated monocyclic or (fused-ring group having 6 to 10 carbon atoms; and the heteroaryl is a non-saturated monocyclic or polycyclic (fused ring) group having in the ring(s) one or more heteroatoms selected from nitrogen, oxygen and sulfur;
wherein the alkyl, alkynyl, cycloalkyl and aryl are optionally substituted by one or more groups selected from the group consisting of: S, N, alkyl, mono-, di- or tri-haloalkyl, —O—($C_1$-$C_8$)alkyl, —O—($C_3$-$C_8$)cycloalkyl, hydroxyalkyl, ($C_3$-$C_8$)cycloalkyl, alkenyl, aryl, heterocycloalkyl, halo, OH, O-aryl, —SH, —S—($C_1$-$C_8$)alkyl, —S—($C_3$-$C_8$)cycloalkyl, —S-aryl, —O—S=O, —S(=O)$_2$—R', —CN, —NO$_2$, aralkoxyl, alkylcarbamido, arylcarbamido, alkylamino, arylamino, dialkylamino, diarylamino, arylalkylamino, aminocarbonyl, alkylaminocarbonyl, arylaminocarbonyl, arylcarbonyloxy, carboxyl, alkoxycarbonyl, aryloxycarbonyl, alkylsulfonylamido, alkylsulfinyl, arylsulfinyl, sulfonylamides, sulfones, —P(=O)(OR')(OR"), —PR'R", —C(=O)—R', —C(=S)—R', —C(=O)—O—R', —C(=S)—O—R', —OC(=O)—NR'R", —OC(=S)—NR'R", —OC(=S)—NR'R" and —S(=O)$_2$—NR'R", where R' and R", each independently, is hydrogen, alkyl, alkenyl, cycloalkyl, aryl, heteroaryl (bonded through a ring carbon) or heterocycloalkyl (bonded through a ring carbon).

2. The compound of claim 1, wherein $R_1$ is phenyl or naphthyl, optionally substituted by a haloalkyl group or a nitro group.

3. The compound of claim 1, wherein $R_2$ is selected from the group consisting of: a linear or branched lower alkyl, optionally substituted with one or more phenyl or amino groups; and an optionally substituted cycloalkyl.

4. The compound of claim 3, wherein the cycloalkyl is cyclopentyl or cyclohexyl.

5. The compound of claim 1, selected from the group consisting of compounds PM1-PM10:
1-benzyl-4-(sec-butylamino)-5-methylpyrimidin-2(1H)-one (PM1);
1-benzyl-4-(isopentylamino)-5-methylpyrimidin-2(1H)-one (PM2);
1-benzyl-4-(cyclopentylamino)-5-methylpyrimidin-2(1H)-one (PM3);
1-benzyl-4-((3-(dimethylamino)propyl)amino)-5-methylpyrimidin-2(1H)-one (PM4);
1-benzyl-4-(benzylamino)-5-methylpyrimidin-2(1H)-one (PM5);
1-benzyl-5-methyl-4-(octylamino)pyrimidin-2(1H)-one (PM6);
5-methyl-1-(4-nitrobenzyl)-4-(octylamino)pyrimidin-2(1H)-one (PM7);
5-methyl-1-(naphthalen-2-ylmethyl)-4-(octylamino)pyrimidin-2(1H)-one (PM8);
5-methyl-4-(octylamino)-1-(4-(trifluoromethyl)benzyl)pyrimidin-2(1H)-one (PM9); and
1-benzyl-4-(decylamino)-5-methylpyrimidin-2(1H)-one (PM10).

6. The compound 1-benzyl-5-methyl-4-(octylamino)pyrimidin-2(1H)-one (PM6).

7. A pharmaceutical composition comprising a pharmaceutically acceptable carrier and a decoy peptide according to claim 1.

8. The pharmaceutical composition of claim 7, wherein the compound of formula (I) is 1-benzyl-5-methyl-4-(octylamino)pyrimidin-2(1H)-one (PM6).

9. The pharmaceutical composition of claim 7, wherein the compound of formula (I) interferes with binding to a Toll/interleukin 1 receptor (TIR) domain of TLR4 and inhibits a TLR4-induced signaling pathway.

10. A method for inhibiting induction of toll-like receptor 4 (TLR4) signaling pathway, the method comprising administering to a subject in need thereof a therapeutically effective amount of at least one compound according to claim 1.

11. The method of claim 10, wherein the TLR4 signaling pathway is induced by activation of the immune system following release of pathogen-associated microbial patterns (PAMPs), or release of danger-associated molecular patterns (DAMPS).

12. The method of claim 10, wherein inhibiting induction of TLR4 signaling pathway is in treatment of a disease or disorder associated with induction of TLR4 signaling pathway is selected from the group consisting of a disease or disorder secondary to a cardiovascular disease (CVD); sepsis, an inflammatory disease, a neurodegenerative disorder; a liver disease; and an atherosclerotic disease.

13. The method of claim 12, wherein the disease or disorder associated with induction of TLR4 signaling pathway is a disease or disorder secondary to a CVD, or sepsis.

14. The method of claim 12, wherein the cardiovascular disease or disorder is selected from the group consisting of angina, myocardial infarction (MI), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis.

15. The method of claim 14, wherein the cardiovascular disease or disorder is myocardial infarction or angina.

16. The method of claim 10, wherein the compound is 1-benzyl-5-methyl-4-(octylamino)pyrimidin-2(1H)-one (PM6).

\* \* \* \* \*